(12) United States Patent
Blaskovich et al.

(10) Patent No.: US 8,440,653 B2
(45) Date of Patent: *May 14, 2013

(54) 3-SUBSTITUTED-1,4-DIAZEPAN-2-ONE MELANOCORTIN-5 RECEPTOR ANTAGONISTS

(75) Inventors: Mark Arnold Thomas Blaskovich, Bardon QSLD (AU); Peter Joseph Cassidy, Ashgrove QSLD (AU)

(73) Assignee: Mimetica Pty Ltd, Milton, Queensland (AU)

( * ) Notice: Subject to any disclaimer, the term of this patent is extended or adjusted under 35 U.S.C. 154(b) by 54 days.

This patent is subject to a terminal disclaimer.

(21) Appl. No.: 12/919,973

(22) PCT Filed: Feb. 27, 2009

(86) PCT No.: PCT/AU2009/000232
§ 371 (c)(1),
(2), (4) Date: Nov. 23, 2010

(87) PCT Pub. No.: WO2009/105825
PCT Pub. Date: Sep. 3, 2009

(65) Prior Publication Data
US 2011/0059952 A1    Mar. 10, 2011

Related U.S. Application Data

(60) Provisional application No. 61/032,898, filed on Feb. 29, 2008.

(51) Int. Cl.
*C07D 243/08* (2006.01)
*C07D 401/06* (2006.01)
*C07D 401/12* (2006.01)
*A61K 31/551* (2006.01)

(52) U.S. Cl.
USPC .......................................... 514/218; 540/492

(58) Field of Classification Search .... 540/492; 514/218
See application file for complete search history.

(56) References Cited

U.S. PATENT DOCUMENTS
2003/0232807 A1    12/2003 Poindexter et al.

FOREIGN PATENT DOCUMENTS
| WO | WO 99/48913 A1 | 9/1999 |
| WO | WO 03/013571 | 2/2003 |
| WO | WO 03/068738 | 8/2003 |
| WO | WO 2008/017852 A1 | 2/2008 |

OTHER PUBLICATIONS

International Search Report issued for PCT/AU2009/000232 dated Mar. 26, 2009.
Irani, et al., "Progress in the Development of Melanocortin Receptor Selective Ligands", vol. 10, Jan. 1, 2004, pp. 3443-3479.
Extended European Search Report issued on Apr. 11, 2011 for European Application No. 09716109.5.
Office Action issued for Chinese Application No. 2009801131587, (2009).

*Primary Examiner* — Bruck Kifle
(74) *Attorney, Agent, or Firm* — Knobbe, Martens, Olson & Bear, LLP

(57) ABSTRACT

The present invention provides compounds of Formula (I) that are useful for modulating the biological activity of the melanocortin-5 receptor (MC5R). Compounds of this invention can be used to treat diseases and/or conditions in which downregulation of MC5R is beneficial. Such diseases and/or conditions include, but are not limited to, acne, seborrhea, seborrheic dermatitis, cancer, and inflammatory diseases.

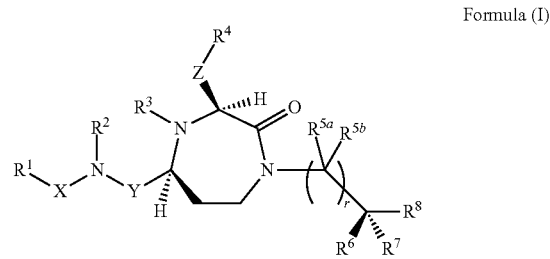

Formula (I)

19 Claims, No Drawings

3-SUBSTITUTED-1,4-DIAZEPAN-2-ONE MELANOCORTIN-5 RECEPTOR ANTAGONISTS

This application is U.S. National Phase of International Application No. PCT/AU2009/000232, filed Feb. 27, 2009, designating the United States, and published as WO 2009/105825 on Sep. 3, 2009, which claims priority to U.S. Provisional Patent Application No. 61/032,898, filed Feb. 29, 2008.

FIELD OF THE INVENTION

The present invention relates to the field of melanocortin-5 receptor antagonists. In particular the present invention relates to a family of 1,4-diazepan-2-ones and derivatives thereof that are antagonists of the melanocortin-5 receptor. The invention also relates to pharmaceutical compositions containing these compounds.

BACKGROUND OF THE INVENTION

The melanocortin-5 receptor (MC5R) is a G-protein coupled receptor (GPCR) belonging to the family of melanocortin receptors. There are five melanocortin receptors that have been isolated and cloned to date: MC1R, MC2R, MC3R, MC4R and MC5R. The melanocortin receptors participate in a variety of physiologic functions, providing a number of opportunities for therapeutic intervention in physiologic processes through alteration (i.e., a statistically significant increase or decrease) or modulation (e.g., up-regulation or down-regulation) of melanocortin receptor signalling activity.

Reviews of the melanocortin receptors, and their potential as targets for therapy have been published (Wikberg 2001; Bohm 2006). The melanocortin receptor family members are regulated by natural peptide agonists such as ACTH and the melanocyte-stimulating hormones ($\alpha$-, $\beta$-, $\gamma$-MSH) derived from pro-opiomelanocortin (POMC) and by peptide antagonists such as Agouti signal protein (ASP) and Agouti-related peptide (AGRP). The MC1R is widely expressed and is associated with pigmentation in melanocytes and with inflammation responses in many cells involved in the immune system. The MC2R differs from the other melanocortin receptors in that it binds only ACTH but not MSH ligands. It is highly expressed in the adenal gland and controls corticosteroid synthesis. The MC3R is found in the brain, but also elsewhere in the body, and appears to play a role in the regulation of energy homeostasis, and possibly sexual dysfunction. The MC4R is found almost exclusively in the brain, with some reports of its presence elsewhere. It has been strongly associated with feeding control, and also implicated with sexual desire. The MC5R is widely expressed in peripheral tissues, particularly in the exocrine glands, with some receptor also expressed in the brain. Given the breadth of activity associated with the melanocortin receptors it is desirable when seeking to target one of these receptors to do so selectively in order to avoid side effects associated with antagonism or agonism of another receptor in this family.

The MC5R has been cloned and expressed from multiple species, including humans in 1993 (though called MC2 in this paper) (Chhajlani 1993), rat in 1994 (Griffon 1994) mice in 1994 (Gantz 1994; Labbé 1994) and in 1995 (Fathi 1995), canine (Houseknecht 2003), rhesus monkey (Huang 2000), sheep (Barrett 1994), zebrafish (Ringholm 2002), goldfish (Cerdá-Reverter 2003), spiny dogfish (Klovins 2004), rainbow trout (Haitina 2004), and chicken (Ling 2004), with the MC5R gene also identified in pig (Kim 2000). Patents covering the MC5R sequence in humans (Wikberg 2002), mice (Yamada 1997), rhesus monkey (Fong 2003) and dogs (Houseknecht 2003) have been published.

The MC5R has been implicated in regulating sebum secretion by a number of studies, as summarized in 2006 (Zhang 2006). Mice lacking MC5R have reduced sebum production, as evidenced by a marked inability to shed water from their fur, and a reduced quantity of sebum isolated from their hair. Significantly, these mice were otherwise generally healthy, with no readily visible abnormalities (appearance, behaviour, growth, muscle mass, adipose mass, reproduction, basal and stress-induced corticosterone, glucose and insulin levels) (Chen 1997). Further studies have identified reductions in pheromones, causing alterations in aggressive behaviours between mice (Caldwell 2002; Morgan 2004a; Morgan 2004b; Morgan 2006). Mice in which the POMC-derived peptide native ligands of MC5R have been knocked out show a similar phenotype (Yaswen 1999). Rats injected with $\alpha$-MSH had 30-37% increased rates of sebum production, while removal of the neurointermediate lobe (the source of MSH) caused a 35% decrease in sebum secretion, which was restored upon administration of $\alpha$-MSH (Thody 1973). A synergistic effect between $\alpha$-MSH and testosterone was observed in rats, with testosterone increasing sebaceous gland and cell volumes (presumably via increased proliferation), $\alpha$-MSH increasing dermal lipogenesis, and the combination increasing sebum secretion (Thody 1975a; Thody 1975b).

At a cellular level human sebocytes have been shown to express MC5R, via detection of MC5R transcripts in microdissected sebaceous glands (Thiboutot 2000), detection of MC5R in human facial sebaceous glands by immunostaining (Hatta 2001), detection of MC5R mRNA and MC5R in human sebaceous glands, cultured human sebocytes and rat preputial cells (Thiboutot 2000) and detection of MC5R as punctate particles within sebaceous glands by staining with polyclonal antibodies, seen in differentiated but not undifferentiated sebocytes (Zhang 2006). MC5R mRNA was also detected in sebaceous glands from the skin of wild-type mice, but not in skin sections of the MC5R-knockout mice (Chen 1997). Treatment of human sebocytes with cholera toxin (ChT), bovine pituitary extract (BPE), $\alpha$-MSH or NDP-MSH increases lipid droplet formation, squalene synthesis, and MC5R expression (Zhang 2003; Zhang 2006). While both MC1R and MC5R have been detected in sebaceous cells, treatment of primary human sebocyte cell culture with NDP-MSH or BPE caused a substantial increase in human MC5R expression compared to serum-free conditions, correlating with sebocyte differentiation. Immortalized sebaceous cell lines (SZ-95, TSS-1 and SEB-1) also show MC5R expression (Jeong 2007; Smith 2007a; Phan 2007). These studies suggest that MC5R antagonists could be useful in reducing sebum secretion in mammals and hence in treating conditions associated with excess sebum secretion.

A family of 1,2,4-thiadiazole derivatives with MC5R antagonist activity (138-320 nM) were found to reduce sebum formation both in human sebocyte cell cultures and when applied topically to human skin grafted onto immunodeficient mice (Eisinger 2003a-d; 2006a,b).

Excessive sebum secretion, or seborrhoea, is a common affliction. Sebaceous glands occur over most of the body, with dense concentrations of large glands on the face, scalp and upper trunk (Simpson and Cunliffe p 43.1). Sebaceous secretion is dependent in part on androgenic hormones, possibly partly mediated by 5$\alpha$-reductase processing of testosterone to 5$\alpha$-DHT (dihydrotestosterone). Sebum consists of a species-specific mixture of lipids. In humans this consists of approximately 58% glycerides, 26% wax esters, 12% squalene, and 4% cholesterol/cholesterol esters (Simpson and Cunliffe p 43.5). The presence of squalene is almost exclusively characteristic of human sebum. The function of sebum is not well defined, but it is believed to have fungistatic properties, and play a role in moisture loss from, and water repellence of, the epidermis (Simpson and Cunliffe p 43.6; Danby 2005; Porter 2001; Shuster 1976; Kligman 1963).

Excessive sebum secretion has been associated with the development of acne vulgaris. Acne vulgaris is a common disease affecting an estimated 80% of the world's population at some stage in their lives. A person is more likely to develop acne than any other disease, although the severity varies greatly (Simpson and Cunliffe p 43.16). Acne peaks in prevalence and severity in adolescents aged 14-19 years old, with approximately 35-40% affected, but in a significant number of patients (7-24%) it persists beyond 25 years of age (Simpson and Cunliffe p 43.15). Of patients treated for acne, one study found 80% still had symptoms at 30-40 years of age (Simpson and Cunliffe p 43.16). While acne is not a life-threatening disease it can have a severe impact on a patient's quality of life (Follador 2006), with one study of severe acne patients showing similar impact as much more serious chronic medical conditions such as asthma, epilepsy, diabetes, back pain or arthritis (Mallon 1999).

Four major factors are believed to be involved in the pathogenesis of acne: (i) increased sebum production (seborrhoea), (ii) hypercornification/blockage of the pilosebaceous duct (comedogenesis), (iii) infection of the duct with *P. acnes*, and (iv) inflammation of the pilosebaceous duct (Simpson and Cunliffe p 43.15; Williams 2006). A number of studies have demonstrated a clear link between increased production of sebum, and the presence and severity of acne (Simpson and Cunliffe p 43.17; Youn 2005; Piérard 1987; Harris 1983; Cotterill 1981; Thody 1975c; Pochi 1964). A 2007 study found a correlation between sebum excretion and development of acne in preadolescent children (Mourelatos 2007). Sebum is the main nutrient of *P. acnes*, thus reduction of sebum will reduce the subsequent bacterial infection and inflammation response.

Androgenic sex hormones appear to play a role in the development of acne, with strong correlations with sebum production (Makrantonaki 2007). Two oral contraceptive pills are approved by the FDA for the treatment of acne vulgaris (Harper 2005), and these compounds appear to act by reducing androgen mediated sebum formation. Diet (Cordain 2005; Smith 2007b), stress (Zouboulis 2004) and genetic factors (Goulden 1999; Bataille 2006) also may play a role in acne, again potentially via increased sebum production.

Current treatments for acne vulgaris focus predominantly on treating the infection and inflammation stages of the disease, with a large number of different formulations of topical antibiotics (e.g. benzoyl peroxide, tetracycline, erythromycin, clindamycin) and retinoids (e.g. retinoic acid, isotretinoin, adapalene, tazarotene) in use, either alone or in combination; some of these also possess anti-inflammatory action (Simpson and Cunliffe p 43.36-43.38). Many of these treatments are of limited efficacy, particularly for severe cases of acne. A growing problem is the development of antibiotic-resistant strains of *P. acnes* (Simpson and Cunliffe p 43.37, 43.46; Williams 2006). Both topical retinoids and benzoyl peroxide cause skin irritation, and retinoids can cause photosensitivity (Williams 2006). Oral therapies include isotretinoin, antibiotics, hormones, and steroids. In females, antiandrogens have been shown to reduce sebum production (by approximately 40-80%, though with no placebo control group) and improve acne (Simpson and Cunliffe p 43.44; Burke 1984; Goodfellow 1984). Laser and UV-based therapies are gaining acceptance, and are believed to act through heating of the sebaceous gland followed by reduction in sebum formation; with reductions in both sebum formation and acne lesions measured (Jih 2006; Bhardwaj 2005). Of the many therapies available for acne, only oral isotretinoin and hormonal therapies act by regulating the sebaceous gland to reduce sebum secretion (Clarke 2007).

The most effective acne treatment, oral isotretinoin (13-cis-retinoic acid, Roaccutane, Accutane) was introduced in 1983 and still remains the most clinically effective anti-acne therapy. It is the only known treatment with strong sebusuppressive activity, reducing sebum excretion by up to 90% after 8-12 weeks of therapy (60-70% by 2 weeks) (Simpson and Cunliffe p 43.47; Jones 1983; Goldstein 1982; King 1982). Topical retinoids, in contrast, have no effect on sebum production. Oral isotretinoin is also anti-inflammatory, reduces comedogenesis, and reduces *P. acnes* infection. The mechanism of action is still unclear, and metabolites of isotretinoin appear to play a significant role. Isotretinoin induces apoptosis and cell cycle arrest in human immortalized SEB-1 sebocyte cell culture (Nelson 2006). Unfortunately, oral isotretinoin has serious side effects; most significantly it is a teratogen and requires a registration program for use in the USA. The FDA has issued a warning against online purchases of isotretinoin. Blood testing for fasting lipids and liver function is also recommended during treatment (Williams 2006). Isotretinoin has been implicated (though not substantively) with adverse psychological effects, including suicide and depression (Marqueling 2005).

Other forms of acne, such as acne conglobata or acne fulminans, may also respond to a sebum-reducing agent. Seborrhoea, or excessive skin oil production, is often associated with severe acne. Seborrheic dermatitis (SD) is a skin disease associated with sebum-rich areas of the scalp, face and trunk with scaly, flaky, itchy red skin affecting 3-5% of the population; dandruff represents a mild form of this dermatitis affecting 15-20% of the population. Seborrhoea and SD appear more common in patients with Parkinson's disease or mood disorders (facial paralysis, supraorbital injury, poliomyelitis, syringomyelia, quadriplegia, unilateral injury to the ganglion Gasser and those with HIV/AIDS) (Plewig 1999). Studies have shown that seborrheic dermatitis is also associated with chronic alcoholic pancreatitis, hepatitis C virus and various cancers. It is also common in patients with genetic disorders, such as Down's syndrome, Hailey-Hailey disease and cardio-facio cutaneous syndrome (Gupta 2004). MC5R antagonists may be useful for treating these indications.

Although rare, a variety of tumours involving sebaceous glands or sebaceous cells have been described (e.g. Ide 1999; Mariappan 2004; Kruse 2003). Muir-Torre syndrome consists of sebaceous gland adenomas associated with an internal adenocarcinoma (usually colon, breast, ovary or prostate). Preventing sebaceous cell differentiation may provide an effective treatment for arresting tumour growth. Oral isotretinoin has been used for this purpose (Graefe 2000). Sebaceous hyperplasia is a benign hyperplasia of the sebaceous glands, generating yellowish small papules on the skin surface, usually the face. The disease is associated with excessive undifferentiated sebocyte proliferation, but not excessive sebum formation. Ectopic sebaceous glands (Fordyce spots) are similar yellow papules found in the mouth or on the penile shaft. Both respond to oral isotreinoin. A compound that reduced sebocyte proliferation could be an effective treatment.

α-MSH shows immunosuppressive effects in humans, suppressing a variety of inflammation responses, and the MC5R has been implicated in these immunomodulating activities. MC5R mRNA was found to be expressed at high levels in human CD4+ T helper (Th) cells and in moderate levels in other human peripheral blood leukocytes (Andersen 2005). In mice, MC5R was detected in the lymphoid organs (Labbé, 1994), and MC5R was found on the surface of mouse pro-B-lymphocyte cells where it appears to mediate α-MSH activation of the JAK2 signalling pathway, enhancing cellular proliferation (Buggy 1998). Induction of CD25+ CD4+ regulatory T-cells by α-MSH also appears to be through MC5R (Taylor 2001).

For the reasons described above it would be desirable to provide MC5R antagonists that could be used in a number of therapeutic areas. Therapeutic regulation of biological signal transduction includes modulation of MC5R-mediated cellular events including, inter alia, inhibition or potentiation of interactions among MC5R-binding and activating or deactivating molecules, or of other agents that regulate MC5R activities. An increased ability to so regulate MC5R may facilitate the development of methods for modulating sebum secretion or other biological processes, and for treating conditions associated with such pathways such as acne as described above.

The present applicants have now identified a family of 1,4-diazepan-2-ones that display MC5R antagonist activity which should be useful in treating MC5R related conditions.

SUMMARY OF THE INVENTION

The present invention provides compounds of formula (I):

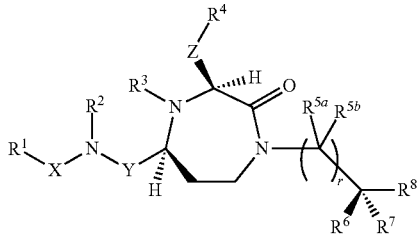

Formula (I)

wherein:

Y is a group of formula —$(CR^9R^{10})_n$—;

X is selected from the group consisting —C(=O)—, —OC(=O)—, —NHC(=O)—, —$(CR^{11}R^{12})_s$—, and —S(=O)$_2$—;

Z is a group of formula —$(CR^{13}R^{14})_q$—;

$R^1$ is selected from the group consisting of H, optionally substituted $C_1$-$C_{12}$alkyl, optionally substituted $C_2$-$C_{12}$alkenyl, optionally substituted $C_2$-$C_{12}$alkynyl, optionally substituted $C_1$-$C_{12}$heteroalkyl, optionally substituted $C_3$-$C_{12}$cycloalkyl, optionally substituted $C_2$-$C_{12}$heterocycloalkyl, optionally substituted $C_6$-$C_{18}$aryl, and optionally substituted $C_1$-$C_{18}$heteroaryl;

$R^2$ and $R^3$ are each independently selected from the group consisting of H, optionally substituted $C_1$-$C_{12}$alkyl, optionally substituted $C_2$-$C_{12}$alkenyl, optionally substituted $C_2$-$C_{12}$alkynyl, optionally substituted $C_1$-$C_{12}$heteroalkyl, optionally substituted $C_3$-$C_{12}$cycloalkyl, optionally substituted $C_2$-$C_{12}$heterocycloalkyl, optionally substituted $C_6$-$C_{18}$aryl, and optionally substituted $C_1$-$C_{18}$heteroaryl;

$R^4$ is selected from the group consisting of H, $C_1$-$C_{12}$alkyl, optionally substituted $C_2$-$C_{12}$alkenyl, optionally substituted $C_2$-$C_{12}$alkynyl, $C_3$-$C_{12}$cycloalkyl, optionally substituted $C_6$-$C_{18}$aryl, optionally substituted C-linked $C_1$-$C_{18}$heteroaryl, C(=O)$R^{15}$, C(=O)N$R^{16}R^{17}$, —C(=NR$^{16}$)NR$^{17}$R$^{18}$, SR$^{20}$, SC(=O)R$^{20}$, SO$_2$R$^{20}$, OR$^{20}$, ONR$^{16}$R$^{17}$, OCR$^{17}$R$^{18}$R$^{20}$, OC(=O)R$^{20}$, OC(=O)OR$^{20}$, OC(=O)NR$^{16}$R$^{17}$, and ONR$^{16}$C(=NR$^{17}$)NR$^{18}$R$^{19}$.

each $R^{5a}$ and $R^{5b}$ are independently selected from the group consisting of H, halogen, $C_1$-$C_{12}$alkyl, $C_1$-$C_{12}$hydroxyalkyl and $C_1$-$C_{12}$haloalkyl, or one or more of $R^{5a}$ and $R^{5b}$ when taken together with one or more of $R^6$, $R^7$ and $R^8$ and the atoms to which they are attached form a moiety selected from the group consisting of an optionally substituted $C_3$-$C_{12}$cycloalkyl, optionally substituted $C_2$-$C_{12}$ heterocycloalkyl, optionally substituted $C_6$-$C_{18}$aryl, and optionally substituted $C_1$-$C_{18}$heteroaryl;

$R^6$, $R^7$ and $R^8$ are each independently selected from the group consisting of H, halogen, hydroxy, optionally substituted $C_1$-$C_{12}$alkyl, optionally substituted $C_2$-$C_{12}$alkenyl, optionally substituted $C_2$-$C_{12}$alkynyl, optionally substituted $C_1$-$C_{12}$ heteroalkyl, optionally substituted $C_1$-$C_{10}$ heteroalkenyl, optionally substituted $C_3$-$C_{12}$cycloalkyl, optionally substituted $C_2$-$C_{12}$ heterocycloalkyl, optionally substituted $C_6$-$C_{18}$aryl, optionally substituted $C_1$-$C_{18}$heteroaryl, optionally substituted amino, optionally substituted carboxy, $C_1$-$C_{12}$alkyloxy, and optionally substituted thio, or (a) when taken together with the carbon atom to which they are attached two or more of $R^6$, $R^7$ and $R^8$ form a moiety selected from the group consisting of optionally substituted $C_2$-$C_{12}$alkenyl, optionally substituted $C_3$-$C_{12}$cycloalkyl, optionally substituted $C_2$-$C_{12}$heterocycloalkyl, optionally substituted $C_6$-$C_{18}$aryl, and optionally substituted $C_1$-$C_{18}$heteroaryl, or (b) one or more of $R^6$, $R^7$ and $R^8$ when taken together with one or more of $R^{5a}$ and $R^{5b}$ and the atoms to which they are attached form a moiety selected from the group consisting of an optionally substituted $C_3$-$C_{12}$cycloalkyl, optionally substituted $C_2$-$C_{12}$ heterocycloalkyl, optionally substituted $C_6$-$C_{18}$aryl, and optionally substituted $C_1$-$C_{18}$heteroaryl;

each $R^9$ and $R^{10}$ is independently selected from the group consisting of H and optionally substituted $C_1$-$C_{12}$alkyl;

each $R^{11}$ and $R^{12}$ is independently selected from the group consisting of H, and optionally substituted $C_1$-$C_{12}$alkyl;

each $R^{13}$ and $R^{14}$ is independently selected from the group consisting of H, halogen, OH, $C_1$-$C_{12}$alkyl, $C_3$-$C_{12}$cycloalkyl, $C_6$-$C_{18}$aryl, $C_1$-$C_{12}$haloalkyl, $C_1$-$C_{12}$hydroxyalkyl, $C_1$-$C_{12}$alkyloxyl, and $C_1$-$C_{12}$haloalkyloxyl, or when taken together with the carbon to which they are attached $R^{13}$ and $R^{14}$ form a $C_3$-$C_{12}$cycloalkyl group, or, one of $R^{13}$ or $R^{14}$ when taken together with one of $R^{15}$ or $R^{20}$ and the atoms to which they are attached form a cyclic group;

$R^{15}$ is independently selected from the group consisting of H, optionally substituted $C_1$-$C_{12}$alkyl, optionally substituted $C_3$-$C_{12}$cycloalkyl, optionally substituted $C_6$-$C_{18}$aryl, and optionally substituted $C_1$-$C_{18}$heteroaryl, each $R^{16}$, $R^{17}$, $R^{18}$, $R^{19}$ and $R^{20}$ is independently selected from the group consisting of H, optionally substituted $C_1$-$C_{12}$alkyl, optionally substituted $C_1$-$C_{12}$heteroalkyl, optionally substituted $C_3$-$C_{12}$cycloalkyl, optionally substituted $C_6$-$C_{18}$aryl, and optionally substituted $C_1$-$C_{18}$heteroaryl, or any two of $R^{16}$, $R^{17}$, $R^{18}$, $R^{19}$, and $R^{20}$ when taken together with the atoms to which they are attached form an optionally substituted cyclic group, or $R^{15}$ or $R^{20}$, when taken together with one of $R^{13}$ or $R^{14}$ and the atoms to which they are attached, form a cyclic group;

n is an integer selected from the group consisting of 1, 2, 3 and 4;

q is an integer selected from the group consisting of 0, 1, 2, 3, 4, and 5;

r is an integer selected from the group consisting of 1, 2, 3, and 4;

s is an integer selected from the group consisting of 1, 2, 3, and 4;

or a pharmaceutically acceptable salt or prodrug thereof.

The invention also relates to pharmaceutical compositions including a compound of the invention with a pharmaceutically acceptable carrier, diluent or excipient.

DETAILED DESCRIPTION OF THE INVENTION

In this specification a number of terms are used which are well known to a skilled addressee. Nevertheless for the purposes of clarity a number of terms will be defined.

As used herein, the term "unsubstituted" means that there is no substituent or that the only substituents are hydrogen.

The term "optionally substituted" as used throughout the specification denotes that the group may or may not be further substituted or fused (so as to form a condensed polycyclic system), with one or more non-hydrogen substituent groups. In certain embodiments the substituent groups are one or more groups independently selected from the group consisting of halogen, =O, =S, —CN, —NO$_2$, —CF$_3$, —OCF$_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, cycloalkylalkyl, heterocycloalkylalkyl, heteroarylalkyl, arylalkyl, cycloalkylalkenyl, heterocycloalkylalkenyl, arylalkenyl, heteroarylalkenyl, cycloalkylheteroalkyl, heterocycloalkylheteroalkyl, arylheteroalkyl, heteroarylheteroalkyl, hydroxy, hydroxyalkyl, alkyloxy, alkyloxyalkyl, alkyloxycycloalkyl, alkyloxyheterocycloalkyl, alkyloxyaryl, alkyloxyheteroaryl, alkyloxycarbonyl, alkylaminocarbonyl, alkenyloxy, alkynyloxy, cycloalkyloxy, cycloalkenyloxy, heterocycloalkyloxy, heterocycloalkenyloxy, aryloxy, phenoxy, benzyloxy, heteroaryloxy, arylalkyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, alkylsulfinyl, arylsulfinyl, aminosulfinylaminoalkyl, —C(=O)OH, —C(=O)R$^a$, —C(=O)OR$^a$, C(=O)NR$^a$R$^b$, C(=NOH)R$^a$, C(=NR$^a$)NR$^b$R$^c$, NR$^a$R$^b$, NR$^a$C(=O)R$^b$, NR$^a$C(=O)OR$^b$, NR$^a$C(=O)NR$^b$R$^c$, NR$^a$C(=NR$^b$)NR$^c$R$^d$, NR$^a$SO$_2$R$^b$, —SR$^a$, SO$_2$NR$^a$R$^b$, —OR$^a$, OC(=O)NR$^a$R$^b$, OC(=O)R$^a$ and acyl, wherein R$^a$, R$^b$, R$^c$ and R$^d$ are each independently selected from the group consisting of H, C$_1$-C$_{12}$ alkyl, C$_1$-C$_{12}$ haloalkyl, C$_2$-C$_{12}$ alkenyl, C$_2$-C$_{12}$ alkynyl, C$_1$-C$_{10}$ heteroalkyl, C$_3$-C$_{12}$ cycloalkyl, C$_3$-C$_{12}$ cycloalkenyl, C$_1$-C$_{12}$ heterocycloalkyl, C$_1$-C$_{12}$ heterocycloalkenyl, C$_6$-C$_{18}$aryl, C$_1$-C$_{18}$heteroaryl, and acyl, or any two or more of R$^a$, R$^b$, R$^c$ and R$^d$, when taken together with the atoms to which they are attached form a heterocyclic ring system with 3 to 12 ring atoms.

In one embodiment each optional substituent is independently selected from the group consisting of: halogen, =O, =S, —CN, —NO$_2$, —CF$_3$, —OCF$_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, hydroxy, hydroxyalkyl, alkyloxy, alkyloxyalkyl, alkyloxyaryl, alkyloxyheteroaryl, alkenyloxy, alkynyloxy, cycloalkyloxy, cycloalkenyloxy, heterocycloalkyloxy, heterocycloalkenyloxy, aryloxy, heteroaryloxy, arylalkyl, heteroarylalkyl, arylalkyloxy, amino, alkylamino, acylamino, aminoalkyl, arylamino, sulfonyl, alkylsulfonyl, arylsulfonyl, aminosulfonyl, aminoalkyl, —COOH, —SH, and acyl.

Examples of particularly suitable optional substituents include F, Cl, Br, I, CH$_3$, CH$_2$CH$_3$, OH, OCH$_3$, CF$_3$, OCF$_3$, NO$_2$, NH$_2$, and CN.

In the definitions of a number of substituents below it is stated that "the group may be a terminal group or a bridging group". This is intended to signify that the use of the term is intended to encompass the situation where the group is a linker between two other portions of the molecule as well as where it is a terminal moiety. Using the term alkyl as an example, some publications would use the term "alkylene" for a bridging group and hence in these other publications there is a distinction between the terms "alkyl" (terminal group) and "alkylene" (bridging group). In the present application no such distinction is made and most groups may be either a bridging group or a terminal group.

Several terms are prefaced by the modifier indicating the number of carbon atoms present in the moiety. For example, the modifier "C$_1$-C$_6$" in front of the term "alkyl" indicates that the alkyl moiety has from 1 to 6 carbon atoms. Further, the modifier "C$_1$-C$_{18}$" in front of the term "heteroaryl" indicates that the heteroaromatic ring may have from 1 to 18 carbon atoms as part of the total number of atoms in the ring system.

"Acyl" means an R—C(=O)— group in which the R group may be an alkyl, cycloalkyl, heterocycloalkyl; aryl or heteroaryl group as defined herein. Examples of acyl include acetyl and benzoyl. The group may be a terminal group or a bridging group. If the group is a terminal group it is bonded to the remainder of the molecule through the carbonyl carbon.

"Acylamino" means an R—C(=O)—NH— group in which the R group may be an alkyl, cycloalkyl, heterocycloalkyl, aryl or heteroaryl group as defined herein. The group may be a terminal group or a bridging group. If the group is a terminal group it is bonded to the remainder of the molecule through the nitrogen atom.

"Alkenyl" as a group or part of a group denotes an aliphatic hydrocarbon group containing at least one carbon-carbon double bond and which may be straight or branched preferably having 2-14 carbon atoms, more preferably 2-12 carbon atoms, most preferably 2-6 carbon atoms, in the normal chain. The group may contain a plurality of double bonds in the normal chain and the orientation about each is independently E or Z. Exemplary alkenyl groups include, but are not limited to, ethenyl, propenyl, butenyl, pentenyl, hexenyl, heptenyl, octenyl and nonenyl. The group may be a terminal group or a bridging group.

"Alkenyloxy" refers to an alkenyl-O— group in which alkenyl is as defined herein. Preferred alkenyloxy groups are C$_1$-C$_6$ alkenyloxy groups. The group may be a terminal group or a bridging group. If the group is a terminal group it is bonded to the remainder of the molecule through the oxygen atom.

"Alkyl" as a group or part of a group refers to a straight or branched aliphatic hydrocarbon group, preferably a C$_1$-C$_{14}$ alkyl, more preferably a C$_1$-C$_{10}$ alkyl, most preferably C$_1$-C$_6$ unless otherwise noted. Examples of suitable straight and branched C$_1$-C$_6$ alkyl substituents include methyl, ethyl, n-propyl, 2-propyl, n-butyl, sec-butyl, t-butyl, hexyl, and the like. The group may be a terminal group or a bridging group.

"Alkylamino" includes both mono-alkylamino and dialkylamino, unless specified. "Mono-alkylamino" means a Alkyl-NH— group, in which alkyl is as defined herein. "Dialkylamino" means a (alkyl)$_2$N— group, in which each alkyl may be the same or different and are each as defined herein for alkyl. The alkyl group is preferably a C$_1$-C$_6$ alkyl group. The group may be a terminal group or a bridging group. If the group is a terminal group it is bonded to the remainder of the molecule through the nitrogen atom.

"Alkylaminocarbonyl" refers to a group of the formula $(Alkyl)_x(H)_yNC(=O)$— in which x is 1 or 2, and the sum of x+y=2. The group may be a terminal group or a bridging group. If the group is a terminal group it is bonded to the remainder of the molecule through the carbonyl carbon.

"Alkyloxy" refers to an alkyl-O— group in which alkyl is as defined herein. Preferably the alkyloxy is a $C_1$-$C_6$alkyloxy. Examples include, but are not limited to, methoxy and ethoxy. The group may be a terminal group or a bridging group.

"Alkyloxyalkyl" refers to an alkyloxy-alkyl- group in which the alkyloxy and alkyl moieties are as defined herein. The group may be a terminal group or a bridging group. If the group is a terminal group it is bonded to the remainder of the molecule through the alkyl group.

"Alkyloxyary" refers to an alkyloxy-aryl- group in which the alkyloxy and aryl moieties are as defined herein. The group may be a terminal group or a bridging group. If the group is a terminal group it is bonded to the remainder of the molecule through the aryl group.

"Alkyloxycarbonyl" refers to an alkyl-O—C(=O)— group in which alkyl is as defined herein. The alkyl group is preferably a $C_1$-$C_6$ alkyl group. Examples include, but are not limited to, methoxycarbonyl and ethoxycarbonyl. The group may be a terminal group or a bridging group. If the group is a terminal group it is bonded to the remainder of the molecule through the carbonyl carbon.

"Alkyloxycycloalkyl" refers to an alkyloxy-cycloalkyl- group in which the alkyloxy and cycloalkyl moieties are as defined herein. The group may be a terminal group or a bridging group. If the group is a terminal group it is bonded to the remainder of the molecule through the cycloalkyl group.

"Alkyloxyheteroary" refers to an alkyloxy-heteroaryl- group in which the alkyloxy and heteroaryl moieties are as defined herein. The group may be a terminal group or a bridging group. If the group is a terminal group it is bonded to the remainder of the molecule through the heteroaryl group.

"Alkyloxyheterocycloalkyl" refers to an alkyloxy-heterocycloalkyl- group in which the alkyloxy and heterocycloalkyl moieties are as defined herein. The group may be a terminal group or a bridging group. If the group is a terminal group it is bonded to the remainder of the molecule through the heterocycloalkyl group.

"Alkylsulfinyl" means an alkyl-S—(=O)— group in which alkyl is as defined herein. The alkyl group is preferably a $C_1$-$C_6$ alkyl group. Exemplary alkylsulfinyl groups include, but not limited to, methylsulfinyl and ethylsulfinyl. The group may be a terminal group or a bridging group. If the group is a terminal group it is bonded to the remainder of the molecule through the sulfur atom.

"Alkylsulfonyl" refers to an alkyl-S(=O)$_2$— group in which alkyl is as defined above. The alkyl group is preferably a $C_1$-$C_6$ alkyl group. Examples include, but not limited to methylsulfonyl and ethylsulfonyl. The group may be a terminal group or a bridging group. If the group is a terminal group it is bonded to the remainder of the molecule through the sulfur atom.

"Alkynyl" as a group or part of a group means an aliphatic hydrocarbon group containing a carbon-carbon triple bond and which may be straight or branched preferably having from 2-14 carbon atoms, more preferably 2-12 carbon atoms, more preferably 2-6 carbon atoms in the normal chain. Exemplary structures include, but are not limited to, ethynyl and propynyl. The group may be a terminal group or a bridging group.

"Alkynyloxy" refers to an alkynyl-O— group in which alkynyl is as defined herein. Preferred alkynyloxy groups are $C_1$-$C_6$alkynyloxy groups. The group may be a terminal group or a bridging group. If the group is a terminal group it is bonded to the remainder of the molecule through the oxygen atom.

"Aminoalkyl" means an NH$_2$-alkyl- group in which the alkyl group is as defined herein. The group may be a terminal group or a bridging group. If the group is a terminal group it is bonded to the remainder of the molecule through the alkyl group.

"Aminosulfonyl" means an NH$_2$—S(=O)$_2$— group. The group may be a terminal group or a bridging group. If the group is a terminal group it is bonded to the remainder of the molecule through the sulfur atom.

"Aryl" as a group or part of a group denotes (i) an optionally substituted monocyclic, or fused polycyclic, aromatic carbocycle (ring structure having ring atoms that are all carbon) preferably having from 5 to 12 atoms per ring. Examples of aryl groups include phenyl, naphthyl, and the like; (ii) an optionally substituted partially saturated bicyclic aromatic carbocyclic moiety in which a phenyl and a $C_{5-7}$ cycloalkyl or $C_{5-7}$ cycloalkenyl group are fused together to form a cyclic structure, such as tetrahydronaphthyl, indenyl or indanyl. The group may be a terminal group or a bridging group. Typically an aryl group is a $C_6$-$C_{18}$ aryl group.

"Arylalkenyl" means an aryl-alkenyl- group in which the aryl and alkenyl are as defined herein. Exemplary arylalkenyl groups include phenylallyl. The group may be a terminal group or a bridging group. If the group is a terminal group it is bonded to the remainder of the molecule through the alkenyl group.

"Arylalkyl" means an aryl-alkyl- group in which the aryl and alkyl moieties are as defined herein. Preferred arylalkyl groups contain a $C_{1-5}$ alkyl moiety. Exemplary arylalkyl groups include benzyl, phenethyl, 1-naphthalenemethyl and 2-naphthalenemethyl. The group may be a terminal group or a bridging group. If the group is a terminal group it is bonded to the remainder of the molecule through the alkyl group.

"Arylalkyloxy" refers to an aryl-alkyl-O— group in which the alkyl and aryl are as defined herein. The group may be a terminal group or a bridging group. If the group is a terminal group it is bonded to the remainder of the molecule through the oxygen atom.

"Arylamino" includes both mono-arylamino and di-arylamino unless specified. Mono-arylamino means a group of formula arylNH—, in which aryl is as defined herein. di-arylamino means a group of formula (aryl)$_2$N— where each aryl may be the same or different and are each as defined herein for aryl. The group may be a terminal group or a bridging group. If the group is a terminal group it is bonded to the remainder of the molecule through the nitrogen atom.

"Arylheteroalkyl" means an aryl-heteroalkyl- group in which the aryl and heteroalkyl moieties are as defined herein. The group may be a terminal group or a bridging group. If the group is a terminal group it is bonded to the remainder of the molecule through the heteroalkyl group.

"Aryloxy" refers to an aryl-O— group in which the aryl is as defined herein. Preferably the aryloxy is a $C_6$-$C_{18}$aryloxy, more preferably a $C_6$-$C_{10}$aryloxy. The group may be a terminal group or a bridging group. If the group is a terminal group it is bonded to the remainder of the molecule through the oxygen atom.

"Arylsulfonyl" means an aryl-S(=O)$_2$— group in which the aryl group is as defined herein. The group may be a terminal group or a bridging group. If the group is a terminal group it is bonded to the remainder of the molecule through the sulfur atom.

A "bond" is a linkage between atoms in a compound or molecule. The bond may be a single bond, a double bond, or a triple bond.

"Cyclic group" refers to saturated, partially unsaturated or fully unsaturated monocyclic, bicyclic or polycyclic ring system. Examples of cyclic groups include cycloalkyl, cycloalkenyl and aryl.

"Cycloalkenyl" means a non-aromatic monocyclic or multicyclic ring system containing at least one carbon-carbon double bond and preferably having from 5-10 carbon atoms per ring. Exemplary monocyclic cycloalkenyl rings include cyclopentenyl, cyclohexenyl or cycloheptenyl. The cycloalkenyl group may be substituted by one or more substituent groups. The group may be a terminal group or a bridging group.

"Cycloalkyl" refers to a saturated monocyclic or fused or spiro polycyclic, carbocycle preferably containing from 3 to 9 carbons per ring, such as cyclopropyl, cyclobutyl, cyclopentyl, cyclohexyl and the like, unless otherwise specified. It includes monocyclic systems such as cyclopropyl and cyclohexyl, bicyclic systems such as decalin, and polycyclic systems such as adamantane. The group may be a terminal group or a bridging group.

"Cycloalkylalkyl" means a cycloalkyl-alkyl- group in which the cycloalkyl and alkyl moieties are as defined herein. Exemplary monocycloalkylalkyl groups include cyclopropylmethyl, cyclopentylmethyl, cyclohexylmethyl and cycloheptylmethyl. The group may be a terminal group or a bridging group. If the group is a terminal group it is bonded to the remainder of the molecule through the alkyl group.

"Cycloalkylalkenyl" means a cycloalkyl-alkenyl- group in which the cycloalkyl and alkenyl moieties are as defined herein. The group may be a terminal group or a bridging group. If the group is a terminal group it is bonded to the remainder of the molecule through the alkenyl group.

"Cycloalkylheteroalkyl" means a cycloalkyl-heteroalkyl-group in which the cycloalkyl and heteroalkyl moieties are as defined herein. The group may be a terminal group or a bridging group. If the group is a terminal group it is bonded to the remainder of the molecule through the heteroalkyl group.

"Cycloalkyloxy" refers to a cycloalkyl-O— group in which cycloalkyl is as defined herein. Preferably the cycloalkyloxy is a $C_1$-$C_6$cycloalkyloxy. Examples include, but are not limited to, cyclopropanoxy and cyclobutanoxy. The group may be a terminal group or a bridging group. If the group is a terminal group it is bonded to the remainder of the molecule through the oxygen atom.

"Cycloalkenyloxy" refers to a cycloalkenyl-O— group in which the cycloalkenyl is as defined herein. Preferably the cycloalkenyloxy is a $C_1$-$C_6$cycloalkenyloxy. The group may be a terminal group or a bridging group. If the group is a terminal group it is bonded to the remainder of the molecule through the oxygen atom.

"Haloalkyl" refers to an alkyl group as defined herein in which one or more of the hydrogen atoms has been replaced with a halogen atom selected from the group consisting of fluorine, chlorine, bromine and iodine. A haloalkyl group typically has the formula $C_nH_{(2n+1-m)}X_m$ wherein each X is independently selected from the group consisting of F, Cl, Br and I. In groups of this type n is typically from 1 to 10, more preferably from 1 to 6, most preferably 1 to 3. m is typically 1 to 6, more preferably 1 to 3. Examples of haloalkyl include fluoromethyl, difluoromethyl and trifluoromethyl.

"Haloalkenyl" refers to an alkenyl group as defined herein in which one or more of the hydrogen atoms has been replaced with a halogen atom independently selected from the group consisting of F, Cl, Br and I.

"Haloalkynyl" refers to an alkynyl group as defined herein in which one or more of the hydrogen atoms has been replaced with a halogen atom independently selected from the group consisting of F, Cl, Br and I.

"Halogen" represents chlorine, fluorine, bromine or iodine.

"Heteroalkyl" refers to a straight- or branched-chain alkyl group preferably having from 2 to 14 carbons, more preferably 2 to 10 carbons in the chain, one or more of which has been replaced by a heteroatom selected from S, O, P and N. Exemplary heteroalkyls include alkyl ethers, secondary and tertiary alkyl amines, amides, alkyl sulfides, and the like. The group may be a terminal group or a bridging group.

"Heteroaryl" either alone or part of a group refers to groups containing an aromatic ring (preferably a 5 or 6 membered aromatic ring) having one or more heteroatoms as ring atoms in the aromatic ring with the remainder of the ring atoms being carbon atoms. Suitable heteroatoms include nitrogen, oxygen and sulphur. Examples of heteroaryl include thiophene, benzothiophene, benzofuran, benzimidazole, benzoxazole, benzothiazole, benzisothiazole, naphtho[2,3-b]thiophene, furan, isoindolizine, xantholene, phenoxatine, pyrrole, imidazole, pyrazole, pyridine, pyrazine, pyrimidine, pyridazine, tetrazole, indole, isoindole, 1H-indazole, purine, quinoline, isoquinoline, phthalazine, naphthyridine, quinoxaline, cinnoline, carbazole, phenanthridine, acridine, phenazine, thiazole, isothiazole, phenothiazine, oxazole, isooxazole, furazane, phenoxazine, 2-, 3- or 4-pyridyl, 2-, 3-, 4-, 5-, or 8-quinolyl, 1-, 3-, 4-, or 5-isoquinolinyl 1-, 2-, or 3-indolyl, and 2-, or 3-thienyl. The group may be a terminal group or a bridging group.

"Heteroarylalkyl" means a heteroaryl-alkyl group in which the heteroaryl and alkyl moieties are as defined herein. Preferred heteroarylalkyl groups contain a lower alkyl moiety. Exemplary heteroarylalkyl groups include pyridylmethyl. The group may be a terminal group or a bridging group. If the group is a terminal group it is bonded to the remainder of the molecule through the alkyl group.

"Heteroarylalkenyl" means a heteroaryl-alkenyl- group in which the heteroaryl and alkenyl moieties are as defined herein. The group may be a terminal group or a bridging group. If the group is a terminal group it is bonded to the remainder of the molecule through the alkenyl group.

"Heteroarylheteroalkyl" means a heteroaryl-heteroalkyl-group in which the heteroaryl and heteroalkyl moieties are as defined herein. The group may be a terminal group or a bridging group. If the group is a terminal group it is bonded to the remainder of the molecule through the heteroalkyl group.

"Heteroaryloxy" refers to a heteroaryl-O— group in which the heteroaryl is as defined herein. Preferably the heteroaryloxy is a $C_1$-$C_{12}$heteroaryloxy. The group may be a terminal group or a bridging group. If the group is a terminal group it is bonded to the remainder of the molecule through the oxygen atom.

"Heterocyclic" refers to saturated, partially unsaturated or fully unsaturated monocyclic, bicyclic or polycyclic ring system containing at least one heteroatom selected from the group consisting of nitrogen, sulfur and oxygen as a ring atom. Examples of heterocyclic moieties include heterocycloalkyl, heterocycloalkenyl and heteroaryl.

"Heterocycloalkenyl" refers to a heterocycloalkyl as defined herein but containing at least one double bond. The group may be a terminal group or a bridging group.

"Heterocycloalkyl" refers to a saturated monocyclic, bicyclic, or polycyclic ring containing at least one heteroatom selected from nitrogen, sulfur, oxygen, preferably from 1 to 3 heteroatoms in at least one ring. Each ring is preferably from 3 to 10 membered, more preferably 4 to 7 membered. Examples of suitable heterocycloalkyl substituents include pyrrolidyl, tetrahydrofuryl, tetrahydrothiofuranyl, piperidyl, piperazyl, tetrahydropyranyl, morphilino, 1,3-diazapane, 1,4-diazapane, 1,4-oxazepane, and 1,4-oxathiapane. The group may be a terminal group or a bridging group.

"Heterocycloalkylalkyl" refers to a heterocycloalkyl-alkyl- group in which the heterocycloalkyl and alkyl moieties are as defined herein. Exemplary heterocycloalkylalkyl groups include (2-tetrahydrofuryl)methyl, (2-tetrahydrothiofuranyl)methyl. The group may be a terminal group or a bridging group. If the group is a terminal group it is bonded to the remainder of the molecule through the alkyl group.

"Heterocycloalkylalkenyl" refers to a heterocycloalkyl-alkenyl- group in which the heterocycloalkyl and alkenyl moieties are as defined herein. The group may be a terminal group or a bridging group. If the group is a terminal group it is bonded to the remainder of the molecule through the alkenyl group.

"Heterocycloalkylheteroalkyl" means a heterocycloalkyl-heteroalkyl- group in which the heterocycloalkyl and heteroalkyl moieties are as defined herein. The group may be a terminal group or a bridging group. If the group is a terminal group it is bonded to the remainder of the molecule through the heteroalkyl group.

"Heterocycloalkyloxy" refers to an heterocycloalkyl-O— group in which the heterocycloalkyl is as defined herein. Preferably the heterocycloalkyloxy is a $C_1$-$C_6$heterocycloalkyloxy. The group may be a terminal group or a bridging group. If the group is a terminal group it is bonded to the remainder of the molecule through the oxygen atom.

"Heterocycloalkenyloxy" refers to a heterocycloalkenyl-O— group in which heterocycloalkenyl is as defined herein. Preferably the heterocycloalkenyloxy is a $C_1$-$C_6$ heterocycloalkenyloxy. The group may be a terminal group or a bridging group. If the group is a terminal group it is bonded to the remainder of the molecule through the oxygen atom.

"Hydroxyalkyl" refers to an alkyl group as defined herein in which one or more of the hydrogen atoms has been replaced with an OH group. A hydroxyalkyl group typically has the formula $C_nH_{(2n+1-m)}(OH)_m$. In groups of this type n is typically from 1 to 10, more preferably from 1 to 6, most preferably 1 to 3. m is typically 1 to 6, more preferably 1 to 3.

"Lower alkyl" as a group means unless otherwise specified, an aliphatic hydrocarbon group which may be straight or branched having 1 to 6 carbon atoms in the chain, more preferably 1 to 4 carbons such as methyl, ethyl, propyl (n-propyl or isopropyl) or butyl (n-butyl, isobutyl or tertiary-butyl). The group may be a terminal group or a bridging group.

"Sulfinyl" means an R—S(=O)— group in which the R group may be OH, alkyl, cycloalkyl, heterocycloalkyl; aryl or heteroaryl group as defined herein. The group may be a terminal group or a bridging group. If the group is a terminal group it is bonded to the remainder of the molecule through the sulfur atom.

"Sulfinylamino" means an R—S(=O)—NH— group in which the R group may be OH, alkyl, cycloalkyl, heterocycloalkyl; aryl or heteroaryl group as defined herein. The group may be a terminal group or a bridging group. If the group is a terminal group it is bonded to the remainder of the molecule through the nitrogen atom.

"Sulfonyl" means an R—S(=O)$_2$— group in which the R group may be OH, alkyl, cycloalkyl, heterocycloalkyl; aryl or heteroaryl group as defined herein. The group may be a terminal group or a bridging group. If the group is a terminal group it is bonded to the remainder of the molecule through the sulfur atom.

"Sulfonylamino" means an R—S(=O)$_2$—NH— group. The group may be a terminal group or a bridging group. If the group is a terminal group it is bonded to the remainder of the molecule through the nitrogen atom.

It is understood that included in the family of compounds of Formula (I) are isomeric forms including diastereoisomers, enantiomers, tautomers, and geometrical isomers in "E" or "Z" configurational isomer or a mixture of E and Z isomers. It is also understood that some isomeric forms such as diastereomers, enantiomers, and geometrical isomers can be separated by physical and/or chemical methods and by those skilled in the art.

Some of the compounds of the disclosed embodiments may exist as single stereoisomers, racemates, and/or mixtures of enantiomers and/or diastereomers. All such single stereoisomers, racemates and mixtures thereof, are intended to be within the scope of the subject matter described and claimed.

The present invention includes all pharmaceutically acceptable isotopically-labeled compounds of formula (I) wherein one or more atoms have the same atomic number as, but an atomic mass or mass number different from, the atomic mass or mass number usually found in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labeled compounds of formula (I), for example, those incorporating a radioactive isotope, are useful in drug and/or substrate tissue distribution studies. The radioactive isotopes tritium, i.e. $^3$H, and carbon-14, i.e. $^{14}$O, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of formula (I) can generally be prepared by conventional techniques known to those skilled in the art or by processes analogous to those described in the accompanying Examples and Preparations using appropriate isotopically-labeled reagents in place of the non-labeled reagent previously employed.

Additionally, Formula (I) is intended to cover, where applicable, solvated as well as unsolvated forms of the compounds. Thus, each formula includes compounds having the indicated structure, including the hydrated as well as the non-hydrated forms.

The term "pharmaceutically acceptable salts" refers to salts that retain the desired biological activity of the above-identified compounds, and include pharmaceutically acceptable acid addition salts and base addition salts. Suitable pharmaceutically acceptable acid addition salts of compounds of Formula (I) may be prepared from an inorganic acid or from an organic acid. Examples of such inorganic acids are hydrochloric, sulfuric, and phosphoric acid. Appropriate organic acids may be selected from aliphatic, cycloaliphatic, aromatic, heterocyclic carboxylic and sulfonic classes of organic acids, examples of which are formic, acetic, propionic, succinic, glycolic, gluconic, lactic, malic, tartaric, citric, fumaric, maleic, alkyl sulfonic, arylsulfonic. Additional information on pharmaceutically acceptable salts can be found in Remington's Pharmaceutical Sciences, 19th Edition, Mack Publishing Co., Easton, Pa. 1995. In the case of agents that are solids, it is understood by those skilled in the art that the inventive compounds, agents and salts may exist in different crystalline or polymorphic forms, all of which are intended to be within the scope of the present invention and specified formulae.

"Prodrug" means a compound that undergoes conversion to a compound of formula (I) within a biological system, usually by metabolic means (e.g. by hydrolysis, reduction or oxidation). For example an ester prodrug of a compound of formula (I) containing a hydroxyl group may be convertible by hydrolysis in vivo to the parent molecule. Suitable esters of compounds of formula (I) containing a hydroxyl group, are for example acetates, citrates, lactates, tartrates, malonates, oxalates, salicylates, propionates, succinates, fumarates, maleates, methylene-bis-β-hydroxynaphthoates, gestisates, isethionates, di-p-toluoyltartrates, methanesulphonates, ethanesulphonates, benzenesulphonates, p-toluenesulphonates, cyclohexylsulphamates and quinates. As another example an ester prodrug of a compound of formula (I) containing a carboxy group may be convertible by hydrolysis in vivo to the parent molecule. (Examples of ester prodrugs are those described by F. J. Leinweber, Drug Metab. Res., 18:379, 1987). Similarly, an acyl prodrug of a compound of formula (I) containing an amino group may be convertible by hydrolysis in vivo to the parent molecule (Many examples of prodrugs for these and other functional groups, including amines, are described in Prodrugs: Challenges and Rewards (Parts 1 and 2); Ed V. Stella, R. Borchardt, M. Hageman, R. Oliyai, H. Maag and J Tilley; Springer, 2007)

As with any group of structurally related compounds which possess a particular utility, certain embodiments of variables of the compounds of the Formula (I), are particularly useful in their end use application.

In the compounds of the invention Y is a group of the formula $—(CR^9R^{10})_n—$. In one embodiment of the invention n is 1 and Y is $—CR^9R^{10}—$. In another embodiment of the invention n is 2 and Y is $—CR^9R^{10}CR^9R^{10}—$.

In one embodiment of the compounds of the invention each $R^9$ and $R^{19}$ is independently selected from H and $CH_3$. In one specific embodiment $R^9$ and $R^{19}$ are both H. Accordingly in one embodiment of the invention Y is $—CH_2—$. In another embodiment of the invention Y is $—CH_2CH_2—$. In yet an even further embodiment of the invention Y is $—C(CH_3)_2—$.

In one embodiment of the compounds of the invention $R^2$ is H or $C_1$-$C_6$ alkyl. In a specific embodiment $R^2$ is H.

In one embodiment of the compounds of the invention $R^3$ is H or $C_1$-$C_6$ alkyl. In a specific embodiment $R^3$ is H.

In one embodiment of the compounds of the invention X is selected from the group consisting of $—C(=O)—$ and $—(CR^{11}R^{12})_s—$. In one specific embodiment X is $—C(=O)—$. In one embodiment of the invention where X is $—(CR^{11}R^{12})_s—$, s is 1. In another embodiment of the invention where X is $—(CR^{11}R^{12})_s—$, s is 2. In one form of each of these embodiments $R^{11}$ and $R^{12}$ are each independently selected from the group consisting of H and $C_1$-$C_6$ alkyl. In a specific embodiment both $R^{11}$ and $R^{12}$ are H, and s is 1, such that X is $—CH_2—$.

In one embodiment of the compounds of the invention Y is $CH_2$, $R^2$ is H, $R^3$ is H, and X is $—C(=O)—$. This provides compounds of formula (II).

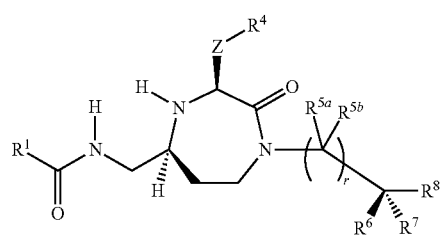

Formula (II)

wherein $R^1$, $R^4$, $R^{5a}$, $R^{5b}$, $R^6$, $R^7$, $R^8$, Z and r are as defined for formula (I).

In one embodiment of the compounds of the invention and in particular the compounds of formula (I), and formula (II) r is selected from the group consisting of 1, 2, 3, and 4. In one specific embodiment r is 1. In another specific embodiment r is 2. In yet a further specific embodiment r is 3. In an even further specific embodiment r is 4.

In one embodiment of the compounds of the invention, and in particular the compounds of formula (I), and formula (II) $R^{5a}$ and $R^{5b}$ are independently selected from H and $C_1$-$C_6$ alkyl. In one embodiment $R^{5a}$ and $R^{5b}$ are each independently selected from H and $CH_3$. In one specific embodiment $R^{5a}$ and $R^{5b}$ are both H. In yet another embodiment at least one of $R^{5a}$ and $R^{5b}$ when taken together with at least one of $R^6$, $R^7$ and $R^8$ and the atoms to which they are attached form an optionally substituted cycloalkyl group. In one specific embodiment at least one of $R^{5a}$ and $R^{5b}$ when taken together with at least one of $R^6$, $R^7$ and $R^8$ and the atoms to which they are attached forms a cyclohexyl group.

In one embodiment of the compounds of the invention, Y is $CH_2$, $R^2$ is H, $R^3$ is H, $R^{5a}$ and $R^{5b}$ are H, X is $—C(=O)—$, and r is 1. This provides compounds of formula (III).

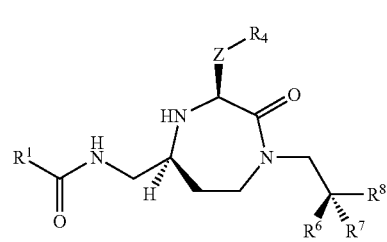

Formula (III)

wherein $R^1$, $R^4$, $R^6$, $R^7$, $R^8$ and Z are as defined for formula (I).

In one embodiment of the compounds of the invention and in particular the compounds of formula (I), (II) and (III), $R^{13}$ and $R^{14}$ are H such that Z is a group of formula $—(CH_2)_q—$, where q is as defined above.

In one embodiment of the compounds of the invention q is an integer selected from the group consisting of 1, 2, 3, and 4. In one specific embodiment q is 1. In another specific embodiment q is 2, and in yet an even further specific embodiment q is 3. In yet an even further specific embodiment q is 4. This provides compounds where Z is $—CH_2—$, $—(CH_2)_2—$, $—(CH_2)_3—$ and $—(CH_2)_4—$ respectively.

In one embodiment of the compounds of the invention and in particular the compounds of formula (I), (II) and (III), $R^4$ is selected from the group consisting of H, $C_1$-$C_{12}$alkyl, $C_3$-$C_{12}$cycloalkyl, optionally substituted $C_6$-$C_{18}$aryl, optionally substituted C-linked $C_1$-$C_{18}$heteroaryl, $C(=O)NR^{16}R^{17}$, $OR^{16}$, and $ONR^{16}C(=NR^{17})NR^{18}R^{19}$.

In one embodiment $R^4$ is $C_1$-$C_{12}$ alkyl.

In another embodiment $R^4$ is $C(=O)NR^{16}R^{17}$.

In one form of this specific embodiment where $R^4$ is $C(=O)NR^{16}R^{17}$, $R^{16}$ and $R^{17}$ when taken together with the nitrogen atom to which they are attached form an optionally substituted $C_2$-$C_{12}$heterocycloalkyl group. In specific embodiments $R^{16}$ and $R^{17}$ when taken together with the nitrogen atom to which they are attached form an optionally substituted heterocycloalkyl group selected from the group consisting of piperidin-1-yl, piperidin-4-yl, pyrrolidin-1-yl, pyrrolidin-2-yl azetidin-1-yl, cyclohexane, morpholin-4-yl, piperazin-1-yl, 4-methyl-piperazin-1-yl and azepan-1-yl.

In another specific embodiment $R^4$ is optionally substituted C-linked $C_1$-$C_{18}$heteroaryl. In another specific embodiment $R^4$ is $C_3$-$C_{12}$cycloalkyl.

In one embodiment of the compounds of the invention $R^{16}$ is selected from the group consisting of H, $CH_3$, $CH_2CH_3$, $CH_2CH_2CH_3$, $CH(CH_3)_2$, $CH_2CH_2CH_2CH_3$, $CH(CH_3)CH_2CH_3$, $CH_2CH(CH_3)_2$, $C(CH_3)_3$, cyclopropyl, cyclobutyl, cyclopentyl, cyclohexyl, benzyl, and phenyl, or a halogenated derivative thereof.

In one embodiment of the compounds of the invention $R^{17}$ is selected from the group consisting of H, $CH_3$, $CH_2CH_3$, $CH_2CH_2CH_3$, $CH(CH_3)_2$, $CH_2CH_2CH_2CH_3$, $CH(CH_3)CH_2CH_3$, $CH_2CH(CH_3)_2$, $C(CH_3)_3$, cyclopropyl, cyclobutyl, cyclopentyl, cyclohexyl, benzyl, and phenyl, or a halogenated derivative thereof.

In one embodiment of the compounds of the invention, and specifically of the compounds of formula (I), (II) and (III), $R^7$ is H.

In one embodiment of the invention, and specifically of the compounds of formula (I), (II) and (III), $R^6$ and $R^8$ are each independently selected from the group consisting of H, optionally substituted $C_1$-$C_{12}$ alkyl, optionally substituted $C_2$-$C_{12}$ alkenyl, optionally substituted $C_6$-$C_{18}$ aryl and optionally substituted $C_1$-$C_{18}$heteroaryl.

In one embodiment of the invention, and specifically of the compounds of formula (I), (II) and (III), $R^6$ and $R^8$ are each independently selected from the group consisting of optionally substituted $C_1$-$C_{12}$ alkyl, optionally substituted $C_2$-$C_{12}$ alkenyl, optionally substituted $C_6$-$C_{18}$ aryl and optionally substituted $C_1$-$C_{18}$heteroaryl.

In one embodiment of the invention, and specifically of the compounds of formula (I), (II) and (III), $R^6$ and $R^8$ are each independently selected from the group consisting of optionally substituted $C_2$-$C_{12}$ alkyl, optionally substituted $C_2$-$C_{12}$ alkenyl, optionally substituted $C_6$-$C_{18}$ aryl and optionally substituted $C_1$-$C_{18}$heteroaryl.

In one specific embodiment of the compounds of the invention, and specifically of the compounds of formula (I), (II) and (III), $R^6$ is selected from the group consisting of H, methyl, trifluoromethyl, ethyl, 2,2,2-trifluoroethyl, isopropyl, isopropenyl, propyl, 2-ethyl-propyl, 3,3-dimethyl-propyl, butyl, 2-methyl-butyl, isobutyl, 3,3-dimethyl-butyl, 2-ethyl-butyl, pentyl, 2-methyl-pentyl, optionally substituted phenyl and optionally substituted $C_1$-$C_5$ heteroaryl.

In one specific embodiment of the compounds of the invention and specifically of the compounds of formula (I), (II) and (III), $R^6$ is optionally substituted phenyl or optionally substituted $C_1$-$C_{18}$heteroaryl.

In one specific embodiment of the compounds of the invention and specifically of the compounds of formula (I), (II) and (III), $R^8$ is selected from the group consisting of H, methyl, trifluoromethyl, ethyl, 2,2,2-trifluoroethyl, isopropyl, isopropenyl, propyl, 2-ethyl-propyl, 3,3-dimethyl-propyl, butyl, 2-methyl-butyl, isobutyl, 3,3-dimethyl-butyl, 2-ethyl-butyl, pentyl, 2-methyl-pentyl, optionally substituted phenyl and optionally substituted $C_1$-$C_5$ heteroaryl.

In one specific embodiment of the compounds of the invention and specifically of the compounds of formula (I), (II) and (III), $R^8$ is methyl, ethyl, phenyl or optionally substituted $C_1$-$C_5$ heteroaryl.

In one specific embodiment of the compounds of the invention and specifically of the compounds of formula (I), (II) and (III), $R^6$, $R^7$ and $R^8$ when taken together with the carbon atom to which they are attached form a moiety selected from the group consisting of optionally substituted $C_2$-$C_{12}$alkenyl, optionally substituted $C_3$-$C_{12}$cycloalkyl, optionally substituted $C_2$-$C_{12}$heterocycloalkyl, optionally substituted $C_6$-$C_{18}$aryl, and optionally substituted $C_1$-$C_{18}$heteroaryl.

In one specific embodiment of the compounds of the invention and specifically of the compounds of formula (I), (II) and (III), $R^6$, $R^7$ and $R^8$ when taken together with the carbon atom to which they are attached form an optionally substituted $C_6$-$C_{18}$aryl group.

In one specific embodiment of the compounds of the invention and specifically of the compounds of formula (I), (II) and (III), $R^6$, $R^7$ and $R^8$ when taken together with the carbon atom to which they are attached form a disubstituted phenyl group. In one embodiment the disubstituted phenyl group is a 2,4-disubstituted phen-1-yl group or a 3,5-disubstituted phen-1-yl group. A wide variety of substituents may be present on the disubstituted phenyl group as defined above. Examples of particularly suitable substituents include, but are not limited to F, Br, Cl, methyl, trifluoromethyl, ethyl, 2,2,2-trifluoroethyl, isopropyl, propyl, 2-ethyl-propyl, 3,3-dimethyl-propyl, butyl, isobutyl, 3,3-dimethyl-butyl, 2-ethyl-butyl, pentyl, 2-methyl-pentyl, pent-4-enyl, hexyl, heptyl, octyl, phenyl, $NH_2$, cyano, phenoxy, hydroxy, methoxy, ethoxy, methylenedioxy, pyrrol-1-yl, and 3,5-dimethyl-pyrazol-1-yl. In one specific embodiment the disubstituted phenyl group is a dichlorophen-1-yl group.

In one embodiment of the compounds of the invention and specifically of the compounds of formula (I), (II) and (III), $R^1$ is selected from the group consisting of optionally substituted $C_2$-$C_{12}$alkenyl, optionally substituted $C_6$-$C_{18}$aryl and optionally substituted $C_1$-$C_{18}$heteroaryl.

In one embodiment of the compounds of the invention and specifically of the compounds of formula (I), (II) and (III), $R^1$ is optionally substituted $C_6$-$C_{18}$aryl. The $C_6$-$C_{18}$aryl may be a monocyclic, bicyclic or polycyclic moiety. In certain embodiments the $C_6$-$C_{18}$aryl is a monocyclic moiety. In certain embodiments the $C_6$-$C_{18}$aryl is a bicyclic moiety.

In one specific embodiment $R^1$ is an optionally substituted $C_6$-$C_{18}$aryl selected from the group consisting of optionally substituted phenyl, biphenyl, and optionally substituted naphthyl. The moieties may be unsubstituted or may be substituted with one or more optional substituents. A wide variety of optional substituents may be used as defined above. Examples of particularly suitable optional substituents include, but are not limited to, F, Br, Cl, methyl, trifluoromethyl, ethyl, 2,2,2-trifluoroethyl, isopropyl, propyl, 2-ethyl-propyl, 3,3-dimethyl-propyl, butyl, isobutyl, 3,3-dimethyl-butyl, 2-ethyl-butyl, pentyl, 2-methyl-pentyl, pent-4-enyl, hexyl, heptyl, octyl, phenyl, $NH_2$, cyano, phenoxy, hydroxy, methoxy, ethoxy, pyrrol-1-yl, and 3,5-dimethyl-pyrazol-1-yl.

The substituents may be located at any substitutable position around the aryl ring available for substitution as would be clear to a skilled addressee. Examples of suitable optionally substituted phenyl compounds include, but are not limited to, 2-methoxy-phenyl, 3-methoxy-phenyl, 4-methoxy-phenyl, 2-trifluoromethyl-phenyl, 3-trifluoromethyl-phenyl, 4-trifluoromethyl-phenyl, 2-chloro-phenyl, 3-chloro-phenyl, 4-chloro-phenyl, 4-bromo-phenyl, 2-fluoro-phenyl, 3-fluoro-phenyl, 4-fluoro-phenyl, 4-hydroxy-phenyl, 4-phenyl-phenyl, 4-methyl-phenyl, 2,4-dichloro-phenyl, 3,4-dichloro-phenyl, 2,5-dichloro-phenyl, 2,6-difluoro-phenyl, 2-chloro-6-fluoro-phenyl, 3-fluoro-4-chloro-phenyl, 3-methyl-4-chloro-phenyl, 3-chloro-4-fluoro-phenyl, 3-chloro-4-methyl-phenyl, 2-hydroxy-phenyl, 3-hydroxy-phenyl, 4-hydroxy-phenyl, 4-ethoxy-phenyl, 3-phenoxy-phenyl, 4-phenoxy-phenyl, 2-methyl-phenyl, 3-methyl-phenyl, 4-methyl-phenyl, 4-isopropyl-phenyl, 4-cyano-phenyl, 3,4-dimethyl-phenyl, 2,4-dimethyl-phenyl, 4-t-butyl-phenyl, 2,4-dimethoxy-phenyl, and 3,4-methylenedioxy-phenyl.

When $R^1$ is optionally substituted biphenyl the point of attachment of $R^1$ to the remainder of the molecule may be at the 2-, 3- or 4-position relative to the point of attachment of the second phenyl ring. As such the biphenyl may be an optionally substituted biphen-2-yl, or an optionally substituted biphen-3-yl, or an optionally substituted biphen-4-yl. In general the optionally substituted biphenyl is an optionally substituted biphen-4-yl. The optionally substituted biphenyl may be substituted in any suitable position.

When $R^1$ is optionally substituted naphthyl the point of attachment of $R^1$ to the remainder of the molecule may be at the 1 or 2 position. As such the naphthyl may be an optionally substituted naphth-1-yl, or an optionally substituted naphth-2-yl. In general the optionally substituted naphthyl is an optionally substituted naphth-2-yl. The optionally substituted naphthyl may be substituted in any suitable position. Examples of suitable optionally substituted naphth-2-yls include, but are not limited to, 6-fluoro-naphth-2-yl, 6-bromo-naphth-2-yl, 6-chloro-naphth-2-yl, 1-methoxy-naphth-2-yl, 3-methoxy-naphth-2-yl, 6-methoxy-naphth-2-yl, 1-hydroxy-naphth-2-yl, and 6-amino-naphth-2-yl.

In one embodiment of the compounds of the invention and specifically of the compounds of formula (I), (II) and (III), $R^1$ is optionally substituted $C_1$-$C_{18}$heteroaryl. The $C_1$-$C_{18}$heteroaryl may be a monocyclic, bicyclic or polycyclic moiety. In certain embodiments the $C_1$-$C_{18}$heteroaryl is a monocyclic moiety. In certain embodiments the $C_1$-$C_{18}$heteroaryl is a bicyclic moiety. Examples of suitable heteroaryl moieties include, but are not limited to, indol-2-yl, indol-3-yl quinolin-2-yl quinolin-3-yl, isoquinolin-3-yl, quinoxaline-2-yl, benzo[b]furan-2-yl, benzo[b]thiophen-2-yl, benzo[b]thiophen-5-yl, thiazole-4-yl, benzimidazole-5-yl, benzotriazol-5-yl, furan-2-yl, benzo[d]thiazole-6-yl, pyrazole-1-yl, pyrazole-4-yl and thiophen-2-yl. These may also be optionally substituted as discussed above.

In one embodiment of the compounds of the invention and specifically of the compounds of formula (I), (II) and (III), $R^1$ is an optionally substituted $C_2$-$C_{12}$alkenyl. The optionally substituted alkenyl may contain one or more double bonds with each of the double bonds being independently in the E or Z configuration. In one embodiment of the invention the alkenyl contains a single double bond which is in the E configuration.

In one specific form of this embodiment $R^1$ is an optionally substituted $C_2$-$C_{12}$alkenyl of the formula:

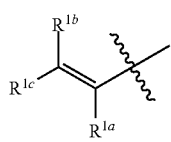

$R^{1a}$ is selected from the group consisting of H, halogen and optionally substituted $C_1$-$C_{12}$ alkyl;

$R^{1b}$ and $R^{1c}$ are each independently selected from the group consisting of H, halogen, optionally substituted $C_1$-$C_{12}$alkyl, optionally substituted $C_2$-$C_{12}$alkenyl, optionally substituted $C_2$-$C_{12}$alkynyl, optionally substituted $C_1$-$C_{12}$heteroalkyl, optionally substituted $C_3$-$C_{12}$cycloalkyl, optionally substituted $C_2$-$C_{12}$ heterocycloalkyl, optionally substituted $C_6$-$C_{18}$aryl, and optionally substituted $C_1$-$C_{18}$heteroaryl.

In one form of this embodiment $R^{1a}$ is H. In one form of this embodiment $R^{1b}$ is H. This provides compounds where $R^1$ is of the formula:

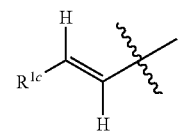

In one embodiment of the compounds of the invention $R^1$ is optionally substituted $C_6$-$C_{18}$aryl. The $C_6$-$C_{18}$aryl may be monocyclic, bicyclic or polycyclic moiety. In certain embodiments the $C_6$-$C_{18}$aryl is a monocyclic moiety. In certain embodiments the $C_6$-$C_{18}$aryl is a bicyclic moiety.

In one specific embodiment $R^{1c}$ is an optionally substituted $C_6$-$C_{18}$aryl selected from the group consisting of optionally substituted phenyl and optionally substituted naphthyl. The moieties may be unsubstituted or may be substituted with one or more optional substituents. A wide variety of optional substituents may be used as defined above. Examples of particularly suitable optional substituents include, but are not limited to, F, Br, Cl, methyl, trifluoromethyl, ethyl, 2,2,2-trifluoroethyl, isopropyl, propyl, 2-ethyl-propyl, 3,3-dimethyl-propyl, butyl, isobutyl, 3,3-dimethyl-butyl, 2-ethyl-butyl, pentyl, 2-methyl-pentyl, pent-4-enyl, hexyl, heptyl, octyl, phenyl, $NH_2$, cyano, phenoxy, hydroxy, methoxy, ethoxy, methylenedioxy, pyrrol-1-yl, and 3,5-dimethyl-pyrazol-1-yl.

The substituents may be located at any substitutable position around the aryl ring available for substitution as would be clear to a skilled addressee. Examples of suitable optionally substituted phenyl compounds include, but are not limited to, 2-methoxy-phenyl, 3-methoxy-phenyl, 4-methoxy-phenyl, 2-trifluoromethyl-phenyl, 3-trifluoromethyl-phenyl 4-trifluoromethyl-phenyl 2-chloro-phenyl, 3-chloro-phenyl, 4-chloro-phenyl, 4-bromo-phenyl, 2-fluoro-phenyl 3-fluoro-phenyl, 4-fluoro-phenyl, 4-hydroxy-phenyl 4-phenyl-phenyl, 4-methyl-phenyl, 2,4-dichloro-phenyl, 3,4-dichloro-phenyl, 2,5-dichloro-phenyl, 2,6-difluoro-phenyl, 2-chloro-6-fluoro-phenyl, 3-fluoro-4-chloro-phenyl, 3-methyl-4-chloro-phenyl, 3-chloro-4-fluoro-phenyl, 3-chloro-4-methyl-phenyl, 2-hydroxy-phenyl 3-hydroxy-phenyl 4-hydroxy-phenyl, 4-ethoxy-phenyl, 3-phenoxy-phenyl, 4-phenoxy-phenyl, 2-methyl-phenyl, 3-methyl-phenyl, 4-methyl-phenyl, 4-isopropyl-phenyl, 4-cyano-phenyl 3,4-dimethyl-phenyl, 2,4-dimethyl-phenyl, 4-t-butyl-phenyl, 2,4-dimethoxy-phenyl, and 3,4-methylenedioxy-phenyl.

Specific compounds of the invention include the following:
(46)
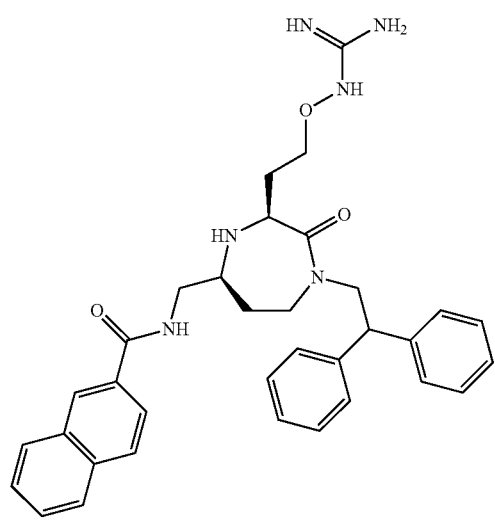
(47)
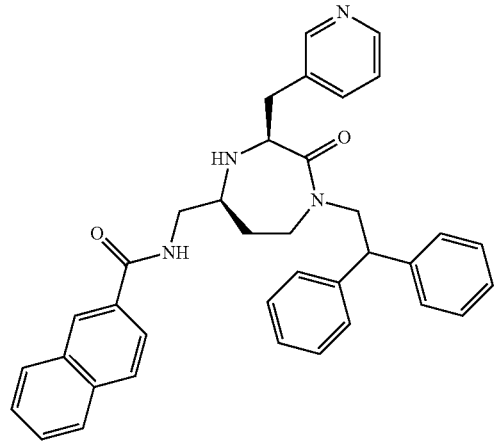
(48)
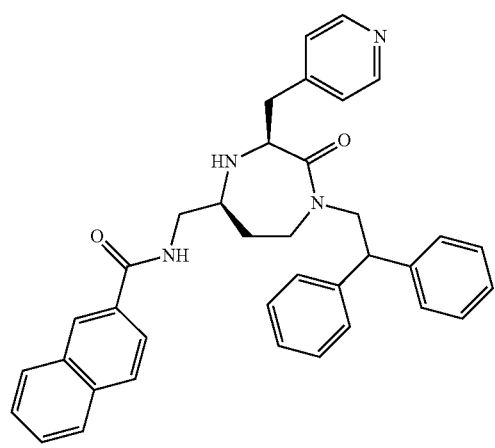
(49)
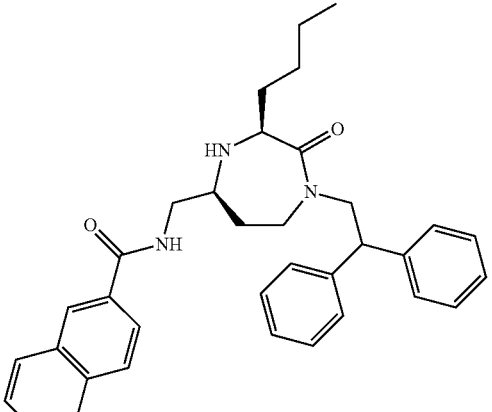
(50)
(51)
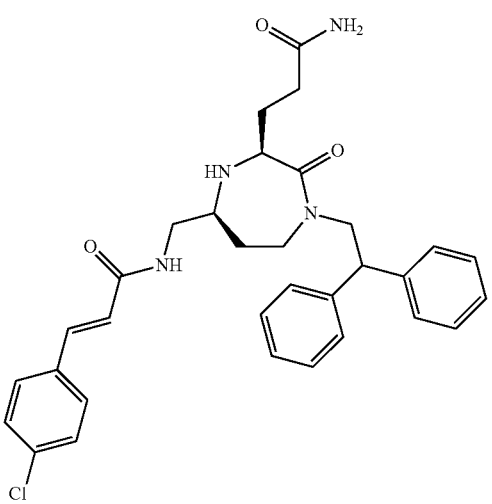

(52) 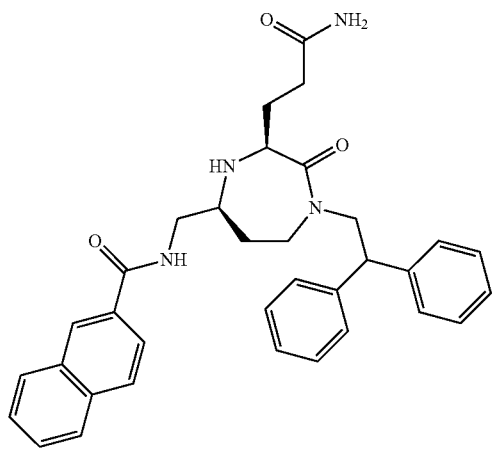
(53) 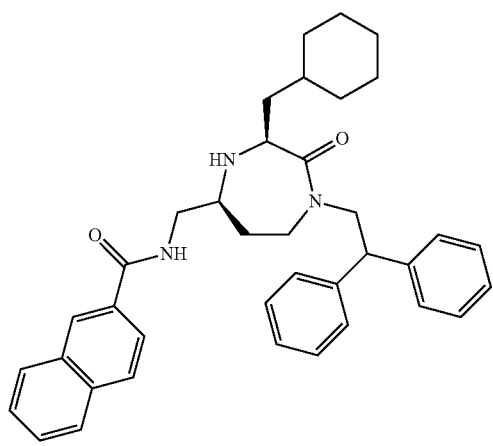
(54) 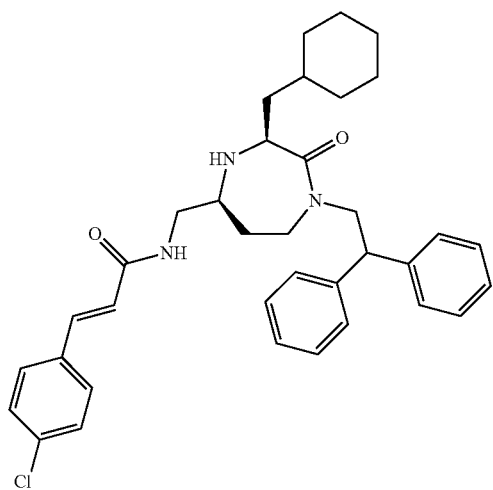
(55) 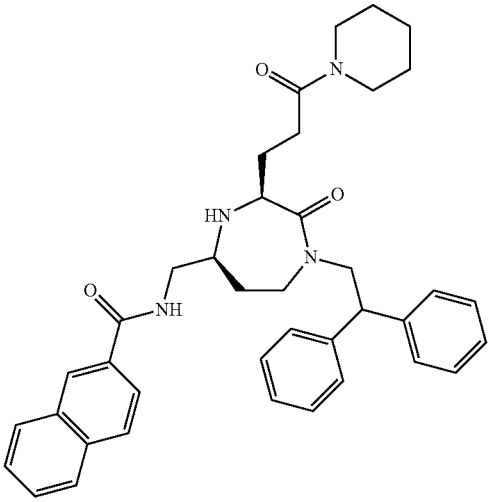
(56) 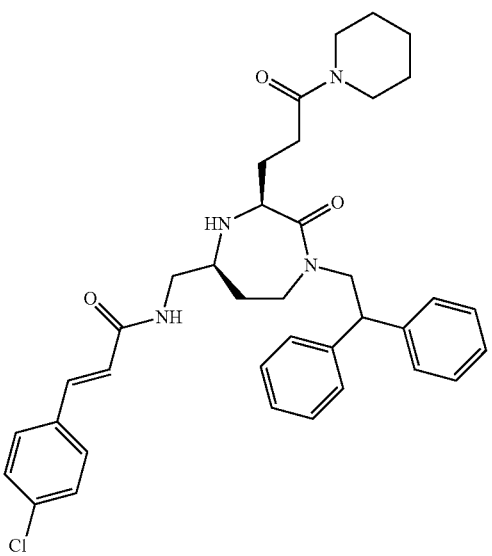
(57) 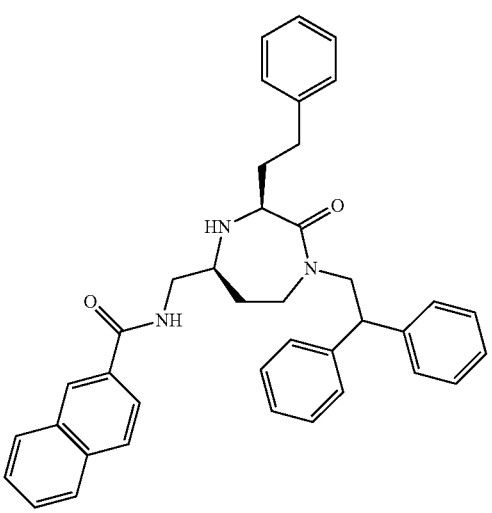

(58)
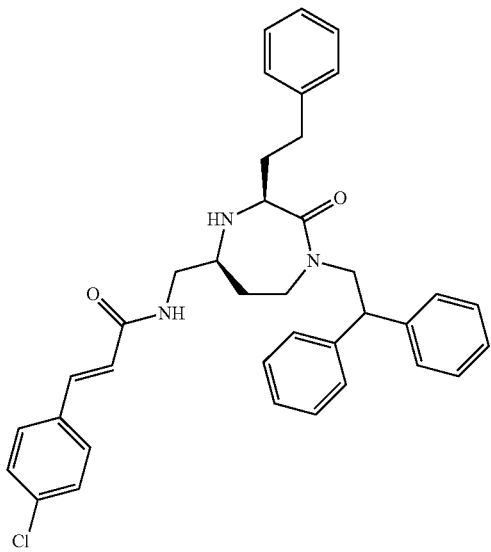
(59)
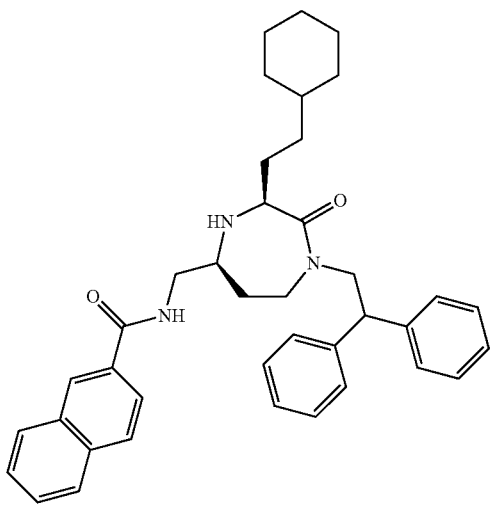
(60)
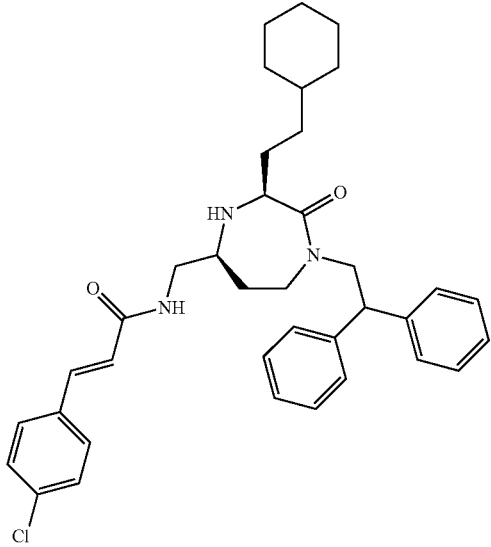
(61)
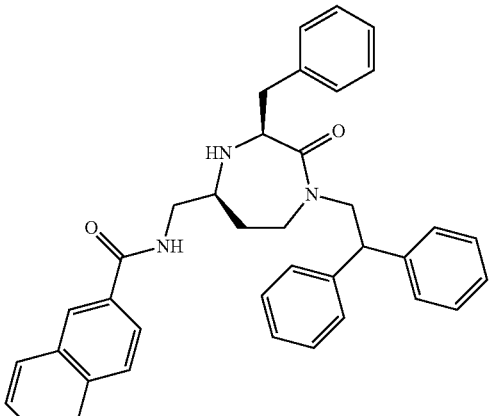
(62)
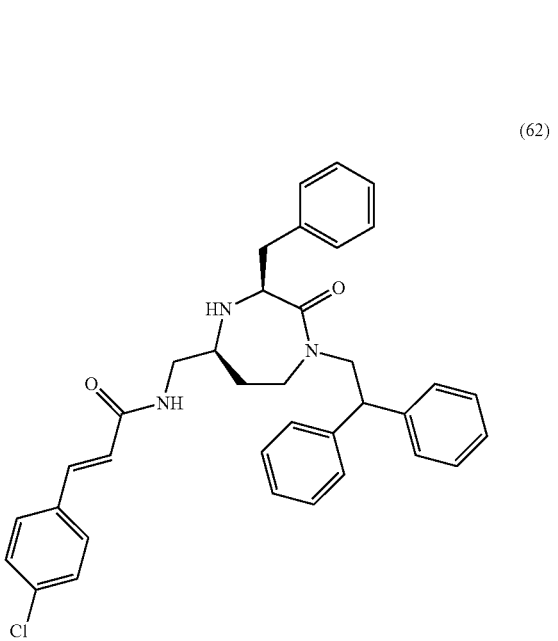
(63)
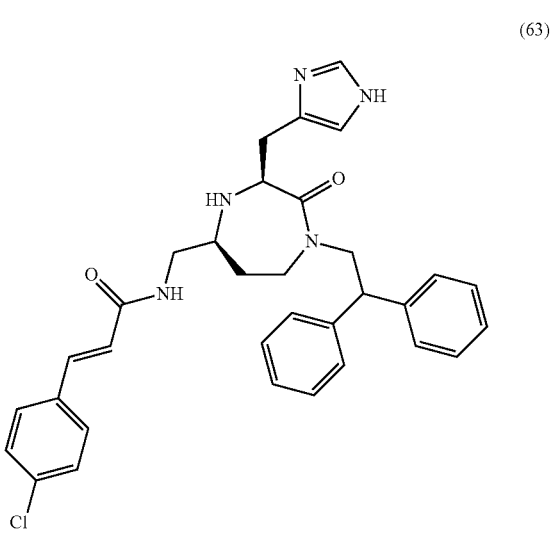

(45)
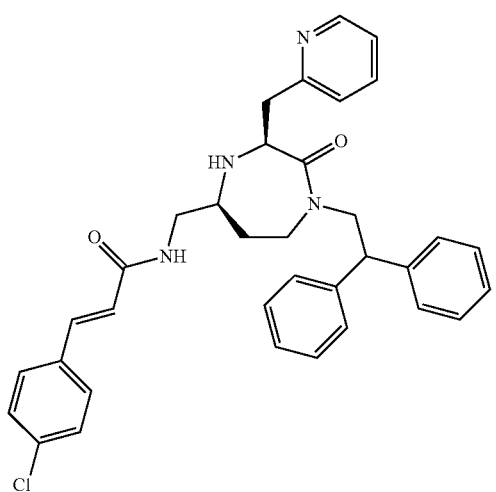
(64)
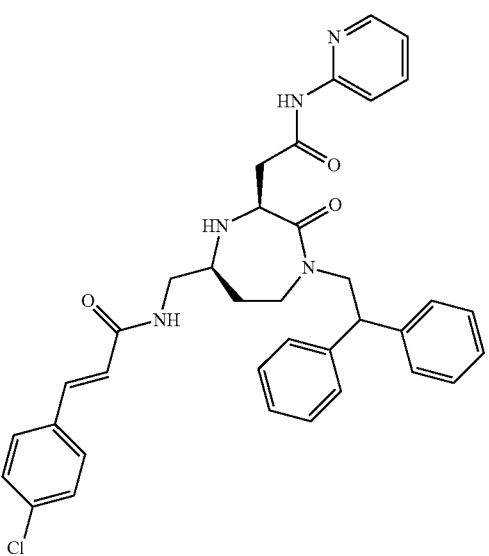
(65)
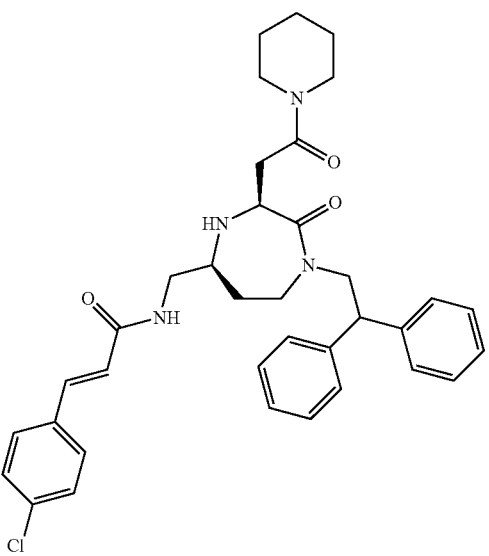
(66)
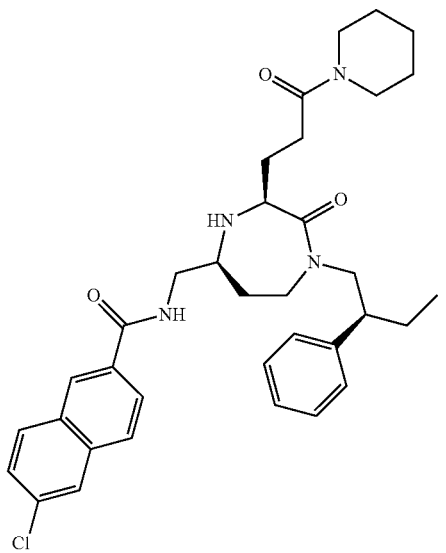
(67)
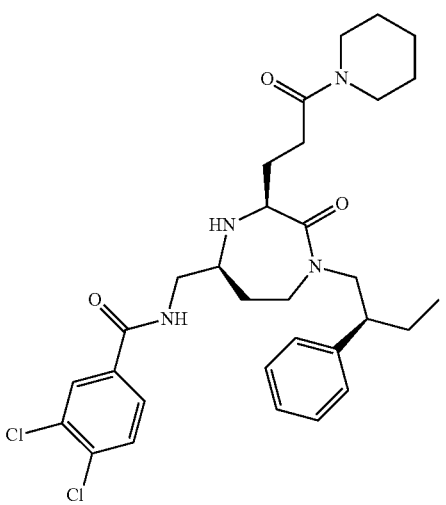
(68)
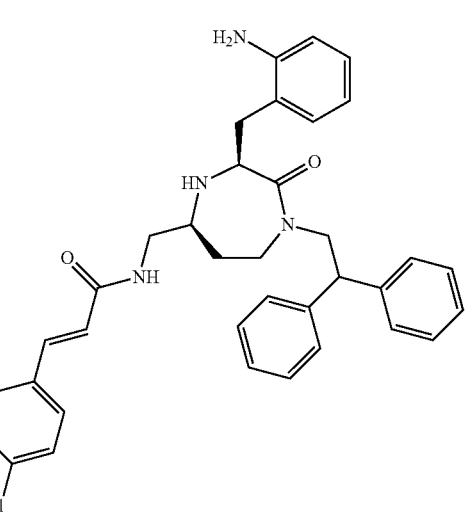

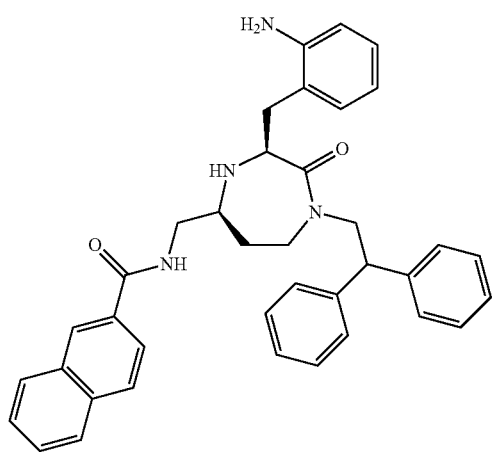
(69)
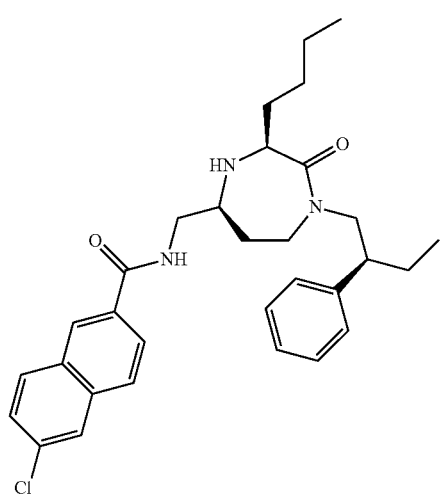
(70)
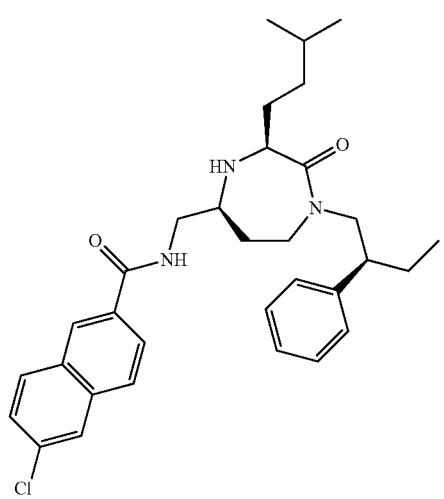
(17)
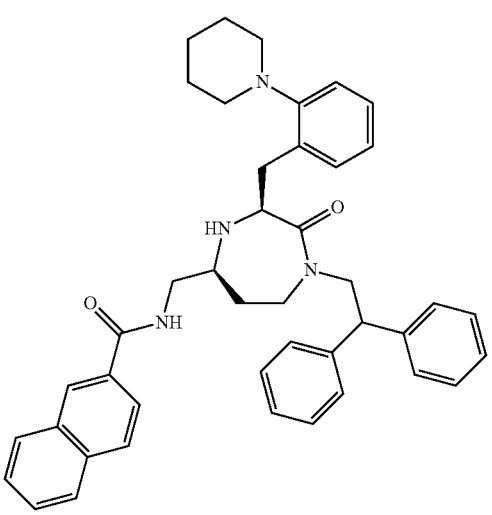
(71)
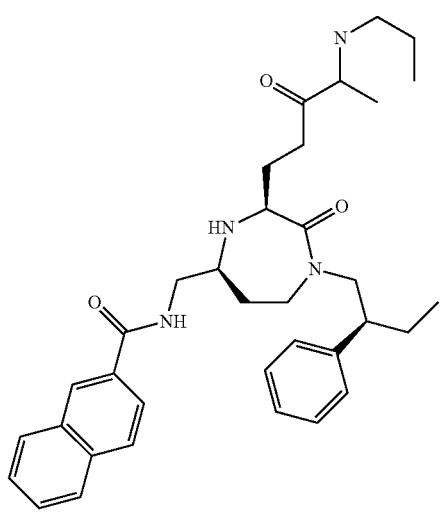
(72)
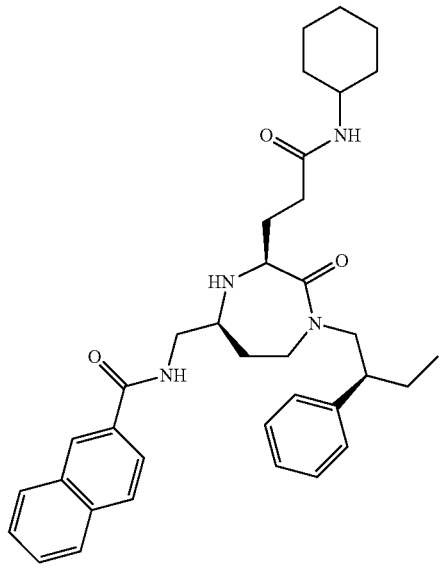
(73)

(74)
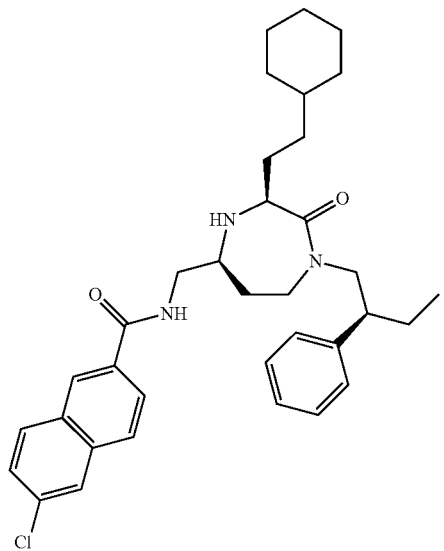
(75)
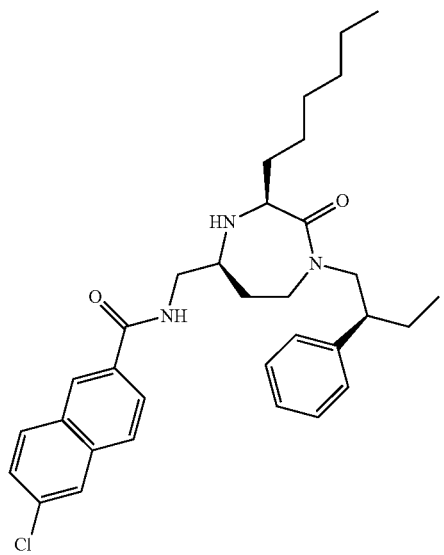
(76)
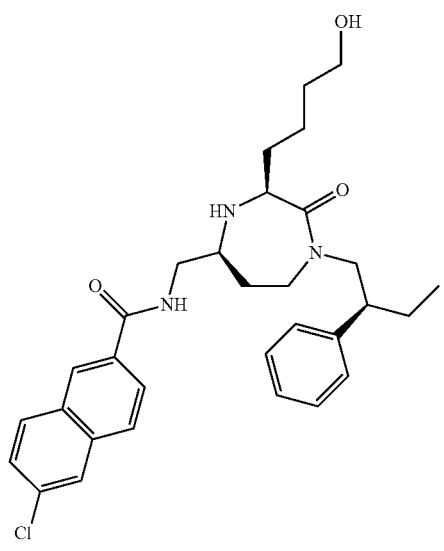
(77)
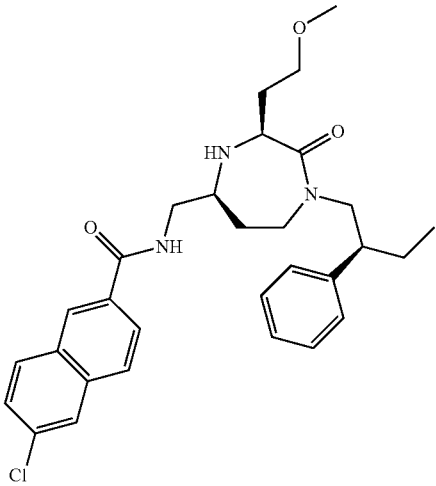
(78)
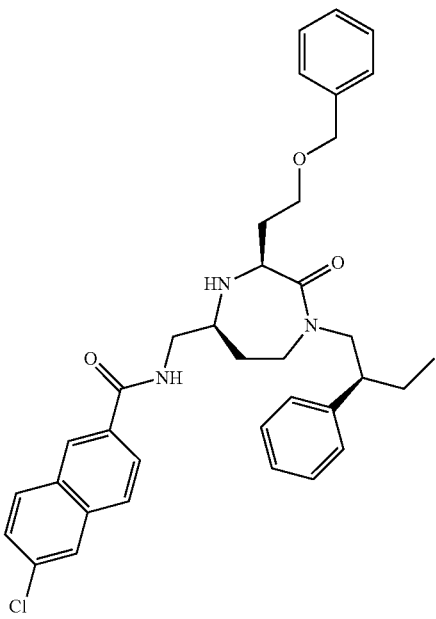
(79)
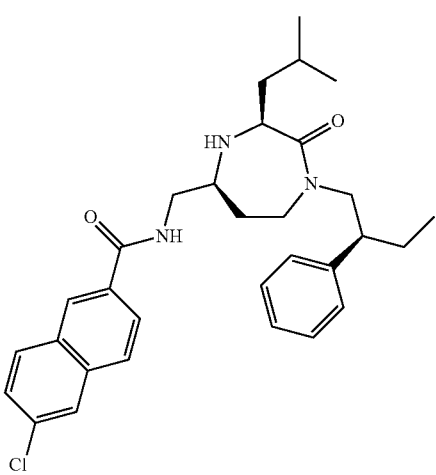

(80)

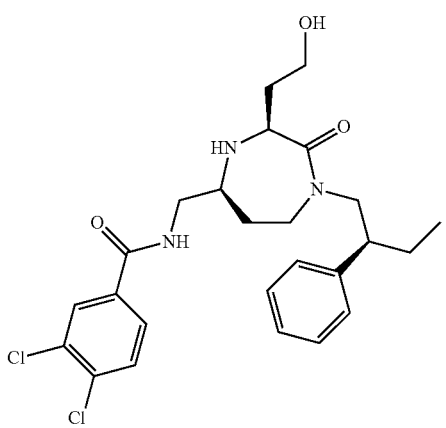

or a pharmaceutically acceptable salt or prodrug thereof.

In order to assist the reader the names of the compounds of the invention as discussed above are as follows:

(17) 6-chloro-N-(((3S,5S)-3-isopentyl-2-oxo-1-((S)-2-phenylbutyl)-1,4-diazepan-5-yl)methyl)-2-naphthamide diazepan-5-yl)methyl)-3-(4-chlorophenyl)acrylamide

(45) (E)-3-(4-chlorophenyl)-N-(((3S,5S)-1-(2,2-diphenylethyl)-2-oxo-3-(pyridin-2-ylmethyl)-1,4-diazepan-5-yl)methyl)acrylamide

(46) N-(((3S,5S)-1-(2,2-diphenylethyl)-3-(2-(guanidinooxy)ethyl)-2-oxo-1,4-diazepan-5-yl)methyl)-2-naphthamide

(47) N-(((3S,5S)-1-(2,2-diphenylethyl)-2-oxo-3-(pyridin-3-ylmethyl)-1,4-diazepan-5-yl)methyl)-2-naphthamide

(48) N-(((3S,5S)-1-(2,2-diphenylethyl)-2-oxo-3-(pyridin-4-ylmethyl)-1,4-diazepan-5-yl)methyl)-2-naphthamide

(49) N-(((3S,5S)-3-butyl-1-(2,2-diphenylethyl)-2-oxo-1,4-diazepan-5-yl)methyl)-2-naphthamide

(50) (E)-N-(((3S,5S)-3-butyl-1-(2,2-diphenylethyl)-2-oxo-1,4-diazepan-5-yl)methyl)-3-(4-chlorophenyl)acrylamide

(51) (E)-N-(((3S,5S)-3-(3-amino-3-oxopropyl)-1-(2,2-diphenylethyl)-2-oxo-1,4-diazepan-5-yl)methyl)-3-(4-chlorophenyl)acrylamide

(52) N-(((3S,5S)-3-(3-amino-3-oxopropyl)-1-(2,2-diphenylethyl)-2-oxo-1,4-diazepan-5-yl)methyl)-2-naphthamide

(53) N-(((3S,5S)-3-(cyclohexylmethyl)-1-(2,2-diphenylethyl)-2-oxo-1,4-diazepan-5-yl)methyl)-2-naphthamide

(54) N-(((3S,5S)-3-(2-aminoethyl)-1-(3,5-dichlorobenzyl)-2-oxo-1,4-diazepan-5-yl)methyl)-2-naphthamide

(55) N-(((3S,5S)-1-(2,2-diphenylethyl)-2-oxo-3-(3-oxo-3-(piperidin-1-yl)propyl)-1,4-diazepan-5-yl)methyl)-2-naphthamide

(56) (E)-3-(4-chlorophenyl)-N-(((3S,5S)-1-(2,2-diphenylethyl)-2-oxo-3-(3-oxo-3-(piperidin-1-yl)propyl)-1,4-diazepan-5-yl)methyl)acrylamide

(57) N-(((3S,5S)-1-(2,2-diphenylethyl)-2-oxo-3-phenethyl-1,4-diazepan-5-yl)methyl)-2-naphthamide

(58) (E)-3-(4-chlorophenyl)-N-(((3S,5S)-1-(2,2-diphenylethyl)-2-oxo-3-phenethyl-1,4-diazepan-5-yl)methyl)acrylamide

(59) N-(((3S,5S)-3-(2-cyclohexylethyl)-1-(2,2-diphenylethyl)-2-oxo-1,4-diazepan-5-yl)methyl)-2-naphthamide

(60) (E)-3-(4-chlorophenyl)-N-(((3S,5S)-3-(2-cyclohexylethyl)-1-(2,2-diphenylethyl)-2-oxo-1,4-diazepan-5-yl)methyl)acrylamide

(61) N-(((3S,5S)-3-benzyl-1-(2,2-diphenylethyl)-2-oxo-1,4-diazepan-5-yl)methyl)-2-naphthamide

(62) (E)-N-(((3S,5S)-3-benzyl-1-(2,2-diphenylethyl)-2-oxo-1,4-diazepan-5-yl)methyl)-3-(4-chlorophenyl)acrylamide

(63) (E)-N-(((3S,5S)-3-((1H-imidazol-4-yl)methyl)-1-(2,2-diphenylethyl)-2-oxo-1,4-

(64) (E)-3-(4-chlorophenyl)-N-(((3S,5S)-1-(2,2-diphenylethyl)-2-oxo-3-(2-oxo-2-(pyridin-2-ylamino)ethyl)-1,4-diazepan-5-yl)methyl)acrylamide

(65) (E)-3-(4-chlorophenyl)-N-(((3S,5S)-1-(2,2-diphenylethyl)-2-oxo-3-(2-oxo-2-(piperidin-1-yl)ethyl)-1,4-diazepan-5-yl)methyl)acrylamide

(66) 6-chloro-N-(((3S,5S)-2-oxo-3-(3-oxo-3-(piperidin-1-yl)propyl)-1-((S)-2-phenylbutyl)-1,4-diazepan-5-yl)methyl)-2-naphthamide

(67) 3,4-dichloro-N-(((3S,5S)-2-oxo-3-(3-oxo-3-(piperidin-1-yl)propyl)-1-((S)-2-phenylbutyl)-1,4-diazepan-5-yl)methyl)benzamide

(68) (5S,9aS)-5-(2-aminobenzyl)-2-((E)-3-(4-chlorophenyl)acryloyl)-7-(2,2-diphenylethyl)hexahydro-1H-imidazo[1,5-d][1,4]diazepin-6(5H)-one

(69) N-(((3S,5S)-3-(2-aminobenzyl)-1-(2,2-diphenylethyl)-2-oxo-1,4-diazepan-5-yl)methyl)-2-naphthamide

(70) N-(((3S,5S)-3-butyl-2-oxo-1-((S)-2-phenylbutyl)-1,4-diazepan-5-yl)methyl)-6-chloro-2-naphthamide

(71) N-(((3S,5S)-1-(2,2-diphenylethyl)-2-oxo-3-(2-(piperidin-1-yl)benzyl)-1,4-diazepan-5-yl)methyl)-2-naphthamide

(72) N-(((3S,5S)-3-(3-(butyl(methyl)amino)-3-oxopropyl)-2-oxo-1-((S)-2-phenylbutyl)-1,4-diazepan-5-yl)methyl)-2-naphthamide

(73) N-(((3S,5S)-3-(3-(cyclohexylamino)-3-oxopropyl)-2-oxo-1-((S)-2-phenylbutyl)-1,4-diazepan-5-yl)methyl)-2-naphthamide

(74) 6-chloro-N-(((3S,5S)-3-(2-cyclohexylethyl)-2-oxo-1-((S)-2-phenylbutyl)-1,4-diazepan-5-yl)methyl)-2-naphthamide

(75) 6-chloro-N-(((3S,5S)-3-hexyl-2-oxo-1-((S)-2-phenylbutyl)-1,4-diazepan-5-yl)methyl)-2-naphthamide

(76) 6-chloro-N-(((3S,5S)-3-(4-hydroxybutyl)-2-oxo-1-((S)-2-phenylbutyl)-1,4-diazepan-5-yl)methyl)-2-naphthamide

(77) 6-chloro-N-(((3S,5S)-3-(2-methoxyethyl)-2-oxo-1-((S)-2-phenylbutyl)-1,4-diazepan-5-yl)methyl)-2-naphthamide

(78) N-(((3S,5S)-3-(2-(benzyloxy)ethyl)-2-oxo-1-((S)-2-phenylbutyl)-1,4-diazepan-5-yl)methyl)-6-chloro-2-naphthamide

(79) 6-chloro-N-(((3S,5S)-3-isobutyl-2-oxo-1-((S)-2-phenylbutyl)-1,4-diazepan-5-yl)methyl)-2-naphthamide

(80) 3,4-dichloro-N-(((3S,5S)-3-(2-hydroxyethyl)-2-oxo-1-((S)-2-phenylbutyl)-1,4-diazepan-5-yl)methyl)benzamide or pharmaceutically acceptable salts thereof.

INDUSTRIAL UTILITY

As stated previously the compounds of the invention are antagonists of the MC5R and therefore may be used to modulate the activity of MC5R or a fragment or analogue or functional equivalent thereof by exposing MC5R or a fragment or analogue or functional equivalent thereof to a compound of the invention.

Accordingly the compounds of the present invention may be used in the treatment of any condition in which modulation of the activity of MC5R or a fragment or analogue or functional equivalent thereof would lead to a beneficial effect on that condition. As such the compounds of the invention may be used in methods of treating, preventing, or controlling a condition either directly or indirectly associated with the activity of MC5R or a fragment or analogue or functional equivalent thereof in a mammal wherein an MC5R modulating amount of the compound of the invention is administered to the mammal. One condition associated with MC5R activity is excess sebum secretion and conditions related thereto. In one embodiment of the method the condition is selected from the group consisting of acne, seborrhoea, and seborrheic dermatitis. In one embodiment the acne is selected from the group consisting of acne vulgaris, acne, acne conglobata and acne fulminans. In one specific embodiment the condition is acne vulgaris.

For example, downregulation of MC5R leads to a reduction of sebum secretion and can thus be used in the treatment or prophylaxis of a number of conditions in which excess sebum secretion is observed such as acne, seborrhoea and seborrheic dermatitis.

The compounds of the present invention may also be useful in the treatment, prevention or control of a number of conditions that relate to biological processes controlled by MC5R, such as diseases related to inflammation. The compounds may also be useful for the treatment or prevention of cancers, such as Muir-Torre syndrome or other cancers of the sebaceous gland.

Due to their impact on sebum secretion the compounds of the present invention may also find application in treatments where reduced sebum secretion is desirable such as in cosmetic treatments. The compounds may thus be used in methods of reducing sebum secretion by a mammal the method comprising administering an effective amount of a compound of formula (I).

Administration of compounds within Formula (I) to a patient such as humans can be by topical administration, by any of the accepted modes for enteral administration such as oral or rectal, or by parenteral administration such as subcutaneous, intramuscular, intravenous and intradermal routes. Injection can be bolus or via constant or intermittent infusion. The active compound is typically included in a pharmaceutically acceptable carrier or diluent and in an amount sufficient to deliver to the patient a therapeutically effective dose.

In using the compounds of the invention they can be administered in any form or mode which makes the compound bioavailable. One skilled in the art of preparing formulations can readily select the proper form and mode of administration depending upon the particular characteristics of the compound selected, the condition to be treated, the stage of the condition to be treated and other relevant circumstances. We refer the reader to Remingtons Pharmaceutical Sciences, $19^{th}$ edition, Mack Publishing Co. (1995) for further information.

The compounds of the present invention can be administered alone or in the form of a pharmaceutical composition in combination with a pharmaceutically acceptable carrier, diluent or excipient. The compounds of the invention, while effective themselves, are typically formulated and administered in the form of their pharmaceutically acceptable salts as these forms are typically more stable, more easily crystallised and have increased solubility.

The compounds are, however, typically used in the form of pharmaceutical compositions which are formulated depending on the desired mode of administration. As such in a further embodiment the present invention provides a pharmaceutical composition including a compound of Formula (I) and a pharmaceutically acceptable carrier, diluent or excipient. The compositions are prepared in manners well known in the art.

The compounds of formula (I) may be used or administered in combination with one or more additional drug (s). The compounds of the present invention may be used in combination with one or more other pharmaceutically-active compounds, such as other anti-acne treatments. In one embodiment the other pharmaceutically active agent is selected from the group consisting of antibiotics, retinoids, anti-androgens, and steroids. Examples of other pharmaceutically active compounds that may be combined with a compound of formula (I) and administered in concurrent or sequential combination therewith may include, by way of non-limiting example, other anti-acne agents such as oral retinoids (e.g. isotretinoin), topical retinoids (e.g. isotretinoin, adapalene, tazarotene), oral or topical antibiotics (e.g. clindamycin, erythromycin, minocycline, tetracycline, benzoyl peroxide), or hormonal therapies (e.g. drospirenone, norgestimate—ethinyl estradiol, cyproterone acetate). As stated these components can be administered in the same formulation or in separate formulations. If administered in separate formulations the compounds of the invention may be administered sequentially or simultaneously with the other drug(s).

A compound of the invention is typically combined with the carrier to produce a dosage form suitable for the particular patient being treated and the particular mode of administration. For example, a formulation intended for the oral administration to humans may contain from about 0.5 mg to about 5 g of the compound of the invention, compounded with an appropriate and convenient amount of carrier material which may vary from about 5 to about 99.95 percent of the total composition. Representative dosage forms will generally contain between from about 1 mg to about 500 mg of a compound of the invention, typically 25 mg, 50 mg, 100 mg, 200 mg, 300 mg, 400 mg, 500 mg, 600 mg, 800 mg, or 1000 mg. Compounds of the present invention may also be formulated for topical delivery in formulations such as solutions, ointments, lotions, gels, creams, microemulsions or transdermal patches. For example, these topical formulations may contain from 0.005 to 5% (wt/wt or wt/vol) of a compound of the invention.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of micro-organisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents that delay absorption such as aluminium monostearate and gelatin.

If desired, and for more effective distribution, the compounds can be incorporated into slow release or targeted delivery systems such as polymer matrices, liposomes, and microspheres.

The injectable formulations can be sterilized, for example, by filtration through a bacterial-retaining filter, or by incorporating sterilizing agents in the form of sterile solid compositions that can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

If desired, and for more effective distribution, the compounds can be incorporated into slow release or targeted delivery systems such as polymer matrices, liposomes, and microspheres.

The active compounds can also be in microencapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminium metahydroxide, bentonite, agar-agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

For topical administration, the active agent may be in the form of an ointment, cream, suspension, lotion, powder, solution, paste, gel, spray, aerosol or oil. Alternatively, the composition may be delivered via a liposome, nanosome, rivosome, or nutri-diffuser vehicle. Alternately, a formulation may comprise a transdermal patch or dressing such as a bandage impregnated with an active ingredient and optionally one or more carriers or diluents. To be administered in the form of a transdermal delivery system, the dosage administration will, of course, be continuous rather than intermittent throughout the dosage regimen. Methods for producing formulations for topical administration are known in the art.

The compositions used for topical administration typically contain a pharmaceutically acceptable carrier which may be any vehicle that is toxicologically and pharmaceutically acceptable. Typical pharmaceutically acceptable carriers that can be used in compositions of the present invention include water, ethanol, acetone, isopropyl alcohol, stearyl alcohol, freons, polyvinyl pyrrolidone, propylene glycol, polyethylene glycol, fragrances, gel-producing materials, mineral oil, stearic acid, spermaceti, sorbitan, monoleate, polysorbates, "Tweens," sorbitol, methyl cellulose, petrolatum, a mineral oil (vaseline oil), which may be any petroleum based product; modified or unmodified vegetable oils such as peanut oil, wheatgerm oil, linseed oil, jojoba oil, apricot kernel oil, walnut oil, palm oil, pistachio oil, sesame oil, colza oil, cade oil, corn germ oil, peach kernel oil, poppyseed oil, pine oil, castor oil, soya oil, safflower oil, coconut oil, hazelnut oil, grapeseed oil, avocado oil, soy oil, sweet almond oil, calophyllum oil, castor oil, olive oil, sunflower oil, or animal oils such as whale oil, seal oil, menhaden oil, halibut liver oil, cod liver oil, cod, tuna, turtle tallow, horse's hoof, sheep's foot, mink, otter, marmot oil and the like; synthetic oils such as silicon oil such as dimethylpolysiloxane; alkyl and alkenyl esters of fatty acids, such as isopropyl esters of myristic, palmitic and stearic acids and fatty esters which are solid at room temperature; waxes such as lanolin wax, candelilla wax, spermaceti, cocoa butter, karite butter, silicon waxes, hydrogenated oils which are solid at room temperature, sucro-glycerides, oleates, myristates, linoleates, stearates, paraffin, beeswax, carnauba wax, ozokerite, candelilla wax, microcrystalline wax; fatty alcohols such as lauryl, cetyl, myristyl, stearyl, palmityl and oleyl alcohols; polyoxyethylated fatty alcohols; and wax esters, lanolin and its derivatives, perhydrosqualene and saturated esters, ethyl palmitate, isopropyl palmitate, alkyl myristates such as isopropyl myristate, butyl myristate and decyl myristate, hexyl stearate, triglyceride esters, triglycerides of octanoic and decanoic acid, cetyl ricinoleate, stearyl octanoate (Purcellin oil), fatty acids, polyhydric alcohols, polyether derivatives, fatty acid monoglycerides, polyethylene glycol, propylene glycol, alkyl ethoxy ether sulfonates, ammonium alkyl sulfates, fatty acid soaps, and hydrogenated polyisobutene, and mixtures of waxes and oils.

The compositions for topical administration may be formulated in numerous forms. However, the composition may often take the form of an aqueous or oily solution or dispersion or emulsion or a gel or a cream. An emulsion may be an oil-in-water emulsion or a water-in-oil emulsion.

The oil phase of water-in-oil or oil-in-water emulsions may comprise for example: a) hydrocarbon oils such as paraffin or mineral oils; b) waxes such as beeswax or paraffin wax; c) natural oils such as sunflower oil, apricot kernel oil, shea butter or jojoba oil; d) silicone oils such as dimethicone, cyclomethicone or cetyldimethicone; e) fatty acid esters such as isopropyl palmitate, isopropyl myristate, dioctylmaleate, glyceryl oleate and cetostearyl isononanoate; f) fatty alcohols such as cetyl alcohol or stearyl alcohol and mixtures thereof (eg cetearyl alcohol); g) polypropylene glycol or polyethylene glycol ethers, eg PPG-14 butyl ether; or h) mixtures thereof.

Emulsifiers used may be any emulsifiers known in the art for use in water-in-oil or oil-in-water emulsions. Known cosmetically acceptable emulsifiers include: a) sesquioleates such as sorbitan sesquioleate, available commercially for example under the trade name Arlacel 83 (ICI), or polyglyceryl-2-sesquioleate; b) ethoxylated esters of derivatives of natural oils such as the polyethoxylated ester of hydrogenated castor oil available commercially for example under the trade name Arlacel 989 (ICI); c) silicone emulsifiers such as silicone polyols available commercially for example under the trade name ABIL WS08 (Th. Goldschmidt AG); d) anionic emulsifiers such as fatty acid soaps e.g. potassium stearate and fatty acid sulphates e.g. sodium cetostearyl sulphate available commercially under the trade name Dehydag (Henkel); e) ethoxylated fatty alcohols, for example the emulsifiers available commercially under the trade name Brij (ICI); f) sorbitan esters, for example the emulsifiers available commercially under the trade name Span (ICI); g) ethoxylated sorbitan esters, for example the emulsifiers available commercially under the trade name Tween (ICI); h) ethoxylated fatty acid esters such as ethoxylated stearates, for example the emulsifiers available commercially under the trade name Myrj (ICI); i) ethoxylated mono-, di-, and tri-glycerides, for example the emulsifiers available commercially under the trade name Labrafil (Alfa Chem.); j) non-ionic self-emulsifying waxes, for example the wax available commercially under the trade name Polawax (Croda); k) ethoxylated fatty acids, for example, the emulsifiers available commercially under the trade name Tefose (Alfa Chem.); l) methylglucose esters such as polyglycerol-3 methyl glucose distearate available commercially under the name Tegocare 450 (Degussa Goldschmidt); or m) mixtures thereof.

Gels for topical administration may be aqueous or non-aqueous. Aqueous gels are preferred. The gel will contain a thickening agent or gelling agent in order to give sufficient viscosity to the gel. A variety of thickening agents may be used according to the nature of the liquid carrier and the viscosity required and these are recited hereinafter. A particularly suitable thickener is a copolymer of acryloyl dimethyl tauric acid (or a salt thereof), preferably a copolymer of that monomer with another vinylic monomer. For example, the thickening agent is a copolymer of a salt of acryloyl dimethyl tauric acid with another vinylic monomer. The salt may be a salt of a Group I alkali metal, but is more preferably an ammonium salt. Examples of suitable copolymer thickening agents are: i) Ammonium acryloyl dimethyl taurate I vinyl pyrrolidone copolymer, ie a copolymer of ammonium acryloyl dimethyl taurate and vinyl pyrrolidone (1-vinyl-2-pyrrolidone).

The composition may additionally comprise other skin care active agents which are well known in the art which may be effective to aid the normal functioning of the skin. One group of preferred compositions comprise hydrolysed milk protein to regulate sebum production.

The composition may additionally comprise other components which will be well known to those skilled in the art such as emollients, humectants, emulsion stabilising salts, preservatives, chelating agents or sequestering agents (sequestrants), abrasives, anti-oxidants, stabilisers, pH adjusters, surfactants, thickeners, diluents, perfumes and colourings.

The topical formulations may desirably include a compound that enhances absorption or penetration of the active ingredient through the skin or other affected areas. Examples of such dermal penetration enhancers include dimethylsulfoxide and related analogues.

Synthesis of Compounds of the Invention

The general synthetic route to the claimed products proceeds through the key intermediate A, produced as outlined in Schemes 1 or 2.

In Scheme 1, an amino acid derivative V—N($R^2$)—Y—$CO_2H$ (V=$R^1X$ or an amine protecting group $P^1$) is converted to a Weinreb amide via activation of the carboxyl group and amidation with N-methyl methoxyamine. Addition of a vinyl Grignard reagent produces the aminoalkyl vinyl ketone, which undergoes conjugate addition by the $R^6R^7R^8C$—$(CR^{6a}R^{6b})_rNH_2$ amine component (shown as $WNH_2$ for simplicity). The resulting secondary amine is acylated under standard peptide coupling conditions with the protected amino acid, $P^2$—NHCH(U)—$CO_2H$, where U represents either the final $ZR^4$ side chain, a protected final side chain $ZR^4$—$P^3$, or a precursor that requires chemical modification to form the final $ZR^4$ side chain. Deprotection of the $P^2$ protecting group is followed by intramolecular reductive amination of the ketone using standard reduction conditions, such as $H_2$/Pd catalyst, $NaBH_4$, $NaBH_3CN$, or $NaBH(OAc)_3$, forming key intermediate A. If Y=$CH_2$ or $CH_2CH_2$, A is formed as the predominant diastereomer. If V=$R^1X$ and U=$ZR^4$, A is the final product.

Scheme 1: Synthesis of Intermediate A via Intramolecular Reductive Amination

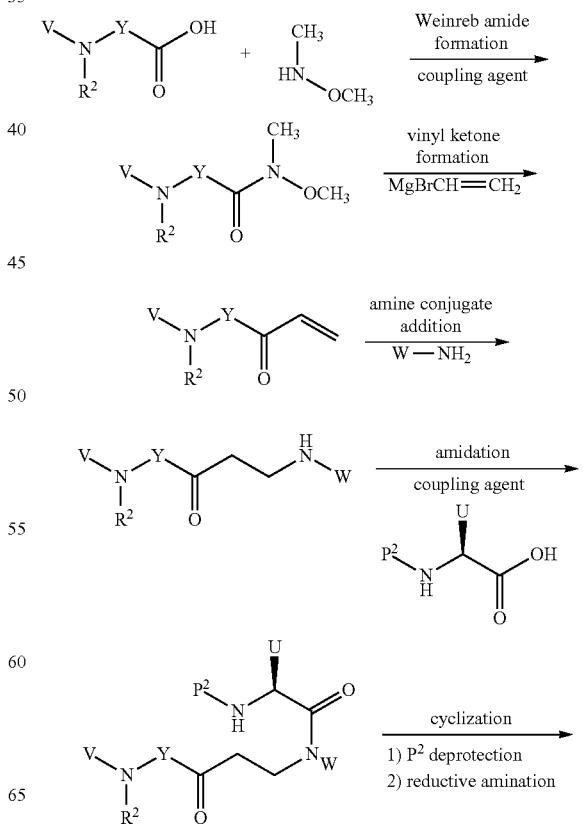

-continued

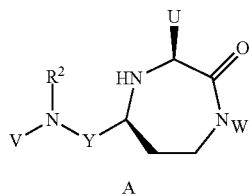

A where U = ZR$^4$, a protected form thereof or a precursor thereof,
V = P$^1$ or R$^1$X, and W = R$^6$R$^7$R$^8$C(CR$^{5a}$R$^{5b}$)$_r$-
Final product if V = R$^1$X, U = ZR$^4$ In Scheme 2, an alternate route to the desired intermediate A begins with the same Weinreb amide formation, vinyl Grignard addition, and amine conjugate addition. At this point, the secondary amine is protected with an amine protecting group P$^4$. The ketone is then reductively aminated with a protected amino ester, H$_2$NCH(U)—CO$_2$P$^5$, producing a mixture of diastereomers that are carried through the next reaction steps. The ring system is generated by deprotection of the P$^4$ and P$^5$ protecting groups, followed by amide bond formation using standard peptide coupling reagents. Alternatively, the P$^4$ protecting group is removed and cyclization achieved by thermal or base-induced cyclization with the P$^5$-protected ester. The cyclization produces a mixture of two diasteromers, A and B, from which the preferred diastereomer A can be separated by chromatography.

Scheme 2: Synthesis of Intermediate A via Intermolecular Reductive Amination

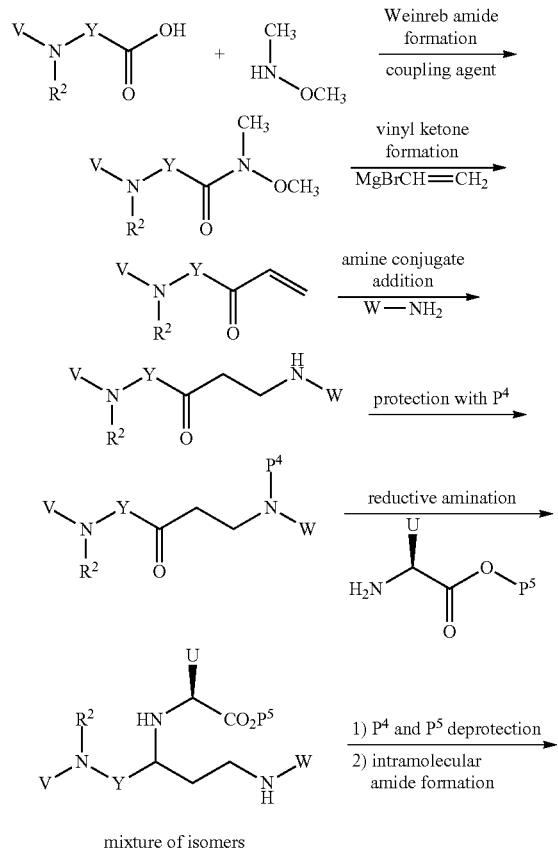

mixture of isomers

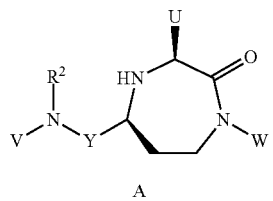

A
separate desired

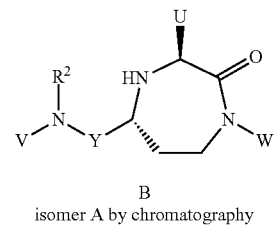

B
isomer A by chromatography where U = ZR$^4$, a protected form thereof or a precursor thereof,
V = P$^1$ or R$^1$X, and W = R$^6$R$^7$R$^8$C(CR$^{5a}$R$^{5b}$)$_r$-
Final product if V = R$^1$X, U = ZR$^4$ The key intermediate A may be the final product if U=ZR$^4$ and V=R$^1$X, but otherwise is converted into the final product as illustrated in Schemes 3, 4 and 5.

In Scheme 3, where V=R$^1$X, the final product is obtained by modification of the U side chain, such as removal of a P$^3$ protecting group, or removal of a P$^3$ protecting group followed by further chemical modification.

Scheme 3: V = R$^1$X

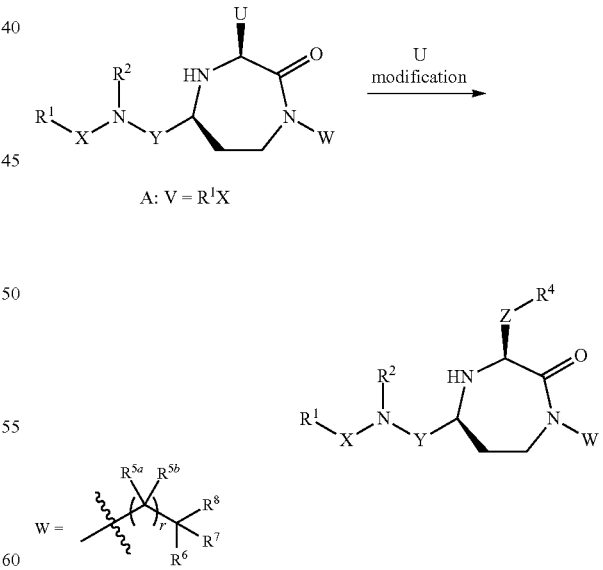

In Scheme 4, where V=P$^1$, the final product is obtained by removal of the P1 protecting group followed by introduction of the R$^1$X substituent. If U=ZR$^4$, this produces the final product. Alternatively, the U side chain is then modified to produce the final ZR$^4$ group as in Scheme 3.

Scheme 4: V = P¹

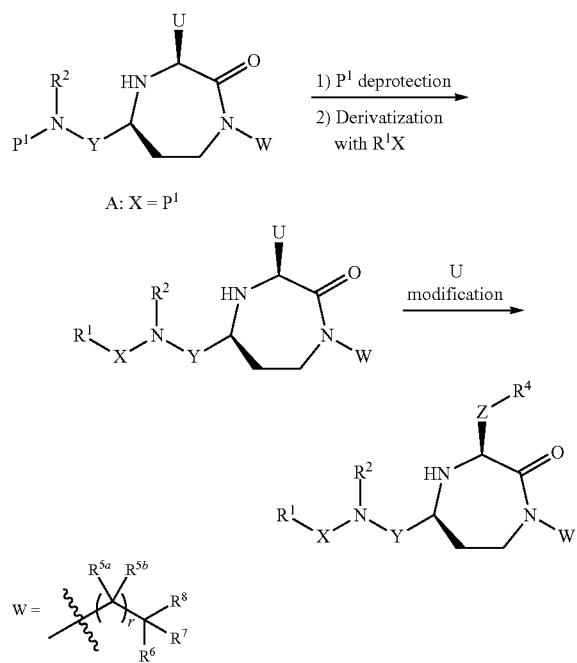

In Scheme 5, where V=P¹, the final product is obtained by first modifying the U side chain to produce the final ZR⁴ group as in Scheme 3. This is followed by removal of the P1 protecting group followed by introduction of the R¹X substituent.

Scheme 5: V = P¹

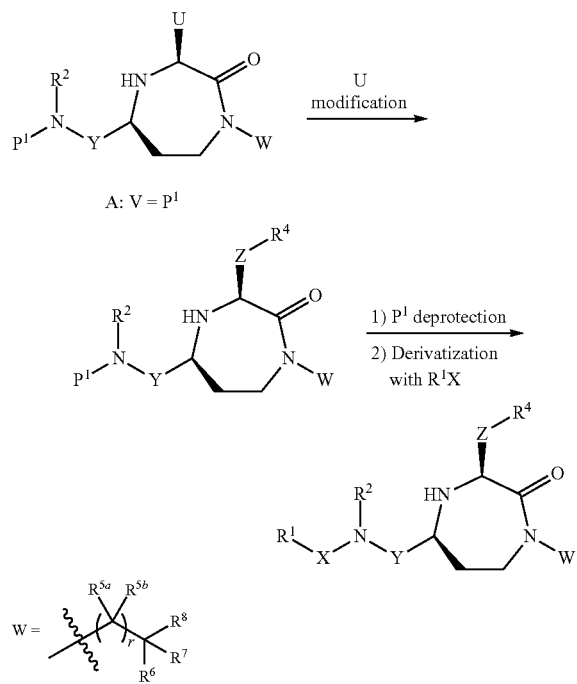

It is also possible to modify the W substituent, if desired, during these reaction sequences.

EXAMPLES

The following examples are intended to illustrate the embodiments disclosed and are not to be construed as being limitations thereto. Additional compounds, other than those described below, may be prepared using the following described reaction schemes as discussed above or appropriate variations or modifications thereof. All starting materials described in the Examples below are commercially available or readily synthesized by those skilled in the art.

Instrumentation

HPLC analyses were carried out on an Agilent 1100 Series Purification System with a Phenomenex Synergi 4μ Max-RP 80A, 50×2.00 mm analytical HPLC column, with peak detection by UV. The standard analysis employed a 1 mL/min flow rate of 0.05% trifluoroacetic acid (TFA) in water (Solvent A) and 0.05% TFA in 90:10 acetonitrile:water (Solvent B), using a gradient of 5% B (initial) to 95% B over 9 min. Mass spectra were run on an Applied Biosystems MDS Sciex API 2000 LC/MS/MS triple quadrupole mass spectrometer and analyzed by ion spray mass spectrometry (ISMS). Preparative scale HPLC was carried out on a Waters Delta Prep 3000 HPLC system with peak detection by UV (Waters model 486 tunable absorbance detector), using Phenomenex Luna 10μ C5 100A, 250×21.20 mm (20 mg scale), Phenomenex Luna 15μ C8(2) 100A, 250×30.00 mm (50 mg scale), or Phenomenex Luna 15μ C8(2) 100A, 250×50.00 mm (100 mg scale) HPLC columns. The solvent system employed various gradients of 0.05% TFA in water (Solvent A) and 0.05% TFA in 90:10 acetonitrile:water (Solvent B).

The following examples 1 to 6 provide general synthetic procedures that may be followed in order to carry out the transformations described in schemes 1 to 5. In order to make different end products using these procedures it is necessary to either vary a variable group on the starting material or to vary a variable group on one of the reagents depending upon the nature of the reaction. It will be apparent to a skilled addressee from a reading of the general procedures how to vary either the starting material or the reagents used in the procedure to produce differing end products. In addition depending upon the starting materials and the reagents it may be necessary and/or desirable to make slight modifications to the described general procedures in order to provide the most facile synthesis of the desired end product.

Example 1

General Procedure—Weinreb Amide Formation

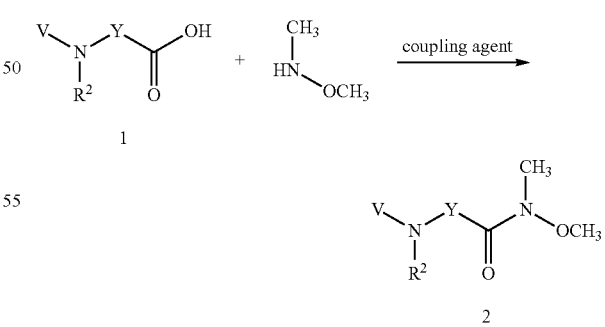

BOP reagent (100 mmol) and diisopropylethylamine (DIPEA) (100 mmol) is added to a stirred solution of the amino acid (1) (100 mmol) in dichloromethane (DCM) (100 mL). The solution is then stirred at room temperature for 10 mins, before addition of a premixed solution of N,O-dimethylhydroxylamine hydrochloride (100 mmol) and DIPEA (100 mmol) followed by stirring at room temperature overnight. The DCM is then removed by rotary evaporation and the residue taken up in ethyl acetate (EtOAc) (200 mL). The organic phase is then washed with 1N HCl (3×100 mL), H$_2$O (3×100 mL), saturated NaHCO$_3$ aqueous solution (3×100 mL) and brine (1×10 mL). The organic phase is then dried (MgSO$_4$) and the EtOAc removed to give the Weinreb amide (2) as a white solid or an oil.

Example 2

General Procedure—Vinyl Grignard Addition to Weinreb Amide to Form α,β-Unsaturated Ketones of Formula (3)

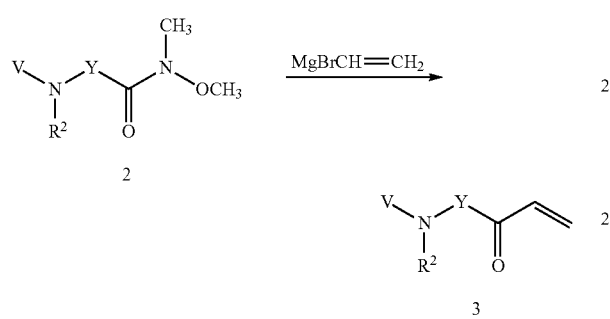

To the Weinreb amide (2) (15 mmol) in DCM (10 mL) at 0° C. is added vinyl magnesium bromide (45 mmol) in THF (45 mL). The reaction is stirred for 2 hrs and monitored by HPLC. The reaction is then quenched by adding it to a mixture of ice and 1M HCl (200 mL). The aqueous mixture is extracted with DCM (3×100 mL) and the organic layers combined and washed with 1M HCl (2×200 mL) and H$_2$O (3×100 mL). The organic phase is dried (MgSO$_4$) to provide a solution of the α,β-unsaturated ketone (3). The α,β-unsaturated ketone (3) may be isolated by rotary evaporation or it may be used in solution without further purification. If the intention is to use the α,β-unsaturated ketone (3) in solution the volume is reduced to 100 mL by rotary evaporation and stored for later use.

Example 3

General Procedure—Conjugate Addition of Amine to α,β-Unsaturated Ketones of Formula (3) to Produce Compounds of Formula (4)

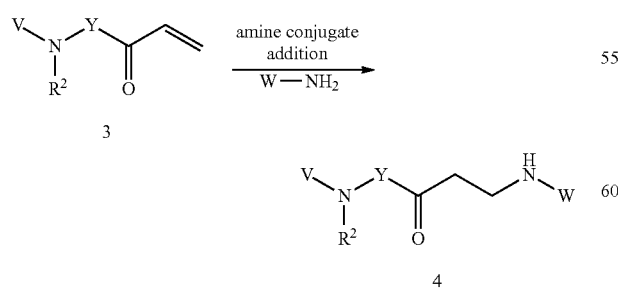

To the amine W—NH$_2$ (7.4 mmol) in DCM (10 mL) is added a solution of the α,β-unsaturated ketone (3) (5.7 mmol) in DCM (50 mL). The solution is stirred at room temperature for 15 mins, or until analysis indicates that all of (3) has been consumed. The solution of compound (4) is immediately used without purification for the subsequent reaction.

Example 4

General Procedure—Acylation of Aminoketone (4)

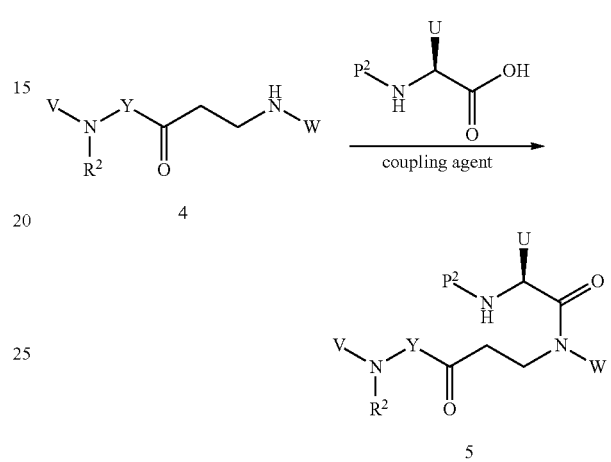

The amine acid P$^2$—NHCH(U)—CO$_2$H (15 mmol) and DIC (15 mmol) is added to a solution of DCM containing 10 mmol of the conjugate addition adduct 4. The reaction is stirred at room temperature overnight. The DCM is removed by rotary evaporation and the residue is then subjected to column chromatography on silica gel using petroleum spirit: EtOAc to give 5.

As an alternative, the DIC may be replaced with HATU (15 mmol) and DIPEA (15 mmol). The reaction is stirred at room temperature overnight. The DCM is removed by rotary evaporation and the residue is taken up in EtOAc (100 mL). The organic layer is washed with saturated sodium bicarbonate solution (2×100 mL), saturated ammonium chloride solution (2×100 mL) and brine (2×100 mL). The organic phase is dried and the solvent removed under reduced pressure. The residue is subjected to column chromatography on silica gel using petroleum ether:EtOAc to give 5.

Example 5

General Procedure—P$^2$ Deprotection and Cyclization

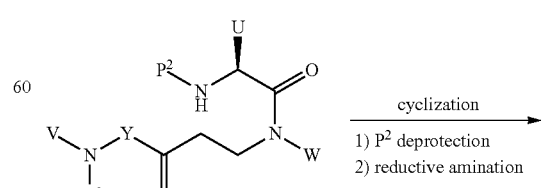

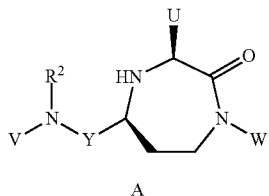

A

The procedure adopted for the removal of the P2 protecting group will vary depending upon the exact nature of the protecting group. As will be appreciated by a skilled addressee a large number of possible protecting groups may be used and a skilled worker in the art will readily be able to determine an appropriate procedure for the removal of any particular protecting group from procedures known in the art. Nevertheless in order to assist the reader general procedures for the removal of the more common protecting groups are provided.

$P^2$=Fmoc: To compound 5 (2 mmol) in DCM (3 mL) is added diethylamine (20 mmol). The reaction is stirred at room temperature for 1 hr. The DCM and diethylamine is then removed by rotary evaporation. DCM (5 mL) and sodium triacetoxyborohydride (3 mmol) are then added, and the reaction stirred overnight at room temperature. The organic phase is washed with saturated sodium bicarbonate solution (25 mL), dried ($MgSO_4$) and the DCM removed to give the cyclised product A. This may be purified by flash chromatography on silica gel or used without purification.

$P^2$=Boc: To compound 5 (2 mmol) in DCM (3 mL) is added TFA (3 mL) and the reaction stirred at room temperature for 2 hrs. The DCM and TFA are then removed by rotary evaporation. DCM (5 mL) and sodium triacetoxyborohydride (3 mmol) is then added, and the reaction stirred overnight at room temperature. The organic phase is washed with saturated sodium bicarbonate solution (25 mL), dried ($MgSO_4$) and the DCM removed to give the cyclised product A. This may be purified by flash chromatography on silica gel or used without purification.

$P^2$=Cbz: A mixture of crude 5 (1 mmol) and 5% Pd/C (200 mg) in 2-propanol (15 mL) is shaken at room temperature under hydrogen (30 psi) for 24 hrs. The mixture is then filtered through a pad of Celite and the filtrate concentrated under reduced pressure to give a crude product. Purification by flash chromatography on silica gel (100% EtOAc) may be used to give A.

Example 6

General Procedure—$P^1$ Deprotection and Derivatization with $R^1X$

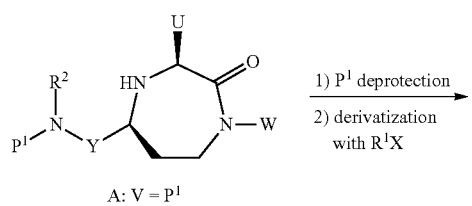

A: V = $P^1$

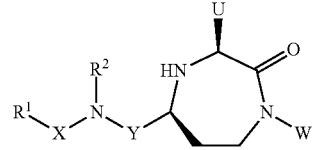

6

The procedure adopted for the removal of the P1 protecting group will vary depending upon the exact nature of the protecting group. As will be appreciated by a skilled addressee a large number of possible protecting groups may be used and a skilled worker in the art will readily be able to determine an appropriate procedure for the removal of any particular protecting group from procedures known in the art. Nevertheless in order to assist the reader general procedures for the removal of the more common protecting groups are provided.

Deprotection, $P^1$=Cbz:
To the cyclised product A (1 mmol) in methanol (5 mL) is added catalytic Pd/C. The reaction is stirred under a hydrogen atmosphere overnight. The reaction mixture is filtered through Celite and the methanol removed by rotary evaporation to give the free amine. The amine may be used in the next reaction without purification.

Deprotection, $P^1$=Boc:
To the cyclised product A (1 mmol) in DCM (1 mL) is added TFA (1 mL) and the reaction stirred at room temperature for 2 hrs. The solvent is removed by rotary evaporation to give the amine TFA salt, which may be used in the next reaction without purification.

Deprotection, $P^1$=Alloc:
To the cyclised product A (1 mmol) in DCM (6 mL) is added 1,3-dimethylbarbituric acid (0.2 mmol) and palladium tetrakis triphenylphosphine (10 mg). The reaction is evacuated and stirred at room temperature for 1 hr. The DCM is removed under reduced pressure to give the crude free amine, which may be used in the next reaction without purification.

Derivatisation with $R^1X$ when X=C(=O):
To the free amine (1 mmol) in DCM (5 mL) is added DIPEA (1 mmol.), BOP reagent (1.5 mmol) and acid component $R^1CO_2H$ (1.5 mmol). The reaction is stirred at room temperature for 2 hrs. Rotary evaporation and preparative HPLC gives the purified adduct.

Example 7

Synthesis of Compound 7 6-chloro-2-naphthoic acid

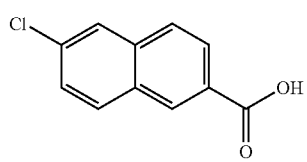

6-chloro-2-naphthoic acid

A suspension of 6-bromo-2-naphthoic acid (3.0 g, 11.47 mmol), CuCl (11.7 g, 114.64 mmol) and CuI (2.19 g, 11.50 mmol) in degassed DMF (45 mL) was heated to reflux under argon in dark for 4 hrs. After cooling to room temperature, the solution was decanted into $H_2O$ (200 mL) and the resulting mixture was extracted with EtOAc (2×500 mL). The combined organic layers were then washed with H$_2$O (4×500 mL) followed by brine (1×500 mL), dried over MgSO$_4$, filtered and concentrated under reduced pressure to dryness. The residue was triturated with CH$_3$CN and the solid obtained was then re-crystallized from EtOAc to give the pure product 7 (2.2 g, 93%) as an off-white solid. HPLC t$_R$ 6.47 min.

Example 8

Synthesis of Compound 8 (S)-2-phenylbutanol

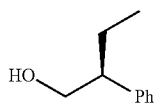

8

To a suspension of sodium borohydride (2.36 g, 62.4 mmol) in THF (50 mL) was added a solution of (S)-2-phenylbutyric acid (4.27 g, 26.0 mmol) in THF (40 mL) slowly at 0° C. The mixture was stirred until the evolution of gas ceased. A solution of iodine (6.60 g, 26.0 mmol) in THF (40 mL) was then added slowly at 0° C. After addition, the resulting mixture was allowed to warm to room temperature and stirred for 1 hr. The reaction solution was then slowly poured into a 1 N HCl solution (280 mL) and the resulting mixture was diluted with EtOAc (250 mL). The aqueous layer was extracted with EtOAc (150 mL×3) and the combined organic layers were then washed with saturated NaHCO$_3$ (aq), 0.5 M Na$_2$S$_2$O$_3$ (aq) and brine. This organic solution was dried over MgSO$_4$, filtered and concentrated under reduced pressure to give the crude product. Purification by flash chromatography on silica gel (Petroleum ether:EtOAc 4:1) gave the desired product 8 as a colorless oil in quantitative yield. HPLC t$_R$ 5.24 min.

Example 9

Synthesis of Compound 9
(S)-1-mesyloxy-2-phenylbutane

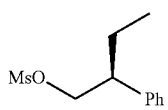

9

To a mixture of alcohol 8 (3.9 g, 26.0 mmol) and triethylamine (5.5 mL, 39.5 mmol) in DCM (90 mL) was added a solution of methanesulfonyl chloride (4.47 g, 39.0 mmol) in DCM (30 mL) slowly at 0° C. After addition, the resulting mixture was allowed to warm to room temperature and stirred for 2 hrs. 1 N HCl (70 mL) was then added to the above mixture and the aqueous layer was extracted with DCM (1×70 mL). The combined organic layers were washed with brine (150 mL), dried over MgSO$_4$, filtered and concentrated under reduced pressure to give the crude product 9 as a colorless oil. This crude product was used in the next step without further purification. HPLC t$_R$ 6.48 min.

Example 10

Synthesis of Compound 10
(S)-1-azido-2-phenylbutane

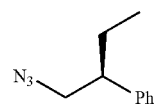

10

A suspension of mesylate 9 (5.93 g, 26.0 mmol) and sodium azide (5.7 g, 78.0 mmol) in DMF (60 mL) was heated at 85° C. for 3 hrs. After cooling to room temperature, the mixture was diluted with H$_2$O (200 mL) and extracted with EtOAc (250 mL). The organic layer was then washed with H$_2$O (4×150 mL) followed by brine (150 mL), dried over MgSO$_4$, filtered and concentrated under reduced pressure to give the crude product. Purification by flash chromatography on silica gel (100% petroleum ether as the eluent) gave the pure azide product 10 (4.03 g, 88%) as a colorless oil. HPLC t$_R$ 7.67 min.

Example 11

Synthesis of Compound 11 (S)-2-phenylbutylamine

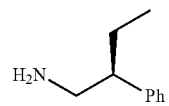

11

A mixture of azide 10 (4.0 g, 22.8 mmol) and Lindlar's catalyst (1.5 g) in EtOAc (50 mL) was shaken at room temperature under H$_2$ (40 psi) over-night. The mixture was then filtered through a pad of Celite and the filtrate was concentrated under reduced pressure to give the crude amine product 11 (3.4 g, 100%) as a light yellowish oil. This crude product was used for the conjugate addition reactions without further purification. MS (ESI) 150 (M+1); HPLC t$_R$ 1.84 min.

Example 12

Synthesis of Compound 12 benzyl
2-(methoxy(methyl)amino)-2-oxoethylcarbamate

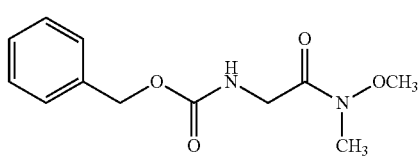

12 benzyl 2-(methoxy(methyl)amino)-
2-oxoethylcarbamate

To Cbz-glycine (10 g, 47.8 mmol, Aldrich) in DCM (100 mL) was added BOP reagent (21.5 g, 48.6 mmol) and DIPEA (6.5 mL, 46.0 mmol). After stirring at room temperature for 10 mins, N,O-dimethylhydroxylamine hydrochloride (4.9 g, 50.2 mmol) and DIPEA (6.5 mL, 46.0 mmol) were added. The reaction was stirred at room temperature overnight. The DCM was removed by rotary evaporation and the residue taken up in EtOAc (100 mL). The organic phase was washed with water (3×100 mL), saturated sodium bicarbonate solution (3×100 mL), water (3×100 mL), 1M hydrochloric acid (3×100 mL), brine (3×100 mL). The organic phase was dried (magnesium sulphate) and the EtOAc removed to give the Weinreb amide 12 as a white solid (7.78 g, 64%).

Example 13

Synthesis of Compound 13 benzyl 2-oxobut-3-enylcarbamate

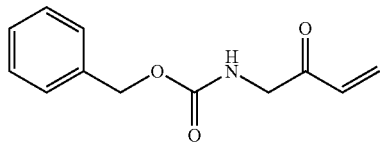

benzyl 2-oxobut-3-enylcarbamate

To the Weinreb amide 12 (3.89 g, 15.42 mmol) in DCM (10 mL) at 0° C. was added vinyl magnesium bromide (45 mmol) in THF (45 mL). The reaction was stirred for 2 hrs and monitored by HPLC. The reaction was added to a mixture of ice and 1M hydrochloric acid (200 mL). The aqueous mixture was extracted with DCM (3×100 mL) and washed with 1M hydrochloric acid (2×200 mL) and water (3×100 mL). The organic phase was dried (magnesium sulphate) and the volume reduced to 100 mL by rotary evaporation. The α,β-unsaturated ketone 13 was stored and used in solution without purification.

Example 14

Synthesis of Compound 14 (S)-9-fluorenylmethyl 7-[(S)-2-phenylbutyl]-2-methyl-15-phenyl-6,10,13-trioxo-14-oxa-7,12-diazaoctadecan-5-ylcarbamate

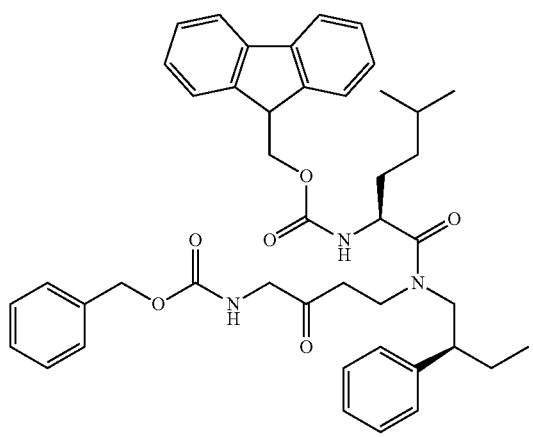

(S)-9-fluorenylmethyl 7-[(S)-2-phenylbutyl]-2-methyl-15-phenyl-6,10,13-trioxo-14-oxa-7,12-diazaoctadecan-5-ylcarbamate To (S)-phenylbutylamine (0.14 g, 0.9 mmol) in DCM (3 mL) was added the α,β-unsaturated ketone 13 (0.9 mmol) in DCM (7.5 mL). After stirring at room temperature for 15 mins, Fmoc-L-Homoleucine (0.4 g, 1.09 mmol) and DIC (0.18 mL, 1.16 mmol) were added. The reaction was stirred at room temperature overnight. The DCM was removed by rotary evaporation and the residue was purified by column chromatography (silica gel, 1:1 to 0:1 petroleum ether:EtOAc) to give 14 (0.54 g, 84%).

Example 15

Synthesis of Compound 15 benzyl((3S,5S)-3-isopentyl-2-oxo-1-((S)-2-phenylbutyl)-1,4-diazepan-5-yl)methylcarbamate

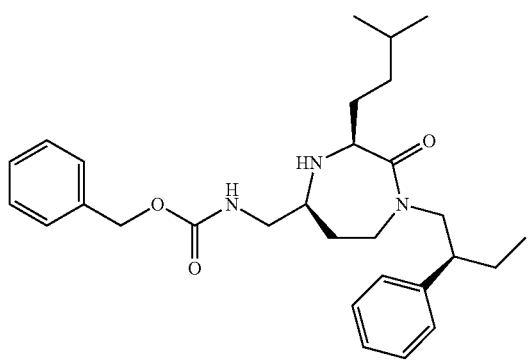

benzyl ((3S,5S)-3-isopentyl-2-oxo-1-((S)-2-phenylbutyl)-1,4-diazepan-5-yl)methylcarbamate 1-(2,2-diphenylethyl)-1,4-diazepan-2-one To Compound 14 (0.54 g, 0.75 mmol) in DCM (3 mL) was added diethylamine (1.5 mL, 14.5 mmol). The reaction was stirred at room temperature for 1 hr. The DCM and diethylamine were removed by rotary evaporation. DCM (5 mL) and sodium triacetoxyborohydride (0.2 g, 0.94 mmol) were added, and the reaction was stirred overnight at room temperature. The organic phase was washed with saturated sodium bicarbonate solution (25 mL), dried (magnesium sulphate) and the DCM removed to give the cyclised product, which was purified by column chromatography (silica gel, petroleum ether:EtOAc) to give 0.32 g (89%) of 15.

Example 16

Synthesis of Compound 16 (3S,5S)-5-(aminomethyl)-3-isopentyl-1-((S)-2-phenylbutyl)-1,4-diazepan-2-one

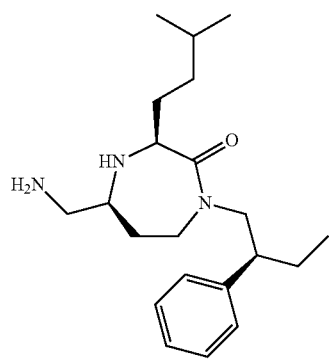

(3S,5S)-5-(aminomethyl)-3-isopentyl-1-((S)-2-phenylbutyl)-1,4-diazepan-2-one

To the cyclised product 15 (0.32 g, 0.67 mmol) in methanol (5 mL) was added catalytic Pd/C. The reaction was stirred under a hydrogen atmosphere for 1 hr. The reaction mixture was filtered through Celite and the methanol removed by rotary evaporation to give the amine 16 (0.23 g, 100%), which was used in the next step without purification.

Example 17

Synthesis of Compound 17 6-chloro-N-(((3S,5S)-3-isopentyl-2-oxo-1-((S)-2-phenylbutyl)-1,4-diazepan-5-yl)methyl)-2-naphthamide

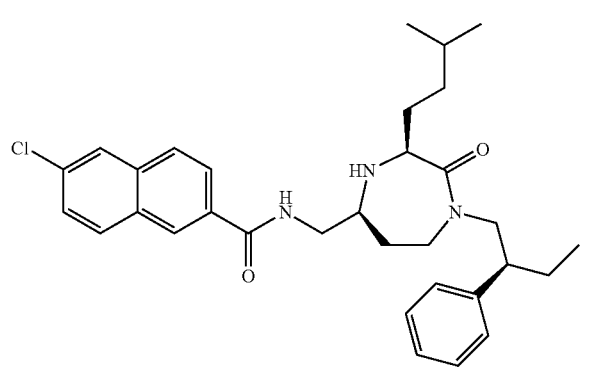

6-chloro-N-(((3S,5S)-3-isopentyl-2-oxo-1-((S)-2-phenylbutyl)-1,4-diazepan-5-yl)methyl)-2-naphthamide To the amine 16 (0.12 mg, 0.34 mmol) in DCM (1 mL) was added DIPEA (0.1 mL, 0.57 mmol), BOP reagent (0.16 g, 0.36 mmol) and 6-chloro-2-naphthoic acid (0.07 g, 0.34 mmol). The reaction was stirred at room temperature for 2 hrs. The solvent was removed under high vacuum, and the residue purified by preparative HPLC to give 32.0 mg (18%) of 17 as the TFA salt. The TFA salt (30 mg) in DCM (15 mL) was washed with saturated sodium bicarbonate solution (15 mL). The DCM was removed and 1M HCl (2 mL) and acetonitrile (2 mL) was added. Solvent removal by lyophilisation gave 24 mg of 17 as the HCl salt. MS (ESI) 534.4 (M+1); HPLC $t_R$ 7.64 min.

NMR: $^1$H NMR (CDCl$_3$, 400 MHz): 8.08-7.75 (m, 5H), 7.41 (dd, J=8.8, 2.0 Hz, 1H), 7.32-7.13 (m, 5H), 4.05-3.99 (m, 2H), 3.64-3.54 (m, 2H), 3.29 (m, 1H), 3.23-3.12 (m, 3H), 2.88-2.82 (m, 1H), 2.04-1.94 (m, 2H), 1.69-1.58 (m, 3H), 1.51-1.47 (m, 1H), 0.90-0.83 (m, 3H), 0.81-0.76 (m, 9H).

NMR: $^{13}$C NMR (CDCl$_3$, 100 MHz): 167.6, 142.4, 135.5, 133.7, 130.8 (2C), 130.6, 128.7 (2C), 128.3, 128.0 (2C), 127.8, 127.6, 127.4, 126.9, 126.4, 125.1, 56.6, 46.7, 46.5, 35.3, 32.2, 29.6, 28.9, 28.0, 26.6, 22.9, 22.6, 22.3, 14.3, 12.1

UV: $\lambda_{max}$=235 nm, $\epsilon$=34100; $\lambda_2$=287 nm, $\epsilon$=5750

Example 18

Synthesis of Compound 18 N-(2-(methoxy(methyl)amino)-2-oxoethyl)-2-naphthamide

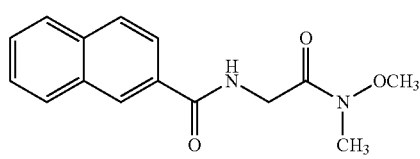

N-(2-(methoxy(methyl)amino)-2-oxoethyl)-2-naphthamide

To a mixture of 2-naphthoic acid (5.8 g, 33.7 mmol), 2-amino-N-methoxy-N-methylacetamide (Gly Weinreb amide; prepared from Boc-Gly Weinreb amide 27 as in the alternate procedure of Example 22) (3.8 g, 32.1 mmol) and DIPEA (12.0 mL, 68.9 mmol) in DCM (70 mL) was added BOP (14.9 g, 33.7 mmol) in one portion at room temperature. The resulting mixture was stirred for 1 hr then saturated NaHCO$_3$ aqueous solution was added. The organic layer was washed with brine (5×60 mL) and 1 N HCl (2×30 mL), dried over MgSO$_4$, filtered and concentrated under reduced pressure to give the crude product 18, which was used in the next reaction without further purification.

Example 19

Synthesis of Compound 19 N-(2-(methoxy(methyl)amino)-2-oxoethyl)-2-naphthamide

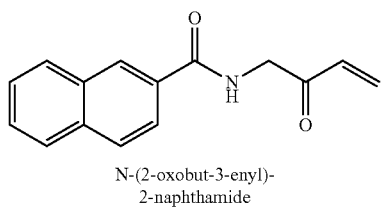

N-(2-oxobut-3-enyl)-2-naphthamide

To a solution of 18 (3.5 g, 12.85 mmol) in dry THF (10 mL) was added a solution of vinylmagnesium bromide in THF (1 M, 31 mL) slowly at 0° C. After addition, the resulting mixture was stirred at room temperature for 1 hr then was poured into an icy 1 N HCl solution (50 mL). The aqueous layer was extracted with DCM (3×80 mL) and the combined organic layers were dried over MgSO$_4$, filtered and concentrated under reduced pressure to give the crude α,β-unsaturated ketone 19.

MS (ESI) 240 (M+1); HPLC $t_R$ 5.46 min.

Example 20

Synthesis of Compound 20 N-(4-(3,5-dichlorobenzylamino)-2-oxobutyl)-2-naphthamide

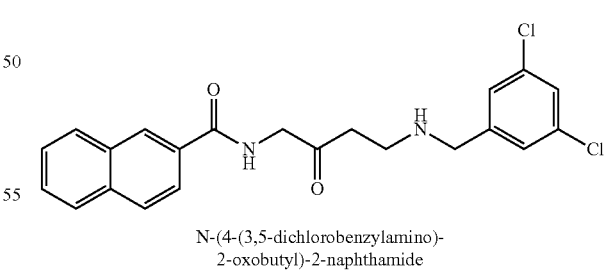

N-(4-(3,5-dichlorobenzylamino)-2-oxobutyl)-2-naphthamide

To a solution of 3,5-dichlorobenzylamine (12 mg, 0.068 mmol) in DCM (0.2 mL) was added a solution of α,β-unsaturated ketone 19 (13 mg, 0.054 mmol) in DCM (0.5 mL) at room temperature. The resulting mixture was stirred until all of the α,β-unsaturated ketone had been consumed (within 1 hr) and then was used for acylation/cyclization reactions without purification. MS (ESI) 415 (M+1); HPLC $t_R$ 6.00 min.

Example 21

Synthesis of Compound 21 allyl 2-(methoxy(methyl)amino)-2-oxoethylcarbamate

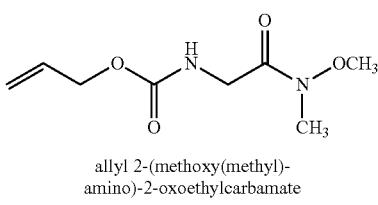

allyl 2-(methoxy(methyl)-
amino)-2-oxoethylcarbamate

To Alloc-glycine (1.45 g, 9.1 mmol) in DCM (20 mL) was added BOP reagent (3.3 g, 7.46 mmol) and DIPEA (1.5 mL, 10.7 mmol). After stirring at room temperature for 10 mins, N,O-dimethylhydroxylamine hydrochloride (0.8 g, 8.2 mmol) and DIPEA (1.5 mL, 10.7 mmol) were added. The reaction was stirred at room temperature overnight. The DCM was removed by rotary evaporation and the residue taken up in EtOAc (100 mL). The organic phase was washed with water (3×100 mL), saturated sodium bicarbonate solution (3×50 mL), water (3×50 mL), 1M hydrochloric acid (3×50 mL), brine (3×50 mL). The organic phase was dried (magnesium sulphate) and the EtOAc removed to give the Weinreb amide 21 as a white solid (0.43 g, 23%).

Alternatively, tert-butyl 2-(methoxy(methyl)amino)-2-oxoethylcarbamate 27 (Boc-Gly Weinreb amide, 1.4 g, 6.4 mmol) in DCM (5 mL) and TFA (3 mL) were stirred at room temperature 1 hr. The solvent was removed under reduced pressure, followed by addition of DCM (20 mL) and then DIPEA until basic. The solution was cooled to 0° C. and allyl chloroformate added (1.4 mL, 13.2 mmol). The reaction was stirred at room temperature overnight. The reaction mixture was neutralised with 1M hydrochloric acid and extracted with EtOAc. The EtOAc was removed by rotary evaporation and the residue was subjected to column chromatography on silica gel using petroleum ether:EtOAc (1:1 to 0:1), providing Weinreb amide 21 (0.86 g, 66%).

Example 22

Synthesis of Compound 22 allyl 2-oxobut-3-enylcarbamate

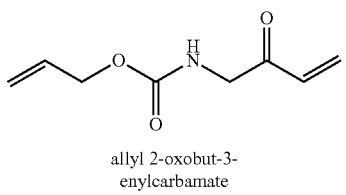

allyl 2-oxobut-3-
enylcarbamate

To the Weinreb amide 21 (0.43 g, 2.1 mmol) in DCM (5 mL) at 0° C. was added vinyl magnesium bromide (10 mmol) in THF (10 mL). The reaction was stirred for 2 hrs and monitored by HPLC. The reaction was added to a mixture of ice and 1M hydrochloric acid (100 mL). The aqueous mixture was extracted with DCM (3×50 mL) and washed with 1M hydrochloric acid (2×100 mL) and water (3×50 mL). The organic phase was dried (magnesium sulphate) and the volume reduced to 50 mL by rotary evaporation. The α,β-unsaturated ketone 22 was stored and used in solution without further purification.

Example 23

Synthesis of Compound 23 (S)-2-(allyloxycarbonylamino)-3-(naphthalen-2-yl)propanoic acid

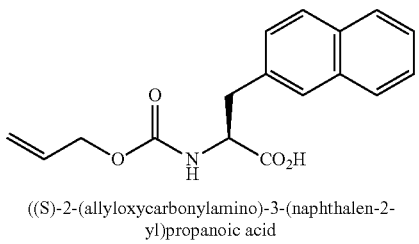

((S)-2-(allyloxycarbonylamino)-3-(naphthalen-2-
yl)propanoic acid

To a stirred mixture of L-3-(2-naphthyl)alanine hydrochloride (5.0 g, 19.8 mmol), $Na_2CO_3$ (7.3 g, 69.3 mmol) and 1,4-dioxane (30 mL) in $H_2O$ (50 mL) was added allylchloroformate (2.1 mL, 19.8 mmol) at 0° C. The resulting mixture was stirred for 16 h then concentrated under reduced pressure. The residue was diluted with ethylacetate (50 mL), and at 0° C. acidified to pH 2. The aqueous phase was extracted with ethylacetate (3×20 mL), the combined organic phase was washed with $H_2O$ (50 mL) and brine (20 mL), dried over $MgSO_4$, filtered and concentrated under reduced pressure to give Aloc-2NaI-OH 23 as a colourless oil (5.8 g, 97%), which was used in the next step without further purification.

HPLC $t_R$ 6.60 min.

Example 24

Synthesis of Compound 24 (S)-allyl 1-(methoxy (methyl)amino)-3-(naphthalen-2-yl)-1-oxopropan-2-ylcarbamate

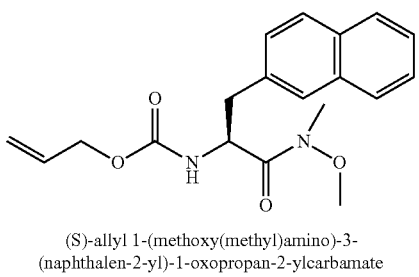

(S)-allyl 1-(methoxy(methyl)amino)-3-
(naphthalen-2-yl)-1-oxopropan-2-ylcarbamate To a stirred mixture of the acid 23 (5.84 g, 19.5 mmol), DIPEA (3.7 mL, 2.09 mmol) and BOP (8.63 g, 19.5 mmol) in DCM (10 mL) was added a pre-mixed solution of N,O-dimethylhydroxylamine hydrochloride (1.9 g, 19.5 mmol) and DIPEA (7.3 mL, 41.6 mmol) in DCM (10 mL) at room temperature. Stirring continued for 16 h the reaction mixture was washed with 1N HCl (3×60 mL), $H_2O$ (3×60 mL), saturated $NaHCO_3$ aqueous solution (3×60 mL) and brine (60 mL), dried over $MgSO_4$. Purification by silica gel chromatography using 20% EtOAc in petroleum ether as eluent gave Weinreb amide 24 (4.83 g, 71%) as a colourless oil. MS (ESI) 343 (M+1); HPLC $t_R$ 7.07 min.

Example 25

Synthesis of Compound 25 (S)-allyl 1-(naphthalen-2-yl)-3-oxopent-4-en-2-ylcarbamate

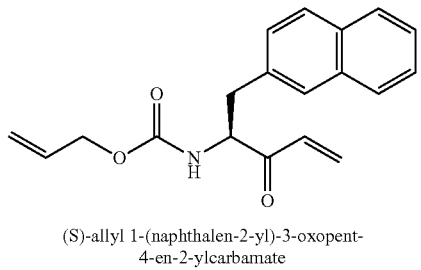

(S)-allyl 1-(naphthalen-2-yl)-3-oxopent-4-en-2-ylcarbamate

At 0° C. a solution of vinylmagnesium bromide in THF (11.5 mL, 1 M) was added in one portion to Weinreb amide 24 (1.58 g, 4.62 mmol) under nitrogen with stirring. The resulting mixture was allowed to stir for 2 h, and poured into a 1N HCl/ice mixture (50 mL). The aqueous mixture was extracted with DCM (3×20 mL), the combined DCM extract was washed with 1N HCl (50 mL), saturated NaHCO$_3$ aqueous solution (50 mL) and brine (20 mL), dried over MgSO$_4$. Solvent was removed under reduced pressure producing the α,β-unsaturated ketone 25 (1.14 g, 80%), which was used in the next step without further purification. MS (ESI) 310 (M+1); HPLC $t_R$ 7.51 min.

Example 26

Synthesis of Compound 26 (S)-allyl 5-(2,2-diphenylethylamino)-1-(naphthalen-2-yl)-3-oxopentan-2-ylcarbamate

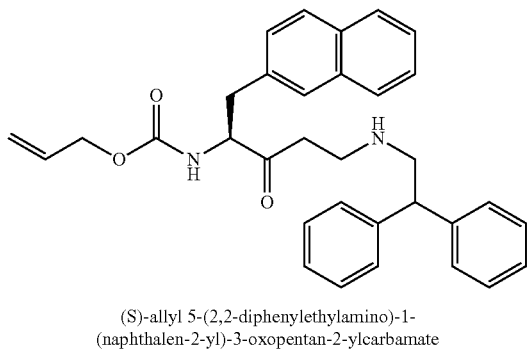

(S)-allyl 5-(2,2-diphenylethylamino)-1-(naphthalen-2-yl)-3-oxopentan-2-ylcarbamate To a stirred solution of 2,2-diphenylethylamine (0.45 g, 2.3 mmol) in DCM (55 mL) was added the vinyl ketone 25 (0.71 g, 2.3 mmol) in one portion. Stirring continued for 2 h, with the reaction mixture used for acylation/cyclization reactions without purification. MS (ESI) 507 (M+1); HPLC $t_R$ 7.22 min.

Example 27

Synthesis of Compound 27 tert-butyl 2-(methoxy(methyl)amino)-2-oxoethylcarbamate (Boc-Gly Weinreb amide)

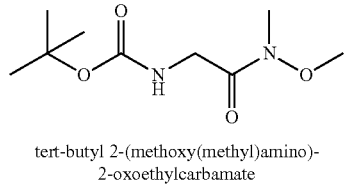

tert-butyl 2-(methoxy(methyl)amino)-2-oxoethylcarbamate

To a stirred mixture of Boc-Gly-OH (20 g, 114.1 mmol), DIPEA (19.8 mL, 114.1 mmol) and BOP (50.5 g, 114.1 mmol) in DCM (20 mL) was added a pre-mixed solution of N,O-dimethylhydroxylamine hydrochloride (11.2 g, 114.1 mmol) and DIPEA (19.8 mL, 114.1 mmol) in DCM (20 mL) at room temperature. The resulting mixture was stirred for 16 h then washed with 1N HCl (3×120 mL), H$_2$O (3×120 mL), saturated NaHCO$_3$ aqueous solution (3×120 mL) and brine (40 mL), dried over MgSO$_4$, filtered and concentrated under reduced pressure to give 27 as a white solid (20 g, 80%), which was used in the next step without further purification.

MS (ESI) 219 (M+1); HPLC $t_R$ 4.12 min.

Example 28

Synthesis of Compound 28 tert-butyl 2-oxobut-3-enylcarbamate

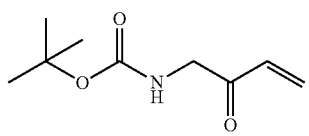

tert-butyl 2-oxobut-3-enylcarbamate

At 0° C. a solution of vinylmagnesium bromide in THF (184 mL, 1 M) was added in one portion to Weinreb amide 27 (20 g, 91.6 mmol) under nitrogen with stirring. The resulting mixture was allowed to stir for 2 h, and poured into a 1N HCl/ice mixture (400 mL). The aqueous mixture was extracted with DCM (5×100 mL), the combined DCM extract was washed with 1N HCl (2×100 mL), saturated NaHCO$_3$ aqueous solution (100 mL) and brine (100 mL), then dried over MgSO$_4$. Solvent was removed under reduced pressure gave the ketone 28 (12.9 g, 76%) as a pale yellow oil, which was used in the next step without further purification. MS (ESI) 186 (M+1); HPLC $t_R$ 4.19 min.

Example 29

Synthesis of Compound 29 tert-butyl 4-(2,2-diphenylethylamino)-2-oxobutylcarbamate

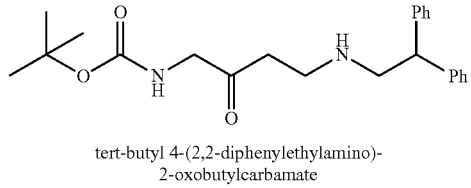

tert-butyl 4-(2,2-diphenylethylamino)-
2-oxobutylcarbamate

To a stirred solution of 2,2-diphenylethylamine (0.33 g, 1.66 mmol) in DCM (10 mL) was added α,β-unsaturated ketone 28 (0.31 g, 1.66 mmol) at room temperature. Stirring continued for 2 h; the crude reaction mixture of 29 was used for acylation/cyclization reactions without purification. MS (ESI) 383 (M+1); HPLC $t_R$ 5.98 min

Example 30

Synthesis of Compound 30 (S)-tert-butyl 3-methyl-4, 8-dioxo-10-phenyl-2,9-dioxa-3,7-diazadecane-6-carboxylate

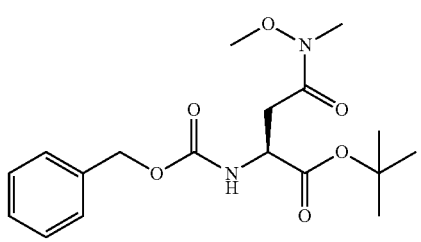

(S)-tert-butyl 3-methyl-4,8-
dioxo-10-phenyl-2,9-dioxa-3,7-
diazadecane-6-carboxylate To a suspension of Cbz-L-Asp-OtBu DCHA salt (10.1 g, 20.0 mmol), N,O-dimethylhydroxylamine·HCl (5.9 g, 60.5 mmol) and DIPEA (12.0 mL, 68.9 mmol) in DCM (150 mL) was added BOP (10.6 g, 24.0 mmol) in one portion at room temperature. The resulting suspension was stirred for 3 hrs then H$_2$O (100 mL) was added. The organic layer was washed with 1 N HCl (2×100 mL), saturated NaHCO$_3$ aqueous solution (2×100 mL) and brine (3×100 mL) and then dried over MgSO$_4$, filtered and concentrated under reduced pressure to give the crude product. Purification by flash chromatography on silica gel (PET ether/EtOAc 1:2) gave 30 (6.4 g, 87%) as a colorless oil. MS (ESI) 367 (M+1); HPLC $t_R$ 6.87 min.

Example 31

Synthesis of Compound 31 (S)-3-methyl-4,8-dioxo-10-phenyl-2,9-dioxa-3,7-diazadecane-6-carboxylic acid

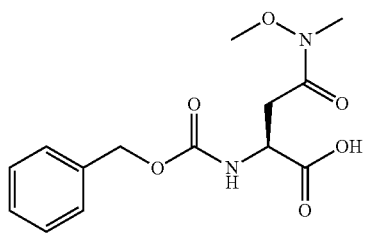

(S)-3-methyl-4,8-dioxo-10-
phenyl-2,9-dioxa-3,7-
diazadecane-6-carboxylic aacid

Compound 30 (300 mg, 0.82 mmol) was dissolved in a TFA/DCM (1:1) solution (2 mL) and the resulting mixture was stirred at room temperature for 2 hrs. The solvents were removed under reduced pressure and the residue was re-dissolved in DCM (10 mL). This solution was washed with 1 N HCl (1×10 mL) and the organic layer was dried over MgSO$_4$, filtered and concentrated under reduced pressure to give the crude product 31 (235 mg, 92%), which was used in the next reaction without further purification. MS (ESI) 311 (M+1); HPLC. $t_R$ 4.96 min.

Example 32

Synthesis of Compound 32 (S)-benzyl 8-(2,2-diphenylethyl)-3,16,16-trimethyl-4,7,11,14-tetraoxo-2,15-dioxa-3,8,13-triazaheptadecan-6-ylcarbamate

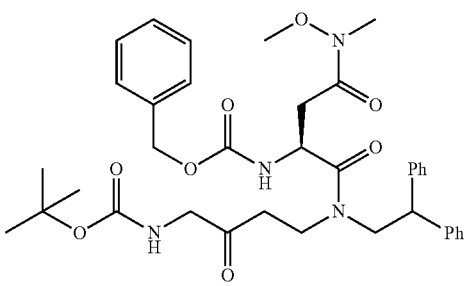

(S)-benzyl 8-(2,2-diphenylethyl)-3,16,16-
trimethyl-4,7,11,14-tetraoxo-2,15-dioxa-3,8,13-
triazaheptadecan-6-ylcarbamate Compound 32 was prepared from Compounds 29 and 31 following the procedure of Example 14. MS (ESI) 675 (M+1); HPLC $t_R$ 8.31 min.

Example 33

Synthesis of Compound 33 tert-butyl((3S,5S)-1-(2,2-diphenylethyl)-3-(2-(methoxy(methyl)amino)-2-oxoethyl)-2-oxo-1,4-diazepan-5-yl)methylcarbamate

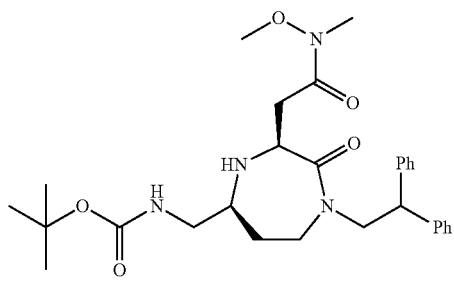

tert-butyl ((3S,5S)-1-(2,2-diphenylethyl)-3-(2-(methoxy(methyl)amino)-2-oxoethyl)-2-oxo-1,4-diazepan-5-yl)methylcarbamate A mixture of crude 32 (350 mg) and 5% Pd/C (200 mg) in 2-propanol (15 mL) was shaken at room temperature under hydrogen (30 psi) for 24 hrs. The mixture was then filtered through a pad of Celite and the filtrate was concentrated under reduced pressure to give the crude product. Purification by flash chromatography on silica gel (100% of EtOAc) gave 33 (175 mg, 65% over 3 steps) as a white solid. MS (ESI) 525 (M+1); HPLC $t_R$ 6.24 min.

Example 34

Synthesis of Compound 34 2-((2S,7S)-7-(aminomethyl)-4-(2,2-diphenylethyl)-3-oxo-1,4-diazepan-2-yl)-N-methoxy-N-methylacetamide

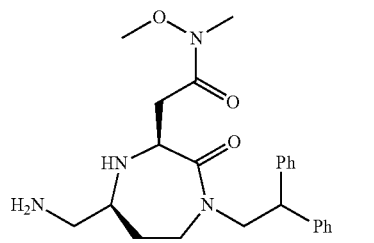

2-((2S,7S)-7-(aminomethyl)-4-(2,2-diphenylethyl)-3-oxo-1,4-diazepan-2-yl)-N-methoxy-N-methylacetamide Compound 33 (175 mg, 0.333 mmol) was dissolved in a TFA/DCM (1:1) solution (1 mL) and the resulting mixture was stirred at room temperature for 2 hrs. The solvents were removed under reduced pressure and the residue was re-dissolved in EtOAc (20 mL). Saturated NaHCO₃ aqueous solution (10 mL) and brine (10 mL) were added to the above solution and the aqueous layer was extracted with EtOAc (9×20 mL). The combined organic layers were dried over MgSO₄, filtered and concentrated under reduced pressure to give the crude product 34 (120 mg, 85%) as a yellow solid, which was used in the next reaction without further purification. MS (ESI) 425 (M+1); HPLC $t_R$ 5.20 min.

Example 35

Synthesis of Compound 35 N-(((3S,5S)-1-(2,2-diphenylethyl)-3-(2-(methoxy(methyl)amino)-2-oxoethyl)-2-oxo-1,4-diazepan-5-yl)methyl)-6-fluoro-2-naphthamide

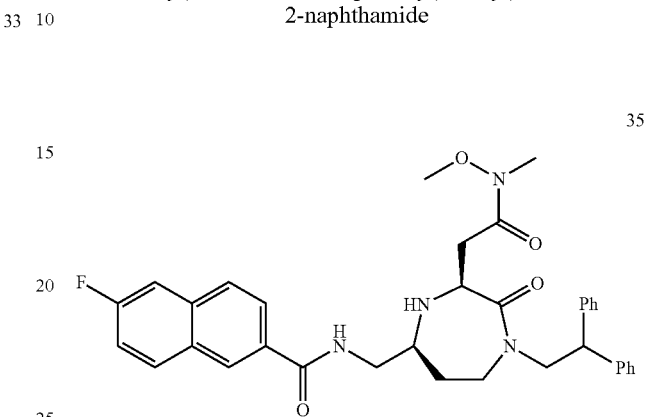

N-(((3S,5S)-1-(2,2-diphenylethyl)-3-(2-(methoxy(methyl)amino)-2-oxoethyl)-2-oxo-1,4-diazepan-5-yl)methyl)-6-fluoro-2-naphthamide To a solution of 34 (50 mg, 0.118 mmol) and 6-fluoro-2-naphthoic acid (27 mg, 0.142 mmol) in DCM (4 mL) was added DIC (22 µl, 0.142 mmol) at room temperature. The resulting mixture was stirred for 2 hrs then the solvent was removed under reduced pressure to give the crude product. Purification by flash chromatography on silica gel (eluting with Petroleum ether:EtOAc (1:1) then EtOAc) gave 35 (29 mg, 41%) as a white solid. MS (ESI) 597 (M+1); HPLC $t_R$ 6.75 min.

Example 36

Synthesis of Compound 36 N-(((3S,5S)-1-(2,2-diphenylethyl)-2-oxo-3-(2-oxoethyl)-1,4-diazepan-5-yl)methyl)-6-fluoro-2-naphthamide

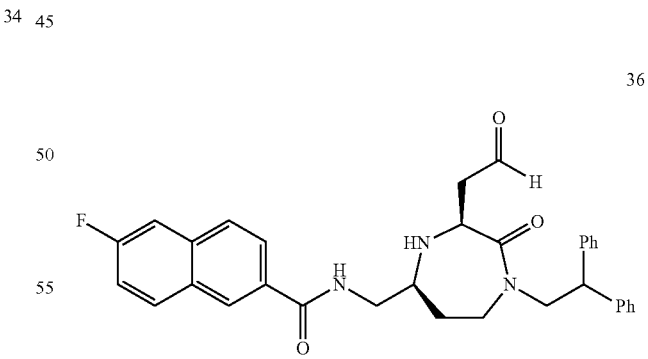

N-(((3S,5S)-1-(2,2-diphenylethyl)-2-oxo-3-(2-oxoethyl)-1,4-diazepan-5-yl)methyl)-6-fluoro-2-naphthamide To a solution of 35 (29 mg, 0.049 mmol) in dry THF (1 mL) was added LiAlH(OtBu)₃ (38 mg, 0.145 mmol) in one portion at room temperature and the resulting suspension was stirred overnight. This suspension was then slowly poured into a cold (0° C.) 0.4 M KHSO₄ aqueous solution (2 mL, 0.8 mmol) and the resulting mixture was diluted with EtOAc (3 mL). The aqueous layer was extracted with EtOAc (3×3 mL) and the combined organic layers were washed with 1 N HCl (3×6 mL), saturated NaHCO₃ aqueous solution (1×6 mL), and brine (1×6 mL). The organic solution was then dried over MgSO₄, filtered and concentrated under reduced pressure to give 36 (24 mg, 91%). MS (ESI) 538 (M+1); HPLC $t_R$ 6.41 min.

Example 37

Synthesis of Boc-L-Glu(piperidine)-OH 37 (S)-2-(tert-butoxycarbonylamino)-5-oxo-5-(piperidin-1-yl)pentanoic acid

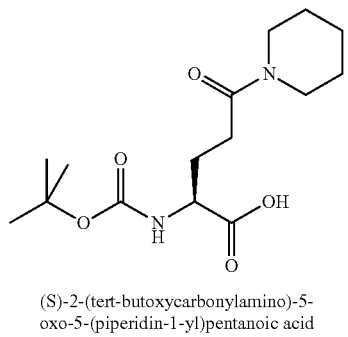

(S)-2-(tert-butoxycarbonylamino)-5-oxo-5-(piperidin-1-yl)pentanoic acid

HATU (2.5 g) and DIPEA (1.5 mL) was added to Boc-L-Glu(OH)—OBn (2.0 g) in DCM (50 mL), stirred for 10 min, then piperidine (0.7 mL) was added and the reaction stirred overnight at room temperature. The reaction was washed with sodium bibicarbonate solution (2×), saturated NH₄Cl (2×), brine (2×), dried over MgSO₄, filtered, and evaporated to give 2.9 g of Boc-L-Glu(piperidine)-OBn. The benzyl ester (0.6 g) was dissolved in EtOH (15 mL) with catalytic Pd/C and hydrogenated for 1 h, filtered over Celite, and the EtOH evaporated by rotary evaporation to give 0.51 g of 37.

Example 38

Synthesis of Compound 38 1-phenyl-9-(2,2-diphenylethyl)-3,6,10-trioxo-2,11-dioxa-4,9-diazatetradec-13-ene

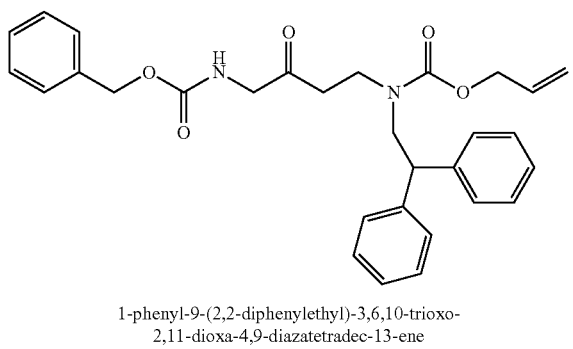

1-phenyl-9-(2,2-diphenylethyl)-3,6,10-trioxo-2,11-dioxa-4,9-diazatetradec-13-ene 2,2-Diphenylethylamine (412 mg, 2.09 mmol) was added to a solution of Cbz-vinylketone 13 (1.9 mmol) in DCM (40 mL). After 5 min Alloc-Cl (0.41 mL, 3.80 mmol) and DIPEA (0.99 mL, 5.70 mmol) were added and the reaction stirred for a further 1 h. The solution was washed with sat. NaHCO₃ and evaporated to dryness to give a brown oil. Purification by column chromatography (SiO₂ gel, pet. ether/EtOAc) gave 815 mg of 38.

Example 39

Synthesis of Compound 39 (S)-allyl 2-amino-3-(pyridin-2-yl)propanoate

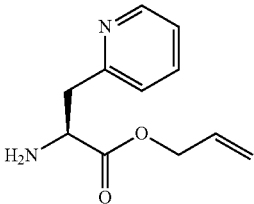

(S)-allyl 2-amino-3-(pyridin-2-yl)propanoate

To a solution of Boc-L-3-(2-pyridyl)-Ala-OH (810 mg, 3.04 mmol) in DCM (12 mL) was added allyl alcohol (0.31 mL, 4.56 mmol) followed by HATU (1736 mg, 4.57 mmol) and DIPEA (0.79 mL, 4.57 mmol). After stirring for 2 h the solution was concentrated and half the mixture purified by column chromatography (SiO₂ gel, pet. ether/EtOAc) to give 670 mg of Boc-L-3-(2-pyridyl)-Ala-Oallyl. A portion of this product (290 mg, 0.95 mmol) was dissolved in DCM (3 mL) and TFA (3 mL) and stirred for 5 min. The solution was concentrated, then DCM was added, washed with sat. NaHCO₃, and evaporated to dryness to give 39 as a colourless oil (280 mg) which was used without purification in the next step.

Example 40

Synthesis of Compound 40 (2S)-allyl 2-(9-(2,2-diphenylethyl)-3,10-dioxo-1-phenyl-2,11-dioxa-4,9-diazatetradec-13-en-6-ylamino)-3-(pyridin-2-yl)propanoate

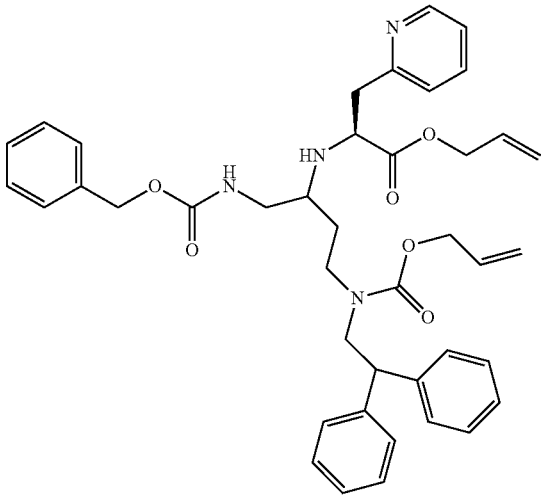

(2S)-allyl 2-(9-(2,2-diphenylethyl)-3,10-dioxo-1-phenyl-2,11-dioxa-4,9-diazatetradec-13-en-6-ylamino)-3-(pyridin-2-yl)propanoate The protected aminoketone 38 (474 mg, 0.95 mmol), L-3-(2-pyridyl)-Ala-Oallyl 39 (0.95 mmol) and NaBH(OAc)₃ (403 mg, 1.90 mmol) in DCM (6.7 mL) were stirred for 17 h. Saturated NaHCO₃ was added, extracted with DCM (3×), and the organic extracts combined and washed with saturated NaHCO₃ and H₂O, dried over MgSO₄, and evaporated to dryness to give 40 (810 mg) as pale yellow oil (as a mixture of diastereoisomers), which was used in the next reaction without purification.

Example 41

Synthesis of Compound 41 (2S)-2-(1-(benzyloxycarbonylamino)-4-(2,2-diphenylethylamino)butan-2-ylamino)-3-(pyridin-2-yl)propanoic acid

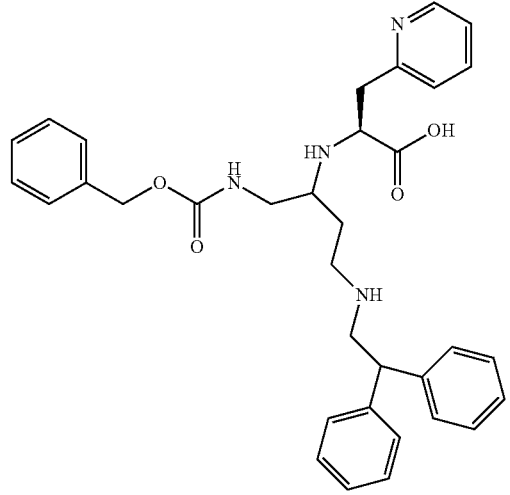

(2S)-2-(1-(benzyloxycarbonylamino)-4-(2,2-diphenylethylamino)butan-2-ylamino)-3-(pyridin-2-yl)propanoic acid The Alloc/allyl protected derivative 40 (656 mg, 0.95 mmol) was dissolved in DCM (10 mL) and the solution degassed under vacuum. 1,3-Dimethylbarbituric acid (296 mg, 1.90 mmol) and catalytic Pd(PPh$_3$)$_4$ (220 mg, 0.19 mmol) were added, and the reaction stirred for 1 h to give a solution of deprotected 41, which was used in the next step without purification.

Example 42

Synthesis of Compounds 42 and 43: benzyl((3S,5S)-1-(2,2-diphenylethyl)-2-oxo-3-(pyridin-2-ylmethyl)-1,4-diazepan-5-yl)methylcarbamate and benzyl((3S,5R)-1-(2,2-diphenylethyl)-2-oxo-3-(pyridin-2-ylmethyl)-1,4-diazepan-5-yl)methylcarbamate

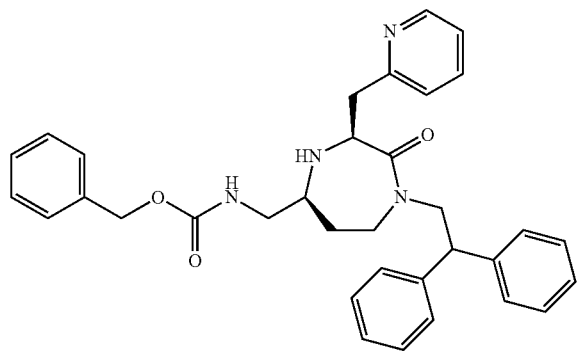

benzyl ((3S,5S)-1-(2,2-diphenylethyl)-2-oxo-3-(pyridin-2-ylmethyl)-1,4-diazepan-5-yl)methylcarbamate

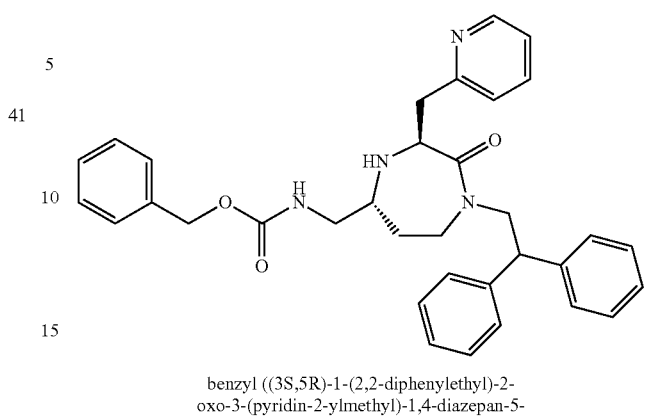

benzyl ((3S,5R)-1-(2,2-diphenylethyl)-2-oxo-3-(pyridin-2-ylmethyl)-1,4-diazepan-5-yl)methylcarbamate To the crude deprotected 41 (0.95 mmol) in DCM (10 mL) was added HATU (541 mg, 1.43 mmol) followed by DIPEA (0.50 mL, 2.85 mmol). After 30 min the solution was washed (sat. NaHCO$_3$, brine), dried (MgSO$_4$), and evaporated. The two diastereomeric products were separated by column chromatography (SiO$_2$ gel, pet. ether/EtOAc) to give 260 mg of the earlier eluting (3S,5S) isomer 42, and 175 mg of the later eluting (3S,5R) isomer 43.

Example 43

Synthesis of Compound 44 (3S,5S)-5-(aminomethyl)-1-(2,2-diphenylethyl)-3-(pyridin-2-ylmethyl)-1,4-diazepan-2-one

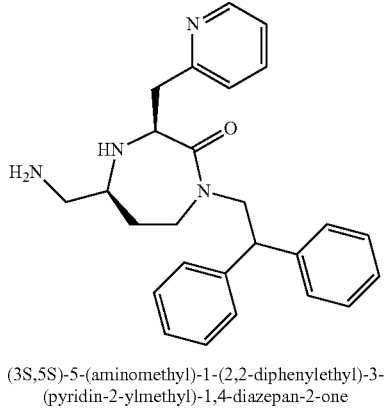

(3S,5S)-5-(aminomethyl)-1-(2,2-diphenylethyl)-3-(pyridin-2-ylmethyl)-1,4-diazepan-2-one The Cbz group of the preferred diastereomer 42 was removed by hydrogenation (H$_2$, 1 atm) of a suspension of 42 (35 mg) and Pd/C (50 mg) in EtOAc/methanol overnight. The solution was filtered through Celite and evaporated to give 44 as a colourless oil (25 mg).

Example 44

Synthesis of Compound 45 (E)-3-(4-chlorophenyl)-N-(((3S,5S)-1-(2,2-diphenylethyl)-2-oxo-3-(pyridin-2-ylmethyl)-1,4-diazepan-5-yl)methyl)acrylamide

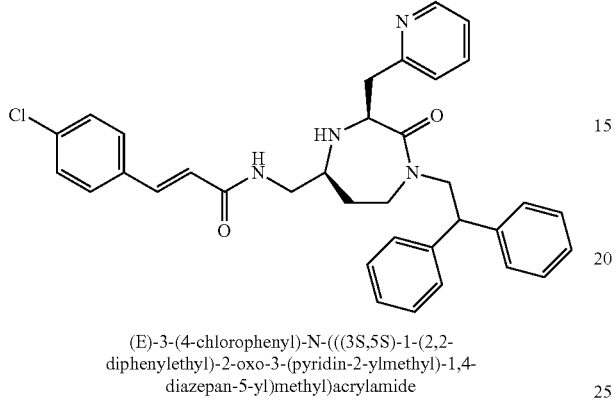

(E)-3-(4-chlorophenyl)-N-(((3S,5S)-1-(2,2-diphenylethyl)-2-oxo-3-(pyridin-2-ylmethyl)-1,4-diazepan-5-yl)methyl)acrylamide To the crude free amine 44 (25 mg, 0.06 mmol) in DCM was added 4-chlorocinnamic acid (13 mg, 0.07 mmol), DIPEA (25 μL, 0.14 mmol) and BOP (31 mg, 0.07 mmol). After stirring overnight the solution was washed (sat. NaHCO$_3$, brine), dried (MgSO$_4$), and evaporated under high vacuum, and the residue purified by preparative HPLC to give 30 mg of 45. MS (ESI) 579.3 (M+1); HPLC $t_R$ 6.60 min.

Example 45

Syntheses of Compounds 46-80

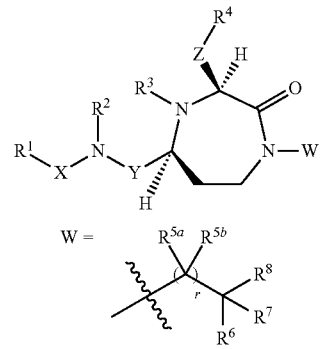

Compounds 17 and 45-80, with substituents as identified in Table 1, were prepared as in the previous examples according to the routes identified in Schemes 1-5, as summarized in Table 2, with experimental properties summarized in Table 3.

TABLE 1

Identity of Compounds

| Cpd. | R$^1$X | R$^2$ | R$^3$ | Y | ZR$^4$ | W |
|---|---|---|---|---|---|---|
| 17 | 6-chloro-2-naphthoyl | H | H | CH$_2$ | CH$_2$CH$_2$iPr | (S)-2-phenylbutyl |
| 45 | 4-chlorocinnamoyl | H | H | CH$_2$ | CH$_2$(2-pyridinyl) | 2,2-diphenylethyl |
| 46 | 2-naphthoyl | H | H | CH$_2$ | (CH$_2$)$_2$ONHC(=NH)NH$_2$ | 2,2-diphenylethyl |
| 47 | 2-naphthoyl | H | H | CH$_2$ | CH$_2$(3-pyridinyl) | 2,2-diphenylethyl |
| 48 | 2-naphthoyl | H | H | CH$_2$ | CH$_2$(4-pyridinyl) | 2,2-diphenylethyl |
| 49 | 2-naphthoyl | H | H | CH$_2$ | (CH$_2$)$_3$CH$_3$ | 2,2-diphenylethyl |
| 50 | 4-chlorocinnamoyl | H | H | CH$_2$ | (CH$_2$)$_3$CH$_3$ | 2,2-diphenylethyl |
| 51 | 4-chlorocinnamoyl | H | H | CH$_2$ | (CH$_2$)$_2$CONH$_2$ | 2,2-diphenylethyl |
| 52 | 2-naphthoyl | H | H | CH$_2$ | (CH$_2$)$_2$CONH$_2$ | 2,2-diphenylethyl |
| 53 | 2-naphthoyl | H | H | CH$_2$ | CH$_2$cyclohexyl | 2,2-diphenylethyl |
| 54 | 4-chlorocinnamoyl | H | H | CH$_2$ | CH$_2$cyclohexyl | 2,2-diphenylethyl |
| 55 | 2-naphthoyl | H | H | CH$_2$ | (CH$_2$)$_2$CO(1-piperidinyl) | 2,2-diphenylethyl |
| 56 | 4-chlorocinnamoyl | H | H | CH$_2$ | (CH$_2$)$_2$CO(1-piperidinyl) | 2,2-diphenylethyl |
| 57 | 2-naphthoyl | H | H | CH$_2$ | (CH$_2$)$_2$Ph | 2,2-diphenylethyl |
| 58 | 4-chlorocinnamoyl | H | H | CH$_2$ | (CH$_2$)$_2$Ph | 2,2-diphenylethyl |
| 59 | 2-naphthoyl | H | H | CH$_2$ | (CH$_2$)$_2$cyclohexyl | 2,2-diphenylethyl |
| 60 | 4-chlorocinnamoyl | H | H | CH$_2$ | (CH$_2$)$_2$cyclohexyl | 2,2-diphenylethyl |
| 61 | 2-naphthoyl | H | H | CH$_2$ | CH$_2$Ph | 2,2-diphenylethyl |
| 62 | 4-chlorocinnamoyl | H | H | CH$_2$ | CH$_2$Ph | 2,2-diphenylethyl |
| 63 | 4-chlorocinnamoyl | H | H | CH$_2$ | CH$_2$(imidazol-3-yl) | 2,2-diphenylethyl |
| 64 | 4-chlorocinnamoyl | H | H | CH$_2$ | CH$_2$CONH(2-pyridyl) | 2,2-diphenylethyl |
| 65 | 4-chlorocinnamoyl | H | H | CH$_2$ | CH$_2$CO(1-piperidinyl) | 2,2-diphenylethyl |
| 66 | 6-chloro-2-naphthoyl | H | H | CH$_2$ | (CH$_2$)$_2$CO(1-piperidinyl) | (S)-2-phenylbutyl |
| 67 | 3,4-dichlorobenzoyl | H | H | CH$_2$ | (CH$_2$)$_2$CO(1-piperidinyl) | (S)-2-phenylbutyl |
| 68 | 4-chlorocinnamoyl | H | H | CH$_2$ | CH$_2$(2-NH$_2$—Ph) | 2,2-diphenylethyl |
| 69 | 2-naphthoyl | H | H | CH$_2$ | CH$_2$(2-NH$_2$—Ph) | 2,2-diphenylethyl |
| 70 | 6-chloro-2-naphthoyl | H | H | CH$_2$ | (CH$_2$)$_3$CH$_3$ | (S)-2-phenylbutyl |
| 71 | 2-naphthoyl | H | H | CH$_2$ | CH$_2$(2-(piperidin-1-yl)phenyl)- | 2,2-diphenylethyl |
| 72 | 2-naphthoyl | H | H | CH$_2$ | (CH$_2$)$_2$CON(Me)nBu | (S)-2-phenylbutyl |
| 73 | 2-naphthoyl | H | H | CH$_2$ | (CH$_2$)$_2$CONHcHex | (S)-2-phenylbutyl |
| 74 | 6-chloro-2-naphthoyl | H | H | CH2 | (CH$_2$)$_2$cHex | (S)-2-phenylbutyl |
| 75 | 6-chloro-2-naphthoyl | H | H | CH2 | nHex | (S)-2-phenylbutyl |
| 76 | 6-chloro-2-naphthoyl | H | H | CH$_2$ | (CH$_2$)$_4$OH | (S)-2-phenylbutyl |
| 77 | 6-chloro-2-naphthoyl | H | H | CH$_2$ | (CH$_2$)$_2$OMe | (S)-2-phenylbutyl |

TABLE 1-continued

Identity of Compounds

| Cpd. | R¹X | R² | R³ | Y | ZR⁴ | W |
|---|---|---|---|---|---|---|
| 78 | 6-chloro-2-naphthoyl | H | H | CH₂ | (CH₂)₂OBn | (S)-2-phenylbutyl |
| 79 | 6-chloro-2-naphthoyl | H | H | CH₂ | iBu | (S)-2-phenylbutyl |
| 80 | 3,4-dichlorobenzoyl | H | H | CH₂ | (CH₂)₂OH | (S)-2-phenylbutyl |

TABLE 2

Synthesis of Compounds

| Cpd. | Route to A | Scheme 1: VN(R²)—Y—CO₂H | P²NH—CH(U)—CO₂H | Conversion of A to Product | U modification |
|---|---|---|---|---|---|
| 17 | Scheme 1 | Cbz-Gly-OH | Fmoc-L-HoLeu-OH | Scheme 4 | none |
| 45 | Scheme 2 | Cbz-Gly-OH | H-β-(2-pyridyl)-L-Ala-Oallyl | Scheme 4 | none |
| 46 | Scheme 1 | Alloc-Gly-OH | Boc-L-Canavanine (Fmoc)-OH | Scheme 4 | P3 deprotection |
| 47 | Scheme 1 | 2-naphthoic-Gly-OH | Fmoc-L-3-PyridylAla-OH | Scheme 3 | none |
| 48 | Scheme 1 | 2-naphthoic-Gly-OH | Fmoc-L-4-PyridylAla-OH | Scheme 3 | none |
| 49 | Scheme 1 | Cbz-Gly-OH | Boc-L-Nle-OH | Scheme 4 | none |
| 50 | Scheme 1 | Cbz-Gly-OH | Boc-L-Nle-OH | Scheme 4 | none |
| 51 | Scheme 1 | Cbz-Gly-OH | Boc-L-Gln-OH | Scheme 4 | none |
| 52 | Scheme 1 | Cbz-Gly-OH | Boc-L-Gln-OH | Scheme 4 | none |
| 53 | Scheme 1 | Cbz-Gly-OH | Boc-L-Cha-OH | Scheme 4 | none |
| 54 | Scheme 1 | Cbz-Gly-OH | Boc-L-Cha-OH | Scheme 4 | none |
| 55 | Scheme 1 | Cbz-Gly-OH | Boc-L-Glu(1-piperidinyl)-OH | Scheme 4 | none |
| 56 | Scheme 1 | Cbz-Gly-OH | Boc-L-Glu(1-piperidinyl)-OH | Scheme 4 | none |
| 57 | Scheme 1 | Cbz-Gly-OH | Boc-L-Hfe-OH | Scheme 4 | none |
| 58 | Scheme 1 | Cbz-Gly-OH | Boc-L-Hfe-OH | Scheme 4 | none |
| 59 | Scheme 1 | Cbz-Gly-OH | Boc-L-hCha-OH | Scheme 4 | none |
| 60 | Scheme 1 | Cbz-Gly-OH | Boc-L-hCha-OH | Scheme 4 | none |
| 61 | Scheme 1 | Cbz-Gly-OH | Boc-L-Phe-OH | Scheme 4 | none |
| 62 | Scheme 1 | Cbz-Gly-OH | Boc-L-Phe-OH | Scheme 4 | none |
| 63 | Scheme 1 | Cbz-Gly-OH | Fmoc-L-His(Boc)-OH | Scheme 4 | P3 deprotection |
| 64 | Scheme 1 | Cbz-Gly-OH | Fmoc-L-Asp(OtBu)-OH | Scheme 4 | P3 deprotection, amidation |
| 65 | Scheme 1 | Cbz-Gly-OH | Fmoc-L-Asp(OtBu)-OH | Scheme 4 | P3 deprotection, amidation |
| 66 | Scheme 1 | Cbz-Gly-OH | Boc-L-Gln(piperidyl)-OH | Scheme 4 | none |
| 67 | Scheme 1 | Cbz-Gly-OH | Boc-L-Gln(piperidyl)-OH | Scheme 4 | none |
| 68 | Scheme 1 | Fmoc-Gly-OH | Boc-L-(2-NO2)-Phe-OH | Scheme 5 | nitro hydrogenation |
| 69 | Scheme 1 | Fmoc-Gly-OH | Boc-L-(2-NO2)-Phe-OH | Scheme 5 | nitro hydrogenation |
| 70 | Scheme 1 | Cbz-Gly-OH | Boc-L-Nle-OH | Scheme 4 | none |
| 71 | Scheme 1 | Fmoc-Gly-OH | Boc-L-(2-NO2)-Phe-OH | Scheme 5 | nitro hydrogenation then dialkylation with alkyl dibromide |
| 72 | Scheme 1 | 2-naphthoic-Gly | Boc-L-Gln(Me,nBu)-OH | Scheme 4 | none |
| 73 | Scheme 1 | 2-naphthoic-Gly | Boc-L-Gln(chex)-OH | Scheme 4 | none |
| 74 | Scheme 1 | Cbz-Gly | Fmoc-L-HoCha-OH | Scheme 4 | none |
| 75 | Scheme 1 | Cbz-Gly | Fmoc-L-2-aminooctanoic acid | Scheme 4 | none |
| 76 | Scheme 1 | Cbz-Gly | Boc-L-5-HO-Nle-OH | Scheme 4 | none |
| 77 | Scheme 1 | Cbz-Gly | Fmoc-L-HoSer(Me)-OH | Scheme 4 | none |
| 78 | Scheme 1 | Alloc-Gly | Boc-L-HoSer(Bzl)-OH | Scheme 4 | none |
| 79 | Scheme 1 | Cbz-Gly | Boc-L-Leu-OH | Scheme 4 | none |
| 80 | Scheme 1 | Boc-Gly | Cbz-L-Asp[N(Me)OMe] | Scheme 4 | P3 conversion to aldehyde then reduction |

Example 46

Human MC5R Radioligand Binding Assay

Assessments of compound binding to human MC5R (hMC5R) by displacement of an $^{125}$I-labeled NDP-MSH receptor ligand peptide were performed essentially as described in the data sheets produced by Perkin Elmer to accompany their frozen hMC5R membranes (Perkin Elmer catalog number RBXMC5M400UA).

[$^{125}$I] NDP-MSH: Radiolabeled in House and Purified by HPLC:

Na$^{125}$I (0.5 mCi, 17.4 Ci/mg) was added to 50 μL sodium phosphate (50 mM, pH 7.4) in an eppendorf tube precoated with IODOGEN. After incubation for 10 mins the phosphate buffer containing the iodine was added to NDP-MSH (10 ul at 1 mg/mL) in a separate eppendorf tube. This was incubated for a further 10 mins. The iodinated NDP-MSH was purified by HPLC on a Zorbax SB 300 column using solvent A: 0.05% TFA and solvent B: 90% acetonitrile 0.045% TFA with a linear gradient, 0-67% B over 60 mins. The $^{125}$I NDP-MSH eluted at 52 min after the unlabeled starting material (48 min) and was counted and stored in the freezer. It was used within 48 hrs, as radioactive decay and ligand decomposition resulted in greatly reduced specific binding observed after 72 hrs.

Reagents:

Incubation buffer: 25 mM HEPES-KOH (pH 7.0), 1.5 mM $CaCl_2$, 1 mM $MgSO_4$, 0.1 M NaCl, 1 mM 1,10-phenanthroline, and 1 Complete™ protease inhibitor tablet/100 mL (Roche, catalog number 1873580)

Perkin Elmer frozen hMC5 membranes: catalog number RBXMC5M400UA, 0.4 mL/vial; 400 microassays/vial. 0.78 mg/mL protein concentration Vials of frozen membranes were thawed rapidly immediately before use, diluted with binding buffer and vortexed. Resuspended membranes were kept on ice until they were added to the wells of the plate.

Binding Protocol for 400 Microassays Per Vial:

Assays were performed in 96 well polypropylene plates. Membranes (0.78 µg 40 µL of a 1:40 dilution in incubation buffer) were added to [$^{125}$I] NDP-MSH (0.84 nM; 2200 Ci/mmol) and test compounds in a total volume of 140 µL. This was incubated for 1 hr at 37° C. Non-specific binding was determined with 3 mM NDP-MSH. Plates were filtered using a Tomtec cell harvester with GF/A filters (Wallac) (presoaked in 0.6% polyethylenimine) and washed three times with 1.0 mL ice-cold wash buffer (the above incubation buffer without 1,10-phenanthroline and Complete™ protease inhibitor tablet). The filters were dried in a 37° C. oven, placed in a sample bag and 5 mL Betaplatescint (Wallac) was added. Prepared filters were counted in cassettes in a Microbeta Trilux (Wallac) for 1 min. Non-specific binding just under 5%. Data analysis was performed using GraphPad Prism 4, employing competition binding with a single site model and a fixed Hill coefficient. The following equation was used: Y=Bottom+(Top-Bottom)/$^{1}/_{10}$^(X-log $EC_{50}$), where X=log(concentration) and Y=binding to fit the data.

Example 47

Activity of Selected Compounds: hMC5R Binding

Representative compounds of the present invention were tested for binding in the hMC5R assay as in Example 46, as listed in Table 3. The compounds were tested as their trifluoroacetate or hydrochloride salts, or as their free bases.

TABLE 3

Properties of Compounds

| Cpd. | MS (M + 1) | $t_R$ (min) | MC5R radioligand $IC_{50}$ |
|---|---|---|---|
| 17 | 534.3 | 7.66 | xxx |
| 45 | 579.3 | 6.60 | x |
| 46 | 579.3 | 5.83 | xx |
| 47 | 569 | 5.87 | xx |
| 48 | 569 | 5.83 | x |
| 49 | 534 | 7.27 | xx |
| 50 | 544.5 | 7.42 | xx |

TABLE 3-continued

Properties of Compounds

| Cpd. | MS (M + 1) | $t_R$ (min) | MC5R radioligand $IC_{50}$ |
|---|---|---|---|
| 51 | 559.4 | 6.59 | xx |
| 52 | 549.4 | 6.42 | xx |
| 53 | 574.5 | 7.69 | xx |
| 54 | 584.5 | 7.83 | xx |
| 55 | 617.7 | 7.04 | xx |
| 56 | 627.5 | 7.11 | xxx |
| 57 | 582 | 7.44 | xx |
| 58 | 592.4 | 7.55 | xx |
| 59 | 588.4 | 8.00 | xx |
| 60 | 598.4 | 8.15 | xx |
| 61 | 568.1 | 7.28 | xx |
| 62 | 578.3 | 7.45 | xx |
| 63 | 568.1 | 5.91 | x |
| 64 | 622.3 | 6.49 | xx |
| 65 | 613.4 | 7.03 | xx |
| 66 | 603.2 | 7.23 | xxx |
| 67 | 587.2 | 7.01 | x |
| 68 | 593.3 | 6.56 | xx |
| 69 | 583.3 | 6.38 | xx |
| 70 | 520.2 | 7.40 | xx |
| 71 | 651.3 | 6.85 | x |
| 72 | 571.1 | 7.11 | xx |
| 73 | 583.3 | 6.98 | xx |
| 74 | 574.2 | 8.16 | x |
| 75 | 548.3 | 7.86 | xxx |
| 76 | 536.2 | 6.57 | xxx |
| 77 | 522.4 | 6.72 | xxx |
| 78 | 598.2 | 7.49 | x |
| 79 | 520.1 | 7.36 | x |
| 80 | 492.2 | 6.16 | x | x = <10 µM; xx = <1 µM, xxx = <100 nM

Example 48

MC5R Radioligand Binding Assay Using MC5 Receptors from Other Species

Radioligand binding and cAMP assays were also conducted using membranes and cells expressing MC5R cloned from other species (mouse MC5R membranes from Euroscreen, canine, rhesus monkey, cyno monkey, and guinea pig cloned and expressed from cDNA libraries as in Examples 50 and 52. Plasma membranes from the cells were tested in the radioligand assay as in Example 46).

Example 49

Activity of Selected Compounds: Other Species MC5R

Representative compounds of the present invention were tested for binding to MC5R from other species, as in described in Example 48, the results are listed in Table 4.

TABLE 4

Binding of Selected Compounds to MC5R from Different Species

| Cpd. | human MC5R (membrane) $IC_{50}$ (nM) | mouse MC5R (membrane) $IC_{50}$ (nM) | rhesus monkey MC5R (membranes) $IC_{50}$ (nM) |
|---|---|---|---|
| 17 | 30 nM | 2300 nM | 3760 nM |

These results show the selectivity of the compounds of the invention for human MC5R in comparison to MC5R in other species. Whilst there is activity in other species it is significantly reduced in comparison to human MC5R, which would not be expected given the high receptor homology between species.

Example 50

Human MC1R, MC3R and MC4R Radioligand Binding Assay

Radioligand binding assays were carried out using commercial or in-house prepared hMC1R, hMC3R and hMC4R membranes and [$^{125}$I] NDP-MSH, as per hMC5R procedure in Example 46.

In-house plasma membranes were prepared from transfected mammalian cells (prepared as in Example 52, using plasmid DNA containing the human MC1R, MC3R or MC4R gene in a plasmid vector with a mammalian origin of replication):

Adherent cells were washed with warm Hanks buffered saline solution (HBSS). 1 mL of cold HBSS was added to each flask and the cells were scraped off with a rubber policeman. The scraped cells were added to a 50 mL tube on ice. The plates were then rinsed twice with 5 mL cold HBSS and this was also added to the tube. The cells were centrifuged at 1000×g for 5 mins in a bench top centrifuge and the supernatant was decanted. The remaining cell pellet was resuspended in 0.25 M sucrose. The cell suspension was centrifuged again as previously and the pellet resuspended in 5 mL of 0.25 M sucrose containing protease inhibitors. The cells were homogenised by a 10 second pulse with an Ika disperser followed by 30 seconds on ice. The homogenisation and ice incubation was repeated three times. The mixture was then centrifuged at 1260×g for 5 mins. The supernatant was decanted into another centrifuge tube, to which a buffer containing 50 mM Tris, pH 7.4, 12.5 mM MgCl$_2$, 5 mM EGTA and protease inhibitors was added to make the volume up to 30 mL. This was centrifuged at 30,000×g for 90 mins at 4° C. The resulting pellet was resuspended in 1 mL of the buffer above also containing 10% glycerol. Membranes were aliquoted into cryovials which were snap-frozen in a dry-ice/ethanol bath before being stored at −80° C. until required for use.

Example 51

Selectivity of Selected Compounds: hMCR Binding

Representative compounds of the present invention were tested for binding in the hMC1R, hMC3R, hMC4R and hMC5R assays, as described in Examples 46 and 50, the results are listed in Table 5.

TABLE 5 hMCR Binding Selectivity of Selected Compounds

| Cpd. | human MC5R IC$_{50}$ (nM) | human MC1R IC$_{50}$ (nM) | human MC3R IC$_{50}$ (nM) | human MC4R IC$_{50}$ (nM) |
|---|---|---|---|---|
| 17 | 30 nM | >10000 nM | 3050 nM | >10000 nM |
| 66 | 50 nM | >10000 nM | 4960 nM | >10000 nM |

These results demonstrate the selectivity of the compounds of the invention for Human MC5R in comparison to other members of the human melanocortin receptor family.

Example 52

Inhibition or Stimulation of cAMP Signal in Cells Expressing Human MC5R

Transient Transfection of Mammalian Cell Lines:

The mammalian cell line, human embryonic kidney cells (HEK 293), were maintained in Dulbeccos Modified Eagle's medium (DMEM) with 5% fetal bovine serum, L-glutamine, high glucose and antibiotics/antimycotics. On the day prior to transfection, cells were passaged using trypsin/EDTA and seeded into 75 cm$^2$ flasks so that they would be approximately 90% confluent the next day. The next day, the cell media was replaced with fresh antibiotic/antimycotic-containing DMEM. Approximately 100 µl of the transfection lipid Turbofectin 8.0 (Origene Technologies, MD, USA), was diluted in 1.0 mL of serum and antibiotic/antimycotic-free Opti-MEM in a sterile 15 mL tube and incubated for 5 mins at room temperature. Following incubation, approximately 10-20 µg of plasmid DNA expressing the gene of interest (for example: pCMV6-XL4:*Homo sapiens* melanocortin 5 receptor (Origene Technologies, MD, USA)) was diluted into the transfection mix and incubated for a further 30 mins at room temperature. The DNA/lipid solution was then added drop-wise to the media covering the cells while rocking the flask gently. 24 hrs post-transfection, the cells were passaged and seeded directly into two, 75 cm$^2$ flasks and left to recover. 48 hrs post transfection, cells were harvested for use in assays with cell dissociation solution.

Cyclic-Adenosine Monophosphate [cAMP] Stimulation Assay:

HEK 293 cells transiently expressing the melanocortin MC5 receptor were suspended in stimulation buffer (Hanks buffered saline solution (HBSS), 0.1% bovine serum albumin, protease inhibitors and 0.5 mM 3-Isobutyl-1-methylxanthine) at 4×10$^6$ cells/mL. 5 µl of cells, plus the compounds/peptides as described below, were added to wells of a 384-well plate as soon as possible after resuspension.

To detect antagonist activity, test compounds at varying concentrations were diluted in stimulation buffer at four times concentrate and 2.5 µl was added to wells containing cells. 2.5 µl of a four times required concentration of NDP-MSH or alpha-MSH was added to all wells containing compounds. Negative control wells contained two times concentrated NDP-MSH or alpha-MSH alone without compound.

To detect agonist activity, test compounds at varying concentrations were diluted in stimulation buffer at two times concentrate and 5 µl was added to wells containing cells. Positive control wells contained NDP-MSH or alpha-MSH alone (no compound) at two times concentrate Basal level (of cAMP) control wells contained stimulation buffer only (no agonist or compounds). Known concentrations of cAMP (standards) in stimulation buffer were included on the plate, but no cells were added to these wells. The plate was then incubated for 30 mins at 37° C. with gentle shaking. After incubation, 10 µl of lysis buffer (10% Tween 20, 1 M HEPES, 0.1% BSA, protease inhibitors, ddH$_2$O) was added to all wells to be measured. Detection of cAMP was then achieved using the Alphascreen cAMP kit (Perkin Elmer, USA), briefly described as follows. A dilution of 10 µl acceptor beads/mL of lysis buffer was prepared in low light conditions. 5 µl of diluted acceptor beads were added to each well to be measured, then the plate was incubated for 30 mins at room temperature, in the dark, with gentle shaking. In low light conditions, donor beads were diluted at 10 µl/mL of lysis buffer, to which 0.75 µl biotinylated cAMP/mL of lysis buffer was added. This mixture was allowed to incubate for 30 mins at room temperature (in the dark) before proceeding with the assay. Following incubation, 5 µl/mL of biotinylated cAMP/Donor bead mix were added per well in low light conditions and the plate was incubated in the dark, at room temperature, for a further hr. Plates were read on an Envision plate reader (Perkin Elmer) after 1 hr and ~16 hrs incubation. cAMP concentration in the cells was determined by the use of a 'standard curve' generated from the output of known cAMP concentrations as described below.

Each assay plate contained a "standard curve" of known concentrations of cAMP, in 10 fold dilutions. This is an essential part of the assay as there is high inter-plate variability. The plates were read on an Envision multilabel plate reader fitted with Alphascreen technology and the raw data was imported into GraphPad Prism 4 software (GraphPad, USA) for analysis. A curve was fitted to the known concentrations using non-linear regression, specifically using a sigmoidal dose-response equation (Y=Bottom+(Bottom+(Top−Bottom)/1+$10^{logEC50-X}$), where the equation shows the response as a function of the logarithm of concentration. X is the logarithm of peptide/compound concentration and Y is the response. Also considered in this equation are bottom plateau, top plateau of the curve and $EC_{50}$ (effective concentration, 50%).

Example 53

Activity of Selected Compounds: hMC5R

Representative compounds of the present invention were tested for agonism or antagonism of the hMC5R, as described in Example 52, the results are listed in Table 6.

TABLE 6

Agonism and Antagonism of hMC5 by Selected Compounds

| Cpd. | human MC5R $EC_{50}$ (cAMP, agonism) (nM) | human MC5R $IC_{50}$ (cAMP, antagonism of $10^{-6}$ M alpha-MSH) (nM) |
|---|---|---|
| 17 | >10000 | 6000 |
| 66 | >10000 | 600 |

REFERENCES

Andersen, G. N.; Hägglund, M.; Nagaeva, O.; Frängsmyr, L.; Petrovska, R.; Mincheva-Nilsson, L.; Wikberg, J. E. S. *Scand. J. Immunol.* 2005, 61, 279-284 "Quantitative measurement of the levels of melanocortin receptor subtype 1, 2, 3 and 5 and proo-opio-melanocortin peptide gene expression in subsets of human peripheral blood leukocytes"

Barrett, P.; MacDonald, A.; Helliwell, R.; Davidson, G.; Morgan, P. *J. Molec. Endocrin.* 1994, 12, 203-213 "Cloning and expression of a new member of the melanocyte-stimulating hormone receptor family"

Bataille, V.; Snieder, H.; MacGregor, A. J.; Sasieni, P.; Spector, T. D. *J. Invest. Dermatol.* 2002, 119, 1317-1322 "The Influence of Genetics and Environmental Factors in the Pathogenesis of Acne: A Twin Study of Acne in Women"

Bhardwaj, S. S.; Rohrer, T. E.; Arndt, K. A. *Semin. Cutan. Med. Surg.* 2005, 24, 107-112 "Lasers and light therapy for acne vulgaris"

Bohm, M.; Luger, T. A.; Tobin, D. J.; Garcia-Borron, J. C. *J. Invest. Dermatol.* 2006, 126, 1966-1975 "Melanocortin Receptor Ligands: New Horizons for Skin Biology and Clinical Dermatology"

Buggy, J. J. *Biochem J.* 1998, 331, 211-216 "Binding of a-melanocyte-stimulating hormone to its G-protein-coupled receptor on B-lymphocytes activates the Jak/STAT pathway"

Burke, B. M.; Cunliffe, W. J.; *Br. J. Dermatol.* 1984, 112 124-126 "Oral spironolactone therapy for female patients with acne, hirsutism or androgenic alopecia"

Caldwell, H. K.; Lepri, J. J. *Chem. Senses* 2002, 27, 91-94 "Disruption of the fifth melanocortin receptor alters the urinary excretion of aggression-modifying pheromones in male house mice"

Cerdá-Reverter, J. M.; Ling, M. K.; Schiöth, H. B.; Peter, R. E. *J. Neurochem.* 2003, 1354-1367 "Molecular cloning, characterization and brain mapping of the melanocortin 5 receptor in goldfish"

Chen, W.; Kelly, M. A.; Opitz-Araya, X.; Thomas, R. E.; Low, M. J.; Cone, R. D. *Cell,* 1997, 91, 789-798 "Exocrine gland dysfunction in MC5-R-deficient mice: evidence for coordinated regulation of exocrine gland function by melanocortin peptides"

Chhajlani, V.; Muceniece, R.; Wikberg, J. E. S. *BBRC* 1993, 195, 866-873 "Molecular Cloning of a Novel Human Melanocortin Receptor"

Clarke, S. B.; Nelson, A. M.; George, R. E.; Thiboutot, D. M. *Dermatol. Clin.* 2007, 25, 137-146 "Pharmacologic Modulation of Sebaceous Gland Activity: Mechanisms and Clinical Applications".

Cordain, L. *Sem. Cut. Med. Surg.* 2005, 24, 84-91 "Implications for the Role of Diet in Acne"

Cotterill, J. A.; Cunliffe, W. J.; Williamson, B. *Brit. J. Dermatol.* 1971, 85, 93-94 "Severity of Acne and Sebum Excretion Rate"

Danby, F. W. *J. Am. Acad. Dermatol.* 2005, 52, 1071-1072 "Why we have sebaceous glands"

Eisinger, M.; Fitzpatrick, L. J.; Lee, D. H.; Pan, K.; Plata-Salaman, C.; Reitz, A. B.; Smith-Swintosky, V. L.; Zhao, B. WO03/040117 15 May 2003a "Novel 1,2,4-thiadiazole derivatives as melanocortin receptor modulators"

Eisinger, M.; Fitzpatrick, L. J.; Lee, D. H.; Pan, K.; Plata-Salaman, C.; Reitz, A. B.; Smith-Swintosky, V. L.; Zhao, B. WO03040118A1 15 May 2003b "Novel 1,2,4-thiadiazolium derivatives as melanocortin receptor modulators"

Eisinger, M.; Fitzpatrick, L. J.; Lee, D. H.; Pan, K.; Plata-Salaman, C.; Reitz, A. B.; Smith-Swintosky, V. L.; Zhao, B. US2003/0162819A1 Aug. 28, 2003c "Novel 1,2,4-thiadiazolium derivatives as melanocortin receptor modulators"

Eisinger, M.; Fitzpatrick, L. J.; Lee, D. H.; Pan, K.; Plata-Salaman, C.; Reitz, A. B.; Smith-Swintosky, V. L.; Zhao, B. US2003/0176425A1 Sep. 18, 2003d "Novel 1,2,4-thiadiazole derivatives as melanocortin receptor modulators"

Eisinger, M.; Fitzpatrick, L. J.; Lee, D. H.; Pan, K.; Plata-Salaman, C.; Reitz, A. B.; Smith-Swintosky, V. L.; Zhao, B. US2006/0030604A1 Feb. 9, 2006a "Novel 1,2,4-thiadiazolium derivatives as melanocortin receptor modulators"

Eisinger, M.; Fitzpatrick, L. J.; Lee, D. H.; Pan, K.; Plata-Salaman, C.; Reitz, A. B.; Smith-Swintosky, V. L.; Zhao, B. US2006/0128772A1 Jun. 15, 2006b "Novel 1,2,4-thiadiazole derivatives as melanocortin receptor modulators"

Fathi, Z.; Iben, L. G.; Parker, E. M. *Neurochemical Res.* 1995, 20, 107-113 "Cloning, Expression, and Tissue Distribution of a Fifth Melanocortin Receptor Subtype"

Follador, I.; Campelo, L. *Expert Rev. Dermatol.* 2006, 1 181-184 "Impact of acne on quality of life"

Fong, T. M.; Van der Ploeg, L. H. T.; Huang, R.-R. C. U.S. Pat. No. 6,645,738B1 Nov. 11, 2003 "DNA molecules encoding the melanocortin 5 receptor protein from rhesus monkey"

Gantz, I.; Shimoto, Y.; Konda, Y.; Miwa, H.; Dickinson, C. J.; Yamada, T. *BBRC* 1994, 200, 1214-1220 "Molecular cloning, expression and characterization of a fifth melanocortin receptor"

Goldstein, J. A.; Socha-Szott, A.; Thomsen, R. J.; Pochi, P. E.; Shalita, A. R.; Strauss, J. S. *Am. J. Dermatol.* 1982, 6, 760-765 "Comparative effect of isotretinoin and etretinate on acne and sebaceous gland secretion"

Goodfellow, A.; Alaghband-Zadeh, J.; Carter, G.; Cream, J. J.; Holland, S.; Scully, J.; Wise, P. *Brit. J. Dermatol.* 1984, 111, 209-214 "Oral spironolactone improves acne vulgaris and reduces sebum excretion"

Goulden, V.; Mcgeown, C. H.; Cunliffe, W. J. *Brit. J. Dermatol.* 1999, 141, 297-300 "Familial Risk of Adult Acne: A comparison between first-degree relatives of affected and unaffected individuals"

Graefe, T.; Wollina, U.; Schulz, H.-J.; Burgdorf, W. *Dermatology* 2000, 200, 331-333 "Muir-Torre Syndrome—Treatment with Isotretinoin and Interferon Alpha-2a Can Prevent Tumour Development"

Griffon, N.; Mignon, V.; Facchinetti, P.; Diaz, J.; Schwartz, J.-C.; Sokoloff, P. *BBRC* 1994, 200, 1007-1014 "Molecular cloning and characterization of the rat fifth melanocortin receptor"

Gupta, A. K.; Bluhm, R. *Journal of the European Academy of Dermatology and Venereology* 2004 18:1 13 "Seborrheic dermatitis"

Haitina, T.; Klovins, J.; Andersson, J.; Fredriksson, R.; Lagerstrom, M. C.; Larhammar, D.; Larson, E. T.; Schiöth, H. B. *Biochem. J.* 2004, 380, 475-486 "Cloning, tissue distribution, pharmacology and three-dimensional modelling of melanocortin receptors 4 and 5 in rainbow trout suggest close evolutionary relationships of these subtypes"

Harper, J. C. *Semin. Cutan. Med. Surg.* 2005, 24, 103-106 "Hormonal Therapy for Acne using oral contraceptive pills"

Harris, H. H.; Downing, D. T.; Stewart, M. E.; Strauss, J. S. *J. Am. Acad. Dermatol.* 1983, 8, 200-203 "Sustainable rates of sebum secretion in acne patients and matched normal controls"

Hatta, N.; Dixon, C.; Ray, A. J.; Phillips, S. R.; Cunliffe, W. J.; Dale, M.; Todd, C.; Meggit, S.; Birch-Machin, M. A.; Rees, J. L. *J. Invest. Dermatol.* 2001, 116, 564-570 "Expression, candidate gene, and population studies of the melanocortin 5 receptor"

Houseknecht, K. L.; Robertson, A. S.; Xiao, X. US2003/0110518A1 Jun. 12, 2003 "Melanocortin-5 receptor sequences and uses thereof"

Huang, R.-R. C.; Singh, G.; Van der Ploeg, Fong, T. M. *J. Receptor & Signal Transduction Res.* 2000, 20, 47-59 "Species-dependent pharmacological properties of the melanocortin-5 receptor"

Ide, F.; Shimoyama, T.; Horie, N.; Kaneko, T.; Matsumoto, M. *Oral Surg. Oral Med. Oral Pathol. Oral Radiol. Endod.* 1999, 87, 721-724 "Benign lymphoepithelial lesion of the parotid gland with sebaceous differentiation"

Jeong, S. K.; Hwang, S. W.; Choi, S. Y.; An, WM.; Seo, J. T.; Zouboulis, C. C.; Lee, S. H. *J. Investigative Dermatol,* 2007, 127, pS72 "intracellular calcium mobilization is mediated by the melanocortin receptors in SZ95 sebocytes" (Abstract 431, Society for Investigative Dermatology, May 2007, Los Angeles Calif.)

Jih, M. H.; Friedman, P. M.; Goldberg, L. H.; Robles, M.; Glaich, A. S.; Kimyai-Asadi, A. *J. Am. Acad. Dermatol.* 2006, 55, 80-87 "The 1450-nm diode laser for facial inflammatory acne vulgaris: Dose-response and 12-month follow-up study".

Jones, D. H.; King, K.; Miller, A. J.; Cunliffe, W. J. *Brit. J. Dermatol.* 1983, 108, 333-343 "A dose-response study of 13-cis-retinoic acid in acne vulgaris"

Kim, K. S.; Marklund, S.; Rothschild, M. F. *Animal Genetics* 2000, 31, 230-231. "The porcine melanocortin-5-receptor (MC5R) gene: polymorphisms, linkage and physical mapping"

King, K.; Jones, D. H.; Daltrey, D. C.; Cunliffe, W. J. *Brit. J. Dermatol.* 1982, 107, 583-590 "A double-blind study of the effects of 13-cis-retinoic acid on acne, sebum excretion rate and microbial population"

Kligman, A. M. *Brit. J. Dermatol.* 1963, 75, 307-319 "The uses of sebum"

Klovins, J.; Haitina, T.; Ringholm, A.; Löwgren, M.; Fridmanis, D.; Slaidina, M.; Stier, S.; Schiöth, H. B. *Eur. J. Biochem.* 2004, 271, 4320-4331 "Cloning of two melanocortin (MC) receptors in spiny dogfish"

Kruse, R.; Rütten, A.; Schweiger, N.; Jakob, E.; Mathiak, M.; Propping, P.; Mangold, E.; Bisceglia, M; Ruzicka, T. *J. Invest. Dermatol.* 2003, 120, 858-864 "Frequency of Microsatellite Instability in Unselected Sebaceous Gland Neoplasias and Hyperplasias"

Labbé, O.; Desarnaud, F.; Eggerickx, D.; Vassart, G.; Parmentier, M. *Biochem.* 1994, 33, 4543-4549 "Molecular Cloning of a mouse melanocortin 5 receptor gene widely expressed in peripheral tissues"

Ling, M. K.; Hotta, E.; Kilianova, Z.; Haitina, T.; Ringholm, A.; Johansson, L.; Gallo-Payet, N.; Takeuchi, S.; Schiöth, H. B. *Brit. J. Pharmacol.* 2004, 143, 626-637 "The melanocortin receptor subtypes in chicken have high preference to ACTH-derived peptides"

Makrantonaki, E.; Zouboulis, C. C. *Brit. J. Dermatol.* 2007, 156, 428-432 "Testosterone metabolism to 5a-dihydrotestosterone and synthesis of sebaceous lipids is regulated by the peroxisome proliferator-activated receptor ligand linoleic acid in human sebocytes"

Mariappan, M. R.; Fadare, O.; Jain, D. *Arch. Pathol. Lab. Med.* 2004, 128, 245-246 "Sebaceous Differentiation in Salivary Glands"

Mallon, E.; Newton, J. N.; Klassen, A.; Stewart-Brown, S. L.; Ryan, T. J.; Finlay, A. Y. *Brit. J. Dermatol.* 1999, 140, 672-676 "The quality of life in acne: a comparison with general medical conditions using generic questionanaires"

Marqueling A. L.; Zane, L. T. *Semin. Cutan. Med. Surg.* 2005, 24, 92-102 "Depression and Suicidal Behavior in Acne Patients Treated with Isotretinoin: A Systematic Review"

Morgan, C.; Thomas, R. E.; Ma, W.; Novotny, M. V.; Cone, R. D. *Chem. Senses* 2004a, 29, 111-115 "Melanocortin-5 receptor deficiency reduces a pheromonal signal for aggression in male mice"

Morgan, C.; Thomas, R. E.; Cone, R. D. *Horm. Behav.* 2004b, 45, 58-63 "Melanocortin-5 receptor deficiency promotes defensive behaviour in male mice"

Morgan, C.; Cone, R. D. *Behaviour Genetics* 2006, 36, 291-300 "Melanocortin-5 receptor deficiency in mice blocks a novel pathway influencing pheromone-induced aggression"

Mourelatos, K.; Eady, E. A.; Cunliffe, W. J.; Clark, S. M.; Cove, J. H. *Brit. J. Dermatol.* 2007, 156, 22-31 "Temporal changes in sebum excretion and propionibacterial colonization in preadolescent children with and without acne"

Nelson, A. M.; Gilliland, K. L.; Gong, Z.; Thiboutot, D. M. *J. Investigative Dermatol,* 2006, 126, 2178-2189 "13-cis-Retinoic Acid Induces Apoptosis and Cell Cycle Arrest in Human SEB-1 Sebocytes"

Phan, J.; Kanchanapoomi, M.; Liu, P.; Jalian, H.: Gilliland, K.; Nelson, A.; Thiboutot, D.; Kim, J. *J. Investigative Der-* matol. 2007, 127, pS126 "*P. acnes* induces inflammation via TLR2 and upregulates antimicrobial activity in sebocytes" (Abstract 754. Society for Investigative Dermatology, May 2007, Los Angeles Calif.)

Piérard, G. E.; Piérard-Franchimont, T. L. *Dermatologica* 1987, 175, 5-9 "Seborrhoea in Acne-Prone and Acne-Free Patients"

Plewig G, Jansen T. Seborrheic dermatitis. In: Freedberg I M, Eisen A Z, Wolff K, Austen K F, Goldsmith L A, Katz S I, Fitzpatrick T B, (Eds). Dermatology in General Medicine, 5th ed. New York: McGraw Hill, 1999: 1482-1489

Pochi, P. E.; Strauss, J. S. *J. Invest. Dematol.* 1964, 43, 383-388 "Sebum production, casual sebum levels, titratable acidity of sebum and urinary fractional 17-ketosteroid excretion in males with acne"

Porter, A. M. W. *J. Royal Soc. Med.* 2001, 94, 236-237 "Why do we have apocrine and sebaceous glands"

Ringholm, A.; Fredriksson, R.; Poliakova, N.; Yan, Y.-L.; Postlethwait, J. H.; Larhammar, D.; Schiöth, H. B. *J. Neurochem.* 2002, 82, 6-18 "One melanocortin 4 and two melanocortin 5 receptors from zebrafish show remarkable conservation in structure and pharmacology"

Smith, K. R.; Nelson, A.; Cong, Z.; Thiboutot, D. *J. Investigative Dermatol.* 2007a, 127, pS68 "Iron status affects human sebocyte survival" (Abstract 408, Society for investigative Dermatology, May 2007, Los Angeles Calif.)

Smith, R. N.; Mann, N. J.; Braue, A.; Makelainen, H.; Varigos, G. A. *J. Am. Acad. Dermatol.* 2007b, 57, 247-256 The effect of a high-protein, low glycemic-load diet versus a conventional, high glycemic-load diet on biochemical parameters associated with acne vulgaris: A randomized investigator-masked, controlled trial"

Shuster, S. *Lancet* 1976, 7973, 1328-1329 "Biological purpose of acne"

Simpson, N. B. and Cunliffe, W. J. in Rooks' Textbook of Dermatology, 7$^{th}$ Ed 2004 Blackwell Science, Malden Mass, p 43.1-43.75 "Chapter 43. Disorders of the Sebaceous Glands"

Taylor, A.; Namba, K. *Immunology Cell Biol.* 2001, 79, 358-367 "In vitro induction of CD25+CD4+ regulatory T cells by the neuropeptide alpha-melanocyte stimulating hormone (α-MSH)"

Thiboutot, D.; Sivarajah, A.; Gilliland, K.; Cong, Z.; Clawson, G. *J. Invest. Dermatol.* 2000, 115, 614-619 "The melanocortin 5 receptor is expressed in human sebaceous glands and rat preputial cells"

Thody, A. J.; Shuster, S, *Nature* 1973, 245, 207-209 "Possible role of MSH in the mammal"

Thody, A. J.; Cooper, M. F.; Bowden, P. E.; Shuster, S. *J. Endocrinol.* 1975a, 67, 18P-19P "The sebaceous gland response to α-melanocyte-stimulating hormone and testosterone"

Thody, A. J.; Shuster, S. *J. Endocrinol.* 1975b, 64, 503-510 "Control of sebaceous gland function in the rat by α-melanocyte-stimulating hormone"

Thody, A. J.; Goolamali, S. K.; Burton, J. L.; Plummer, N. A.; Shuster, S. *Brit. J. Dermatol.* 1975c, 92, 43-47 "Plasma β-MSH levels in acne vulgaris"

Wikberg, J. E. S. *Exp. Opin. Ther. Patents* 2001, 11, 61-76 "Melanocortin receptors: new opportunities in drug discovery";

Wikberg, J.; Chhajlani, V. U.S. Pat. No. 6,448,032B1 Sep. 10, 2002 "Human melanocyte stimulating hormone receptor polypeptide and DNA"

Williams, C.; Layton, A. M. *Exp. Rev. Dermatol.* 2006, 1, 429-438 "Treatment of Acne: an update"

Yamada, T.; Gantz, I. U.S. Pat. No. 5,622,860, Apr. 22, 1997, "Genes Encoding Melanocortin Receptors"

Yaswen, L.; Diehl, N.; Brennan, M. B.; Hochgeschwender, U. *Nature Med.* 1999, 5, 1066-1070 "Obesity on the mouse model of proo-opiomelanocortin deficiency responds to peripheral melanocortin"

Youn, S.-W.; Park, E.-S.; Lee, D.-H.; Huh, C.-H.; Park, K.-C. *Brit. J. Dermatol.* 2005, 153, 919-924 "Does facial sebum secretion really affect the development of acne?"

Zhang, L.; Anthonavage, M.; Huang, Q.; Li, W.-H.; Eisinger, M. *Ann. N.Y. Acad. Sci.* 2003, 994, 154-161 "Proopiomelanocortin peptides and sebogenesis"

Zhang, L.; Li, W.-H.; Anthonavage, M.; Eisinger, M. *Peptides* 2006, 27, 413-420 "Melanocortin-5 receptor: a marker of human sebocyte differentiation"

Zouboulis, C. C.; Bohm, M. *Exp. Dermatol.* 2004, 13, 31-35 "Neurocrine regulation of sebocytes—a pathogenetic link between stress and acne"

The details of specific embodiments described in this invention are not to be construed as limitations. Various equivalents and modifications may be made without departing from the essence and scope of this invention, and it is understood that such equivalent embodiments are part of this invention.

What is claimed is:

1. A compound of formula (I):

Formula (I)

wherein:

Y is a group of formula —(CR$^9$R$^{10}$)$_n$—;

X is selected from the group consisting —C(=O)—, —OC(=O)—, —NHC(=O)—, —(CR$^{11}$R$^{12}$)$_s$, and —S(=O)$_2$—;

Z is a group of formula —(CR$^{13}$R$^{14}$)$_q$—;

R$^1$ is selected from the group consisting of H, optionally substituted C$_1$-C$_{12}$alkyl, optionally substituted C$_2$-C$_{12}$alkenyl, optionally substituted C$_2$-C$_{12}$alkynyl, optionally substituted C$_2$-C$_{14}$heteroalkyl, optionally substituted C$_3$-C$_{12}$cycloalkyl, optionally substituted 3 to 10 membered heterocycloalkyl, optionally substituted C$_6$-C$_{18}$aryl, and optionally substituted heteroaryl;

R$^2$ and R$^3$ are each independently selected from the group consisting of H, optionally substituted C$_1$-C$_{12}$alkyl, optionally substituted C$_2$-C$_{12}$alkenyl, optionally substituted C$_2$-C$_{12}$alkynyl, optionally substituted C$_2$-C$_{14}$heteroalkyl, optionally substituted C$_3$-C$_{12}$cycloalkyl, optionally substituted 3 to 10 membered heterocycloalkyl, optionally substituted C$_6$-C$_{18}$aryl, and optionally substituted heteroaryl;

R$^4$ is selected from the group consisting of H, C$_1$-C$_{12}$alkyl, optionally substituted C$_2$-C$_{12}$alkenyl, optionally substituted C$_2$-C$_{12}$alkynyl, C$_3$-C$_{12}$cycloalkyl, optionally substituted C$_6$-C$_{18}$aryl, optionally substituted C-linked C$_1$-C$_{18}$heteroaryl, C(=O)R$^{15}$, C(=O)NR$^{16}$R$^{17}$, —C(=NR$^{16}$)NR$^{17}$R$^{18}$, SR$^{20}$, SC(=O)R$^{20}$, SO$_2$R$^{20}$, $OR^{20}$, $ONR^{16}R^{17}$, $OCR^{17}R^{18}R^{20}$, $OC(=O)R^{20}$, $OC(=O)OR^{20}$, $OC(=O)NR^{16}R^{17}$, and $ONR^{16}C(=NR^{17})NR^{18}R^{19}$;

each $R^{5a}$ and $R^{5b}$ are independently selected from the group consisting of H, halogen, $C_1$-$C_{12}$alkyl, $C_1$-$C_{12}$hydroxyalkyl and $C_1$-$C_{12}$haloalkyl, or one or more of $R^{5a}$ and $R^{5b}$ when taken together with one or more of $R^6$, $R^7$ and $R^8$ and the atoms to which they are attached form a moiety selected from the group consisting of an optionally substituted $C_3$-$C_{12}$cycloalkyl, optionally substituted 3 to 10 membered heterocycloalkyl, optionally substituted $C_6$-$C_{18}$aryl, and optionally substituted heteroaryl;

$R^6$, $R^7$ and $R^8$ are each independently selected from the group consisting of H, halogen, hydroxy, optionally substituted $C_1$-$C_{12}$alkyl, optionally substituted $C_2$-$C_{12}$alkenyl, optionally substituted $C_2$-$C_{12}$alkynyl, optionally substituted $C_2$-$C_{14}$heteroalkyl, optionally substituted $C_1$-$C_{10}$heteroalkenyl, optionally substituted $C_3$-$C_{12}$cycloalkyl, optionally substituted 3 to 10 membered heterocycloalkyl, optionally substituted $C_6$-$C_{18}$aryl, optionally substituted heteroaryl, optionally substituted amino, optionally substituted carboxy and $C_1$-$C_{12}$alkyloxy, or (a) when taken together with the carbon atom to which they are attached two or more of $R^6$, $R^7$ and $R^8$ form a moiety selected from the group consisting of optionally substituted $C_2$-$C_{12}$alkenyl, optionally substituted $C_3$-$C_{12}$cycloalkyl, optionally substituted 3 to 10 membered heterocycloalkyl, optionally substituted $C_6$-$C_{18}$aryl, and optionally substituted heteroaryl, or (b) one or more of $R^6$, $R^7$ and $R^8$ when taken together with one or more of $R^{5a}$ and $R^{5b}$ and the atoms to which they are attached form a moiety selected from the group consisting of an optionally substituted $C_3$-$C_{12}$cycloalkyl, optionally substituted 3 to 10 membered heterocycloalkyl, optionally substituted $C_6$-$C_{18}$aryl, and optionally substituted heteroaryl;

each $R^9$ and $R^{10}$ is independently selected from the group consisting of H and optionally substituted $C_1$-$C_{12}$alkyl;

each $R^{11}$ and $R^{12}$ is independently selected from the group consisting of H, and optionally substituted $C_1$-$C_{12}$alkyl;

$R^{13}$ and $R^{14}$ are each independently selected from the group consisting of H, halogen, OH, $C_1$-$C_{12}$alkyl, $C_3$-$C_{12}$cycloalkyl, $C_6$-$C_{18}$aryl, $C_1$-$C_{12}$haloalkyl, $C_1$-$C_{12}$hydroxyalkyl, $C_1$-$C_{12}$alkyloxyl, and $C_1$-$C_{12}$haloalkyloxyl, or when taken together with the carbon to which they are attached $R^{13}$ and $R^{14}$ form a $C_3$-$C_{12}$cycloalkyl group, or, one of $R^{13}$ or $R^{14}$ when taken together with $R^{15}$ or $R^{20}$ and the atoms to which they are attached form a cyclic moiety;

$R^{15}$ is selected from the group consisting of H, optionally substituted $C_1$-$C_{12}$alkyl, optionally substituted $C_3$-$C_{12}$cycloalkyl, optionally substituted $C_6$-$C_{18}$aryl, and optionally substituted heteroaryl, or each $R^{16}$, $R^{17}$, $R^{18}$, $R^{19}$, and $R^{20}$ is independently selected from the group consisting of H, optionally substituted $C_1$-$C_{12}$alkyl, optionally substituted $C_2$-$C_{14}$heteroalkyl, optionally substituted $C_3$-$C_{12}$cycloalkyl, optionally substituted $C_6$-$C_{18}$aryl, and optionally substituted heteroaryl, or any two of $R^{16}$, $R^{17}$, $R^{18}$, $R^{19}$, and $R^{20}$ when taken together with the atoms to which they are attached form an optionally substituted cyclic group, or $R^{15}$ or $R^{20}$, when taken together with one of $R^{13}$ or $R^{14}$ and the atoms to which they are attached, form a cyclic group;

n is an integer selected from the group consisting of 1, 2, 3 and 4;

q is an integer selected from the group consisting of 0, 1, 2, 3, 4, and 5;

r is an integer selected from the group consisting of 1, 2, 3, and 4;

s is an integer selected from the group consisting of 1, 2, 3, and 4;

wherein each optional substituent is independently selected from the group consisting of F, Cl, Br, I, $CH_3$, $CH_2CH_3$, OH, $OCH_3$, $CF_3$, $OCF_3$, $NO_2$, $NH_2$, and CN;

wherein each $C_2$-$C_{14}$heteroalkyl and each 3 to 10 membered heterocycloalkyl contains from 1 to 3 heteroatoms selected from nitrogen, sulfur, or oxygen, and wherein each heteroaryl is independently selected from the group consisting of thiophenyl, benzotriazolyl, benzothiophenyl, benzofuranyl, benzimidazolyl, benzoxazolyl, benzothiazolyl, benzoisothiazolyl, naptho[2,3-b]thiophenyl, furanyl, isoindolizinyl, xantholenyl, phenoxatinyl, pyrrolyl, imidazolyl, pyrazolyl, pyrazinyl, pyrimidinyl, pyridazinyl, tetrazolyl, indolyl, purinyl, quinolinyl, isoquinolinyl, phthalazinyl, naphthyridinyl, quinoxalinyl, cinnolinyl, carbazolyl, phenanthridinyl, acridinyl, phenazinyl, thiazolyl, isothiazolyl, phenothiazinyl, oxazolyl, isooxazlyl, furazanyl, phenoxazinyl, 2-, 3- or 4-pyridyl, 2-, 3-, 4-, 5-, or 8-quinolyl, 1-, 3-, 4-, or 5-isoquinolinyl, 1-, 2-, or 3-indolyl, and 2- or 3-thienyl, or a pharmaceutically acceptable salt or prodrug thereof.

2. A compound according to claim 1 wherein $R^1$ is selected from the group consisting of (a) optionally substituted $C_6$-$C_{18}$aryl wherein the $C_6$-$C_{18}$ aryl is phenyl, biphenyl or naphthyl; (b) optionally substituted $C_1$-$C_{18}$heteroaryl wherein the optionally substituted $C_1$-$C_{18}$ heteroaryl is indol-2-yl, indol-3-yl quinolin-2-yl quinolin-3-yl, isoquinolin-3-yl, quinoxaline-2-yl, benzo[b]furan-2-yl, benzo[b]thiophen-2-yl, benzo[b]thiophen-5-yl, thiazole-4-yl, benzimidazole-5-yl, benzotriazol-5-yl, furan-2-yl, benzo[d]thiazole-6-yl, pyrazole-1-yl, pyrazole-4-yl or; thiophen-2-yl; and (c) optionally substituted $C_2$-$C_{12}$alkenyl of the formula:

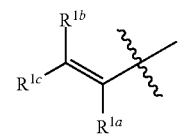

wherein $R^{1a}$ is selected from the group consisting of H, halogen and optionally substituted $C_1$-$C_{12}$ alkyl;

$R^{1b}$ and $R^{1c}$ are each independently selected from the group consisting of H, halogen, optionally substituted $C_1$-$C_{12}$alkyl, optionally substituted $C_2$-$C_{12}$alkenyl, optionally substituted $C_2$-$C_{12}$alkynyl, optionally substituted $C_2$-$C_{14}$heteroalkyl, optionally substituted $C_3$-$C_{12}$cycloalkyl, optionally substituted 3 to 10 membered heterocycloalkyl, optionally substituted $C_6$-$C_{18}$aryl, and optionally substituted heteroaryl;

$R^2$ and $R^3$ are each H or $C_1$-$C_6$ alkyl; or a pharmaceutically acceptable salt thereof.

3. A compound according to claim 2 wherein $R^{5a}$ and $R^{5b}$ are each independently H or $C_1$-$C_6$ alkyl; $R^6$, $R^7$ and $R^8$ are each independently H, methyl, trifluoromethyl, ethyl, 2,2,2- trifluoroethyl, isopropyl, isopropenyl, propyl, 2-ethyl-propyl, 3,3-dimethyl-propyl, butyl, 2-methylbutyl, isobutyl, 3,3-dimethyl-butyl, 2-ethyl-butyl, pentyl, 2-methyl-pentyl, optionally substituted phenyl or optionally substituted $C_1$-$C_5$ heteroaryl wherein the $C_1$-$C_5$ heteroaryl is thiophene, pyrrole, imidazole, pyrazole, pyridine, pyrazine, or tetrazole; $R^{13}$ and $R^{14}$ are each independently H or $C_1$-$C_6$ alkyl; or a pharmaceutically acceptable salt thereof.

4. A compound according to claim 1 wherein X is —C(=O)—; Y is $CH_2$; Z is —$(CH_2)_q$—; $R^{5a}$ is H; $R^{5b}$ is H; r is 1; q is 1, 2, 3, or 4; or a pharmaceutically acceptable salt thereof.

5. A compound according to claim 4 wherein $R^4$ is selected from the group consisting of H, $C_3$-$C_{12}$cycloalkyl, $C_1$-$C_{12}$ alkyl, optionally substituted $C_6$-$C_{18}$aryl, optionally substituted C-linked $C_1$-$C_{18}$heteroaryl, C(=O)$NR^{16}R^{17}$, $OR^{16}$, and $ONR^{16}C(=NR^{17})NR^{18}R^{19}$; or a pharmaceutically acceptable salt thereof.

6. A compound according to 5 wherein $R^4$ is C(=O)$NR^{16}R^{17}$; or a pharmaceutically acceptable salt thereof.

7. A compound according to claim 6 wherein $R^{16}$ and $R^{17}$ when taken together with the nitrogen atom to which they are attached form an optionally substituted 3 to 10 membered heterocycloalkyl selected from the group consisting of piperidin-1-yl, piperidin-4-yl, pyrrolidin-1-yl, pyrrolidin-2-yl azetidin-1-yl, morpholin-4-yl, piperazin-1-yl, 4-methyl-piperazin-1-yl and azepan-1-yl; or a pharmaceutically acceptable salt thereof.

8. A compound according to claim 6 wherein $R^{16}$ and $R^{17}$ are each independently selected from the group consisting of H, $CH_3$, $CH_2CH_3$, $CH_2CH_2CH_3$, $CH(CH_3)_2$, $CH_2CH_2CH_2CH_3$, $CH(CH_3)CH_2CH_3$, $CH_2CH(CH_3)_2$, $C(CH_3)_3$, cyclopropyl, cyclobutyl, cyclopentyl, cyclohexyl, benzyl, and phenyl, or a halogenated derivative thereof; or a pharmaceutically acceptable salt thereof.

9. A compound according to claim 5 wherein $R^1$ is an optionally substituted $C_6$-$C_{18}$aryl selected from the group consisting of optionally substituted phenyl and optionally substituted naphthyl; or a pharmaceutically acceptable salt thereof.

10. A compound according to claim 5 wherein $R^1$ is an optionally substituted $C_2$-$C_{12}$alkenyl of the formula:

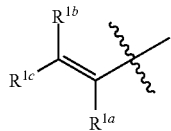

$R^{1a}$ is selected from the group consisting of H, halogen and optionally substituted $C_1$-$C_{12}$ alkyl;
$R^{1b}$ and $R^{1c}$ are each independently selected from the group consisting of H, halogen, optionally substituted $C_1$-$C_{12}$alkyl, optionally substituted $C_2$-$C_{12}$alkenyl, optionally substituted $C_2$-$C_{12}$alkynyl, optionally substituted $C_2$-$C_{14}$heteroalkyl, optionally substituted $C_3$-$C_{12}$cycloalkyl, optionally substituted 3 to 10 membered heterocycloalkyl, optionally substituted $C_6$-$C_{18}$aryl, and optionally substituted heteroaryl or a pharmaceutically acceptable salt thereof.

11. A compound according to claim 10 wherein $R^{1a}$ is H; $R^{1b}$ is H; and $R^{1c}$ is optionally substituted $C_6$-$C_{18}$aryl; or a pharmaceutically acceptable salt thereof.

12. A compound according to claim 11 wherein $R^{1c}$ is optionally substituted phenyl; or a pharmaceutically acceptable salt thereof.

13. A compound according to claim 9 wherein q is 1 or 2; or a pharmaceutically acceptable salt thereof.

14. A compound according to claim 13 wherein $R^6$ and $R^8$ are each independently H, methyl, ethyl, or phenyl; and $R^7$ is H; or a pharmaceutically acceptable salt thereof.

15. A compound according to claim 10 wherein q is 1 or 2; or a pharmaceutically acceptable salt thereof.

16. A compound according to claim 15 wherein $R^6$ and $R^8$ are each independently H, methyl, ethyl, or phenyl; and $R^7$ is H; or a pharmaceutically acceptable salt thereof.

17. A compound according to claim 1 selected from the group consisting of:
N-(((3S,5S)-1-(2,2-diphenylethyl)-3-(2-(guanidinooxy)ethyl)-2-oxo-1,4-diazepan-5-yl)methyl)-2-naphthamide;
N-(((3S,5S)-1-(2,2-diphenylethyl)-2-oxo-3-(pyridin-3-ylmethyl)-1,4-diazepan-5-yl)methyl)-2-naphthamide;
N-(((3S,5S)-1-(2,2-diphenylethyl)-2-oxo-3-(pyridin-4-ylmethyl)-1,4-diazepan-5-yl)methyl)-2-naphthamide;
N-(((3S,5S)-3-butyl-1-(2,2-diphenylethyl)-2-oxo-1,4-diazepan-5-yl)methyl)-2-naphthamide;
(E)-N-(((3S,5S)-3-butyl-1-(2,2-diphenylethyl)-2-oxo-1,4-diazepan-5-yl)methyl)-3-(4-chlorophenyl)acrylamide;
(E)-N-(((3S,5S)-3-(3-amino-3-oxopropyl)-1-(2,2-diphenylethyl)-2-oxo-1,4-diazepan-5-yl)methyl)-3-(4-chlorophenyl)acrylamide;
N-(((3S,5S)-3-(3-amino-3-oxopropyl)-1-(2,2-diphenylethyl)-2-oxo-1,4-diazepan-5-yl)methyl)-2-naphthamide;
(N-(((3S,5S)-3-(cyclohexylmethyl)-1-(2,2-diphenylethyl)-2-oxo-1,4-diazepan-5-yl)methyl)-2-naphthamide;
(N-(((3S,5S)-3-(2-aminoethyl)-1-(3,5-dichlorobenzyl)-2-oxo-1,4-diazepan-5-yl)methyl)-2-naphthamide;
N-(((3S,5S)-1-(2,2-diphenylethyl)-2-oxo-3-(3-oxo-3-(piperidin-1-yl)propyl)-1,4-diazepan-5-yl)methyl)-2-naphthamide;
(E)-3-(4-chlorophenyl)-N-(((3S,5S)-1-(2,2-diphenylethyl)-2-oxo-3-(3-oxo-3-(piperidin-1-yl)propyl)-1,4-diazepan-5-yl)methyl)acrylamide;
N-(((3S,5S)-1-(2,2-diphenylethyl)-2-oxo-3-phenethyl-1,4-diazepan-5-yl)methyl)-2-naphthamide;
(E)-3-(4-chlorophenyl)-N-(((3S,5S)-1-(2,2-diphenylethyl)-2-oxo-3-phenethyl-1,4-diazepan-5-yl)methyl)acrylamide;
N-(((3S,5S)-3-(2-cyclohexylethyl)-1-(2,2-diphenylethyl)-2-oxo-1,4-diazepan-5-yl)methyl)-2-naphthamide;
(E)-3-(4-chlorophenyl)-N-(((3S,5S)-3-(2-cyclohexylethyl)-1-(2,2-diphenylethyl)-2-oxo-1,4-diazepan-5-yl)methyl)acrylamide;
(N-(((3S,5S)-3-benzyl-1-(2,2-diphenylethyl)-2-oxo-1,4-diazepan-5-yl)methyl)-2-naphthamide;
(E)-N-(((3S,5S)-3-benzyl-1-(2,2-diphenylethyl)-2-oxo-1,4-diazepan-5-yl)methyl)-3-(4-chlorophenyl)acrylamide;
(E)-N-(((3S,5S)-3-((1H-imidazol-4-yl)methyl)-1-(2,2-diphenylethyl)-2-oxo-1,4-diazepan-5-yl)methyl)-3-(4-chlorophenyl)acrylamide;
(E)-3-(4-chlorophenyl)-N-(((3S,5S)-1-(2,2-diphenylethyl)-2-oxo-3-(pyridin-2-ylmethyl)-1,4-diazepan-5-yl)methyl)acrylamide;

(E)-3-(4-chlorophenyl)-N-(((3S,5S)-1-(2,2-diphenyl-ethyl)-2-oxo-3-(2-oxo-2-(pyridin-2-ylamino)ethyl)-1,4-diazepan-5-yl)methyl)acrylamide;
(E)-3-(4-chlorophenyl)-N-(((3S,5S)-1-(2,2-diphenyl-ethyl)-2-oxo-3-(2-oxo-2-(piperidin-1-yl)ethyl)-1,4-diazepan-5-yl)methyl)acrylamide;
6-chloro-N-(((3S,5S)-2-oxo-3-(3-oxo-3-(piperidin-1-yl)propyl)-1-((S)-2-phenylbutyl)-1,4-diazepan-5-yl)methyl)-2-naphthamide;
3,4-dichloro-N-(((3S,5S)-2-oxo-3-(3-oxo-3-(piperidin-1-yl)propyl)-1-((S)-2-phenylbutyl)-1,4-diazepan-5-yl)methyl)benzamide;
(5S,9aS)-5-(2-aminobenzyl)-2-((E)-3-(4-chlorophenyl)acryloyl)-7-(2,2-diphenylethyl)hexahydro-1H-imidazo[1,5-d][1,4]diazepin-6(5H)-one;
N-(((3S,5S)-3-(2-aminobenzyl)-1-(2,2-diphenylethyl)-2-oxo-1,4-diazepan-5-yl)methyl)-2-naphthamide;
N-(((3S,5S)-3-butyl-2-oxo-1-((S)-2-phenylbutyl)-1,4-diazepan-5-yl)methyl)-6-chloro-2-naphthamide;
6-chloro-N-(((3S,5S)-3-isopentyl-2-oxo-1-((S)-2-phenylbutyl)-1,4-diazepan-5-yl)methyl)-2-naphthamide;
N-(((3S,5S)-1-(2,2-diphenylethyl)-2-oxo-3-(2-(piperidin-1-yl)benzyl)-1,4-diazepan-5-yl)methyl)-2-naphthamide;
(N-(((3S,5S)-3-(3-(butyl(methyl)amino)-3-oxopropyl)-2-oxo-1-((S)-2-phenylbutyl)-1,4-diazepan-5-yl)methyl)-2-naphthamide;
(N-(((3S,5S)-3-(3-(cyclohexylamino)-3-oxopropyl)-2-oxo-1-((S)-2-phenylbutyl)-1,4-diazepan-5-yl)methyl)-2-naphthamide;
6-chloro-N-(((3S,5S)-3-(2-cyclohexylethyl)-2-oxo-1-((S)-2-phenylbutyl)-1,4-diazepan-5-yl)methyl)-2-naphthamide;
(6-chloro-N-(((3S,5S)-3-hexyl-2-oxo-1-((S)-2-phenylbutyl)-1,4-diazepan-5-yl)methyl)-2-naphthamide;
6-chloro-N-(((3S,5S)-3-(4-hydroxybutyl)-2-oxo-1-((S)-2-phenylbutyl)-1,4-diazepan-5-yl)methyl)-2-naphthamide;
6-chloro-N-(((3S,5S)-3-(2-methoxyethyl)-2-oxo-1-((S)-2-phenylbutyl)-1,4-diazepan-5-yl)methyl)-2-naphthamide;
N-(((3S,5S)-3-(2-(benzyloxy)ethyl)-2-oxo-1-((S)-2-phenylbutyl)-1,4-diazepan-5-yl)methyl)-6-chloro-2-naphthamide; and
6-chloro-N-(((3S,5S)-3-isobutyl-2-oxo-1-((S)-2-phenylbutyl)-1,4-diazepan-5-yl)methyl)-2-naphthamide;
or a pharmaceutically acceptable salt thereof.

18. A compound according to claim 1 wherein said compound is 3,4-dichloro-N-(((3S,5S)-3-(2-hydroxyethyl)-2-oxo-1-((S)-2-phenylbutyl)-1,4-diazepan-5-yl)methyl)benzamide; or a pharmaceutically acceptable salt thereof.

19. A pharmaceutical composition comprising a compound according to claim 1 and a pharmaceutically acceptable carrier, diluent or excipient.

\* \* \* \* \*